US007087418B2

(12) United States Patent
Goldberg et al.

(10) Patent No.: US 7,087,418 B2
(45) Date of Patent: Aug. 8, 2006

(54) PICHIA PASTORIS FORMATE DEHYDROGENASE AND USES THEREFOR

(75) Inventors: Steven L. Goldberg, Basking Ridge, NJ (US); Paul M. Cino, Bound Brook, NJ (US); Ramesh N. Patel, Bridgewater, NJ (US); Venkata B. Nanduri, East Brunswick, NJ (US); Robert M. Johnston, Whitehouse Station, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 420 days.

(21) Appl. No.: 10/320,300

(22) Filed: Dec. 16, 2002

(65) Prior Publication Data

US 2004/0038237 A1 Feb. 26, 2004

Related U.S. Application Data

(60) Provisional application No. 60/375,530, filed on Apr. 25, 2002, and provisional application No. 60/341,933, filed on Dec. 19, 2001.

(51) Int. Cl.
*C12N 9/04* (2006.01)
*C12N 15/00* (2006.01)
*C12N 1/20* (2006.01)
*C07H 21/04* (2006.01)

(52) U.S. Cl. .................. 435/190; 435/4; 435/6; 435/252.3; 435/320.1; 435/69.1; 435/71.1; 435/440; 435/325; 435/254.1; 435/410; 536/23.2; 536/23.74

(58) Field of Classification Search ................ 435/190, 435/4, 6, 252.3, 320.1, 69.1, 71.1, 440, 325, 435/410; 536/23.2, 23.74, 23.1
See application file for complete search history.

(56) References Cited

U.S. PATENT DOCUMENTS 3,654,090 A  4/1972  Schuurs et al.
3,850,752 A  11/1974  Schuurs et al.

(Continued)

FOREIGN PATENT DOCUMENTS

EP  0125023  11/1984
EP  0171496  2/1986

(Continued)

OTHER PUBLICATIONS

Allen, S.J., et al., "Isolation, sequence and overexpression of the gene encoding NAD-dependent formate hydrogenase from the methylotrophic yeast *Candida methylica*", Gene, vol., 162, No. 1, abstract (Aug. 1995).

(Continued)

*Primary Examiner*—Manjunath Rao
*Assistant Examiner*—Yong Pak
(74) *Attorney, Agent, or Firm*—Audrey F. Sher

(57) ABSTRACT

This invention relates to a recombinant *Pichia pastoris* formate dehydrogenase (FDH) enzyme that catalyzes the oxidation of formate to carbon dioxide and the simultaneous reduction of nicotinamide adenine dinucleotide (NAD+) to its reduced form (NADH). Also related are isolated nucleic acids encoding *P. pastoris* FDH polypeptides, and fragments and variants thereof, as well as vectors and host cells comprising these nucleic acids. Further related are isolated, recombinant *P. pastoris* FDH polypeptides, and fragments and variants thereof, and antibodies that specifically bind to *P. pastoris* FDH polypeptides, fragments, or variants. The invention also relates to methods of obtaining isolated *P. pastoris* FDH nucleic acids, polypeptides, and antibodies, and methods of using *P. pastoris* FDH in various reactions for industrial or pharmaceutical applications.

15 Claims, 12 Drawing Sheets

U.S. PATENT DOCUMENTS

| | | | |
|---|---|---|---|
| 3,957,758 | A | 5/1976 | Furlenmeier et al. |
| 4,016,043 | A | 4/1977 | Schuurs et al. |
| 4,373,071 | A | 2/1983 | Itakura |
| 4,391,826 | A | 7/1983 | Mills et al. |
| 4,401,796 | A | 8/1983 | Itakura |
| 4,458,066 | A | 7/1984 | Caruthers et al. |
| 4,598,049 | A | 7/1986 | Zelinka et al. |
| 4,599,311 | A | 7/1986 | Kawasaki |
| 4,751,220 | A | 6/1988 | Parker et al. |
| 4,816,567 | A | 3/1989 | Cabilly et al. |
| 4,845,075 | A | 7/1989 | Murray et al. |
| 4,870,008 | A | 9/1989 | Brake |
| 4,879,234 | A | 11/1989 | Cordes et al. |
| 4,882,279 | A | 11/1989 | Cregg |
| 4,931,373 | A | 6/1990 | Kawasaki et al. |
| 4,939,239 | A | 7/1990 | Matsuhashi et al. |
| 5,037,743 | A | 8/1991 | Welch et al. |
| 5,143,830 | A | 9/1992 | Holland et al. |
| 5,162,228 | A | 11/1992 | Sumino et al. |
| 5,223,409 | A | 6/1993 | Ladner et al. |
| 5,225,539 | A | 7/1993 | Winter |
| 5,283,317 | A | 2/1994 | Saifer et al. |
| 5,389,525 | A | 2/1995 | Hollenberg et al. |
| 5,468,614 | A | 11/1995 | Fields et al. |
| 5,976,813 | A | 11/1999 | Beutel et al. |
| 6,001,590 | A | 12/1999 | Komeda et al. |
| 6,140,088 | A | 10/2000 | Hanson et al. |
| 6,162,913 | A | 12/2000 | Moniot et al. |
| 6,242,234 | B1 | 6/2001 | Kula et al. |
| 6,261,810 | B1 | 7/2001 | Patel et al. |
| 6,283,173 | B1 | 9/2001 | Osborne |
| 6,468,781 | B1 | 10/2002 | Hanson et al. |
| 6,486,331 | B1 | 11/2002 | Hanson et al. |

FOREIGN PATENT DOCUMENTS

| | | |
|---|---|---|
| EP | 0173494 | 3/1986 |
| EP | 0184187 | 6/1986 |
| EP | 0210532 | 2/1987 |
| EP | 0284338 | 9/1988 |
| EP | 0432695 | 6/1991 |
| EP | 0486948 | 5/1992 |
| EP | 0490667 | 6/1992 |
| EP | 0497192 | 8/1992 |
| EP | 0560269 | 9/1993 |
| EP | 0560274 | 9/1993 |
| EP | 0299108 B1 | 5/1994 |
| EP | 0926240 A2 | 6/1999 |
| JP | 10-23896 | 1/1989 |
| SU | 543672 | 1/1977 |
| WO | WO 86/01533 | 3/1986 |
| WO | WO 87/02671 | 5/1987 |
| WO | WO 90/02809 | 3/1990 |
| WO | WO 91/17271 | 11/1991 |
| WO | WO 92/01047 | 1/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | WO 93/24449 | 12/1993 |
| WO | WO 94/10300 | 5/1994 |

OTHER PUBLICATIONS

Sakai, Y., "Regulation of the Formate Dehydrogenase Gene, FDH1, in the Methylotrophic Yeast *Candida boidinii* and Growth Characteristics of an FDH1—Disrupted Strain on Methanol, Methylamine, and Choline", Journal of Bacteriology, vol. 179, No. 14, pp. 4480–4485 (Jul. 1997).

NCBI Entrez Accession No. gi|BAA36159, Ui, S. et al., Feb. 13, 1999.

NCBI Entrez Accession No. gi|T36396, Murphy, L. et al., Jan. 31, 2000.

Altschul, S.F. et al., "Basic Local Alignment Search Tool", J. Mol. Biol., vol. 215, pp.l 403–410 (1990).

Altschul, S.F. et al., "Gapped BLAST and PSI–BLAST: a new generation of protein database search programs", Nucleic Acids Research, vol. 25, No. 17, pp. 3389–3402 (1997).

Alwine, J.C. et al., "Method for detection of specific RNAs in agarose gels by transfer to diazobenzyloxymethyl–paper and hybridization with DNA probes", Proc. Natl. Acad. Sci. USA, vol. 74, No. 12, pp. 5350–5354 (1977).

Ausubel, F.M. et al., eds., "Preparation of Yeast DNA, RNA and Proteins", Current Protocols in Molecular Biology, vol. 2, John Wiley & Sons, Inc., publ., pp. 13.11.1–13.11.4 (1997).

Barbas III, C.F. et al., "Assembly of combinatorial antibody libraries on phage surfaces: The gene III site", Proc. Natl. Acad. Sci. USA, vol. 88, pp. 7978–7982 (1991).

Barrish, J.C. et al., "Aminodiol HIV Protease Inhibitors. 1. Design, Synthesis, and Preliminary SAR", J. Med. Chem., vol. 37, pp. 1758–1768 (1994).

Bartel, P. et al., "Elimination of False Positives That Arise in Using the Two–Hybrid System", BioTechniques, vol. 14, No. 6, pp. 920–924 (1993).

Beidler, C.B. et al., "Cloning and High Level Expression of a Chimeric Antibody with Specificity for Human Carcinoembryonic Antigen", The Journal of Immunology, vol. 141, No. 11, pp. 4053–4060 (1988).

Berezov, T.T. et al., "Effect of Substrate and Product Analogs on the Activity of L–lysine α–oxidase from Trichoderma SP", Biochemistry International, vol. 17, No. 3, pp. 529–534 (1988).

Better, M. et al., "*Escherichia coli* Secretion of an Active Chimeric Antibody Fragment", Science, vol. 240, pp. 1041–1043 (1988).

Bird, I.M., Chapter 29: "Size Separation and Quantification of mRNA by Northern Analysis", Methods in Molecular Biology, vol. 105: Phospholipid Signaling Protocols, Humana Press Inc., publ., Bird, I.M., ed., pp. 325–336 (1998).

Blondelle, S.E. et al., "Novel antimicrobial compounds identified using synthetic combinatorial library technology", TIB Tech, vol. 14, pp. 60–65 (1996).

Bommarius, A.S. et al., "Synthesis and Use of Enantiomerically Pure tert–Leucine", Tetrahedron: Asymmetry, vol. 6, No. 12, pp. 2851–2888 (1995).

Botstein, D. et al., "Construction of a Genetic Linkage Map in Man Using Restriction Fragment Length Polymorphisms", Am. J. Hum. Genet., vol. 32, pp. 314–331 (1980).

Bradford, M.M., "A Rapid and Sensitive Method for the Quantitation of Microgram Quantities of Protein Utilizing the Principle of Protein–Dye Binding", Analytical Biochemistry, vol. 72, pp. 248–254 (1976).

Brown, C.M. et al., eds., Introduction to Biotechnology, Blackwell Scientific Publications, publ., pp. v–vii (table of contents) (1987).

Brown, J.P. et al., "Protein Antigens of Normal and Malignant Human Cells Identified by Immunoprecipitation with Monoclonal Antibodies", The Journal of Biological Chemistry, vol. 255, No. 11, pp. 4980–4983 (1980).

Brown, J.P. et al., "Structural Characterization of Human Melanoma–Associated Antigen p97 with Monoclonal Antibodies", The Journal of Immunology, vol. 127, No. 2, pp. 539–546 (1981).

Carell, T. et al., "A Novel Procedure for the Synthesis of Libraries Containing Small Organic Molecules", Angew. Chem. Int. Ed. Engl., vol. 33, No. 20, pp. 2059–2061 (1994).

Carell, T. et al., "A Solution–Phase Screening Procedure for the Isolation of Active Compounds from a Library of Molecules", Angew. Chem. Int. Ed. Engl., vol. 33, No. 20, pp. 2061–2064 (1994).

Carrillo, H. et al., "The Multiple Sequence Alignment Problem in Biology", SIAM J. Appl. Math., vol. 48, No. 5, pp. 1073–1082 (1988).

Chen, K. et al, "Regulated Secretion of Prolactin by the Mouse Insulinoma Cell Line βTC–3", Bio/Technology, vol. 13, pp. 1191–1197 (1995).

Cho, C.Y. et al., "An Unnatural Biopolymer", Science, vol. 261, pp. 1303–1307 (1993).

Clackson, T. et al., "Making antibody fragments using phage display libraries", Nature, vol. 352, pp. 624–628 (1991).

Cole, S.P.C. et al., "The EBV–Hybridoma Technique and its Application to Human Lung Cancer", Monoclonal Antibodies and Cancer Therapy, Alan R. Liss, Inc., New York, publ., Reisfeld, R.A. et al., eds., pp. 77–96 (1985).

Crueger, W. et al., Biotechnology; A Textbook of Industrial Microbiology, Second Edition, Sinauer Associates, Inc., Sunderland, MA, publ., pp. vii–x (table of contents) (1989).

Cull, M.G. et al., "Screening for receptor ligands using large libraries of peptides linked to the C terminus of the lac repressor", Proc. Natl. Acad. Sci. USA, vol. 89, pp. 1865–1869 (1992).

Cwirla, S.E. et al., "Peptides on phage: A vast library of peptides for identifying ligands", Proc. Natl. Acad. Sci. USA, vol. 87, pp. 6378–6382 (1990).

De Clercq,E., "Toward Improved Anti–HIV Chemotherapy: Therapeutic Strategies for Intervention with HIV Infections", Journal of Medicinal Chemistry, vol. 28, No. 14, pp. 2491–2517 (1995).

Devlin, J.J. et al., "Random Peptide Libraries: A Source of Specific Protein Binding Molecules", Science, vol. 249, pp. 404–406 (1990).

DeWitt, S.H. et al., "'Diversomers': An approach to nonpeptide, nonoligomeric chemical diversity", Proc. Natl. Acad. Sci. USA, vol. 90, pp. 6909–6913 (1993).

Eilers, M. et al., "Binding of a specific ligand inhibits import of a purified precursor protein into mitochondria", Nature, vol. 322, pp. 228–232 (1986).

Erb, E. et al., "Recursive deconvolution of combinatorial chemical libraries", Proc. Natl. Acad. Sci. USA, vol. 91, pp. 11422–11426 (1994).

Ettmayer, P. et al., "Novel, Extended Transition State Mimic in HIV–1 Protease Inhibitors with Peripheral $C_2$–Symmetry", Bioorganic & Medicinal Chemistry Letters, vol. 4, No. 24, pp. 2851–2856 (1994).

Felici, F., "Selection of Antibody Ligands from a Large Library of Oligopeptides Expressed on a Multivalent Exposition Vector", J. Mol. Biol., vol. 222, pp. 301–310 (1991).

Fields, S. et al., "The two–hybrid system: an assay for protein–protein interactions", TIG, vol. 10, No. 8, pp. 286–292 (1994).

Fodor, S.P.A. et al., "Light–Directed, Spatially Addressable Parallel Chemical Synthesis", Science, vol. 251, pp. 767–773 (1991).

Fodor, S.P.A. et al., "Multiplexed biochemical assays with biological chips", Nature, vol. 364, pp. 555–556 (1993).

Freeman, W.M. et al., "Quatitative RT–PCR: Pitfalls and Potential", BioTechniques, vol. 26, pp. 112–125 (1999).

Fuchs, P. et al., "Targeting Recombinant Antibodies to the Surface of Escherichia coli: Fusion to a Peptidogylcan Associated Lipoprotein", Bio/Technology, vol. 9, pp. 1369–1372 (1991).

Galfre, G. et al., "Antibodies to major histocompatibility antigens produced by hybrid cell lines", Nature, vol. 266, pp. 550–552 (1977).

Gallop, M.A. et al., "Applications of Combinatorial Technologies to Drug Discovery, 1. Background and Peptide Combinatorial Libraries", Journal of Medicinal Chemistry, vol. 37, No. 9, pp. 1233–1251 (1994).

Garnier, L. et al., "The Intracellular Domain of the Rabbit Prolactin Receptor Is Able to Promote the Secretion of a Passenger Protein via an Unusual Secretory Pathway in Lepidopteran Cells", Bio/Technology, vol. 13, pp. 1101–1104 (1995).

Garrard, L.J. et al., "$F_{ab}$ Assembly and Enrichment in a Monovalent Phage Display System", Bio/Technology, vol. 9, pp. 1373–1377 (1991).

Gefter, M.L. et al., "A Simple Method for Polyethylene Glycol–Promoted Hybridization of Mouse Myeloma Cells", Somatic Cell Genetics, vol. 3, No. 2, pp. 231–236 (1977).

Ghosh, A.K. et al., "Potent HIV Protease Inhibitors: The Development of Tetrahydrofuranylglycines as Novel $P_2$–Ligands and Pyrazine Amides as $P_3$–Ligands", J. Med. Chem., vol. 36, pp. 2300–2310 (1993).

Glazer, A.N. et al., Microbial Biotechnology: Fundamentals of Applied Microbiology, W.H. Freeman and Company, New York, publ., pp. ix–xv (table of contents) (1995).

Gleeson, M.A. et al., "Transformation of the Methylotropic Yeast Hansenula polymorpha", Journal of General Microbiology, vol. 132, pp. 3459–3465 (1986).

Goeddel, D.V., "Systems for Heterologous Gene Expression", Methods in Enzymololgy, vol. 185, Academic Press, Inc., publ., pp. 3–7 (1990).

Gordon, E.M. et al., "O–Sulfated β–Lactam Hydroxamic Acids (Monosulfactams). Novel Monocyclic β–Lactam Antibiotics of Synthetic Origin", J. Am. Chem. Soc., vol. 104, pp. 6053–6060 (1982).

Grady, S. et al., "Improved Enzymic Assay for Serum Formate with Colorimetric Endpoint", Journal of Analytical Toxicology, vol. 10, pp. 1–5 (1986).

Gram, H. et al., "In vitro selection and affinity maturation of antibodies from a naive combinatorial immunoglobulin library", Proc. Natl. Acad. Sci. USA, vol. 89, pp. 3576–3580 (1992).

Griffin, A.M. et al., Methods in Molecular Biology, vol. 24: Computer Analysis of Sequence Data, Part I, Humana Press, Inc., publ., pp. vii–viii (table of contents) (1994).

Griffiths, A.D. et al., "Human anti–self antibodies with high specificity from phage display libraries", The EMBO Journal, vol. 12, No. 2, pp. 725–734 (1993).

Gulavita, N.K. et al., "Polydiscamide A: A New Bioactive Depsipeptide from the Marine Sponge Discodermia sp.", J. Org. Chem., vol. 57, pp. 1767–1772 (1992).

Gusella, J.F., "DNA Polymorphism and Human Disease", Ann. Rev. Biochem., vol. 55, pp. 831–854 (1986).

Hanson, R.L. et al., "Synthesis of allysine ethylene acetal using phenylalanine dehydrogenase from *Thermoactinomyces intermedius*", Enzyme and Microbial Technology, vol. 26, pp. 348–358 (2000).

Hanson, R.L. et al., "Synthesis of L–β–Hydroxyvaline from α–Keto–β–hydroxyisovalerate Using Leucine Dehydrogenase from Bacillus Species", Bioorganic Chemistry, vol. 18, pp. 116–130 (1990).

Hanson, R.L. et al., "Transformation of Nε–CBZ–L–lysine to CBZ–L–oxylysine using L–amino acid oxidase from *Providencia alcalifaciens* and L–2–hydroxy–isocaproate dehydrogenase from *Lactobacillus confusus*", Appl. Microbiol. Biotechnol., vol. 37, pp. 599–603 (1992).

Hawkins, R.E. et al., "Selection of Phage Antibodies by Binding Affinity: Mimicking Affinity Maturation", J. Mol. Biol., vol. 226, pp. 889–896 (1992).

Hay, B.N. et al., "Bacteriophage cloning and *Escherichia coli* expression of a human IgM Fab", Hum. Antibod. Hybridomas, vol. 3, pp. 81–85 (1992).

Henikoff, S. et al., "Amino acid substitution matrices from protein blocks", Proc. Natl. Acad. Sci. USA, vol. 89, pp. 10915–10919 (1992).

Hiep, T.T. et al., "Transformation in the Methylotropic Yeast *Pichia methanolica* utilizing Homologous ADE1 and Heterologous *Saccharomyces cerevisiae* ADE2 and LEU2 Genes as Genetic Markers", Yeast, vol. 9, pp. 1189–1197 (1993).

Hoogenboom, H.R. et al., "Multi–subunit proteins on the surface of filamentous phage: methodologies for displaying antibody (Fab) heavy and light chains", Nucleic Acids Research, vol. 19, No. 15, pp. 4133–4137 (1991).

Hou, C.T. et al., "NAD–Linked Formate Dehydrogenase from Methanol–Grown *Pichia pastoris* NRRL–Y–7556", Archives of Biochemistry and Biophysics, vol. 216, No. 1, pp. 296–305 (1982).

Houghten, R.A. et al., "Generation and use of synthetic peptide combinatorial libraries for basic research and drug discovery", Nature, vol. 354, pp. 84–86 (1991).

Houghten, R.A. et al., "The Use of Synthetic Peptide Combinatorial Libraries for the Identification of Bioactive Peptides", BioTechniques, vol. 13, No. 3, pp. 412–421 (1992).

Hummel, W. et al., "Dehydrogenases for the synthesis of chiral compounds", Eur. J. Biochem., vol. 184, pp. 1–13 (1989).

Hurt, E.C. et al., "The first twelve amino acids (less than half of the pre–sequence) of an imported mitochondrial protein can direct mouse cytosolic dihydrofolate reductase into the yeast mitochondrial matrix", The EMBO Journal, vol. 4, No. 8, pp. 2061–2068 (1985).

Huse, W.D. et al., "Generation of a Large Combinatorial Library of the Immunoglobulin Repertoire in Phage Lambda", Science, vol. 246, pp. 1275–1281 (1989).

Iwabuchi, K. et al., "Use of the two–hybrid system to identify the domain of p53 involved in oligomerization", Oncogene, vol. 8, pp. 1693–1696 (1993).

Jones, P.T. et al., "Replacing the complementarity–determining regions in a human antibody with those from a mouse", Nature, vol. 321, pp. 522–525 (1986).

Karanewsky, D.S. et al., "(Phosphinyloxy)acyl Amino Acid Inhibitors of Angiotensin Converting Enzyme (ACE). 1. Discovery of (S)–1–[6–Amino–2–[[hydroxy(4–phenylbutyl) phosphinyl]oxy]–1–oxohexyl]–L–proline, a Novel Orally Active Inhibitor of ACE", J. Med. Chem. vol. 31, pp. 204–212 (1988).

Kato, R. et al., "Solution Structure of HIV–1 Protease–Allophenylnorstatine Derivative Inhibitor Complex Obtained from Molecular Dynamics Stimulation", Chem. Pharm. Bull., vol. 42, No. 1, pp. 176–178 (1994).

Köhler, G. et al., "Continuous cultures of fused cells secreting antibody of predefined specificity", Nature, vol. 256, pp. 495–497 (1975).

Koster, W.H. et al., "Structure–Activity Relationships Leading to an Orally–Absorbed Monobactam Activated by an N–1–0SO$_3$ moiety", 25th Intersci. Conf. Antimicrobial Agents and Chemotherapy, Abstract No. 368, p. 158 (1985).

Kozbor, D. et al., "The production of monoclonal antibodies from human lymphocytes", Immunology Today, vol. 4, No. 3, pp. 72–79 (1983).

Kubo, T. et al., "Location of a region of the muscarinic acetylcholine receptor involved in selective effector coupling", FEBS Letters, vol. 241, No. 1, 2, pp. 119–125 (1988).

Kula, M.–R., "Enzyme catalyzed reductions of carbonyl groups", Proceedings of Chiral Europe (1994).

Kwak, L.W. et al., "Induction of Immune Responses in Patients with B–Cell Lymphoma Against the Surface–Immunoglobulin Idiotype Expressed by Their Tumors", The New England Journal of Medicine, vol. 327, No. 17, pp. 1209–1215 (1992).

Lam, K.S., "Application of combinatorial library methods in cancer research and drug discovery", Anti–Cancer Drug Design, vol. 12, pp. 145–167 (1997).

Lam, K.S. et al., "A new type of synthetic peptide library for identifying ligand–binding activity", Nature, vol. 354, pp. 82–84 (1991).

Lerner, E.A., "How to Make a Hybridoma", The Yale Journal of Biology and Medicine, vol. 54, pp. 387–402 (1981).

Lesk, A.M., ed., Computational Molecular Biology: Sources and Methods for Sequence Analysis, Oxford University Press, publ. (table of contents) (1988).

Licitra, E.J. et al., "A three–hybrid system for detecting small ligand–protein receptor interactions", Proc. Natl. Acad. Sci. USA, vol. 93, pp. 12817–12821 (1996).

Liu, A.Y. et al., "Chimeric mouse–human IgG1 antibody that can mediate lysis of cancer cells", Proc. Natl. Acad. Sci. USA, vol. 84, pp. 3439–3443 (1987).

Liu, A.Y. et al., "Production of a Mouse–Human Chimeric Monoclonal Antibody to CD20 with Potent Fc–Dependent Biologic Activity", The Journal of Immunology, vol. 139, No. 10, pp. 3521–3526 (1987).

Loviny, T. et al., "Ribitol dehydrogenase of *Klebsiella aerogenes*: Sequence of the structural gene", Biochem. J., vol. 230, pp. 579–585 (1985).

Luckow, V.A. et al., "Trends in the Development of Baculovirus Expression Vectors", Bio/Technology, vol. 6, pp. 47–55 (1988).

Male, D. et al., Advanced Immunology, Gower Medical Publishing, publ., pp. v–vi (table of contents) (1991).

Madura, K. et al., "N–recognin/Ubc2 Interactions in the N–end Rule Pathway", The Journal of Biological Chemistry, vol. 268, No. 16, pp. 12046–12054 (1993).

Marsh, D.G., "Preparation and Properties of 'Allergoids' Derived from Native Pollen Allergens by Mild Formatin Treatment", Int. Arch Allergy, vol. 41, pp. 199–215 (1971).

McCafferty, J. et al., "Phage antibodies: filamentous phage displaying antibody variable domains", Nature, vol. 348, pp. 552–555 (1990).

Medolsohn, A.R. et al., "Applications of interaction traps/two–hybrid systems to biotechnology research", Current Opinion in Biotechnology, vol. 5, pp. 482–486 (1994).

Mishell, B.B. et al., eds., Selected Methods in Cellular Immunology, W.H. Freeman and Company, San Francisco, publ., pp. vii–xiv (table of contents) (1980).

Morrison, S.L., "Transfectomas Provide Novel Chimeric Antibodies", Science, Vo. 229, pp. 1202–1207 (1985).

Mullis, K. et al., "Specific Enzymatic Amplification of DNA In Vitro: The Polymerase Chain Reaction", Cold Spring Harbor Symposia on Quantitative Biology, vol. 51, pp. 263–273 (1986).

Needleman, S.B. et al., "A General Method Applicable to the Search for Similarities in the Amino Acid Sequence of Two Proteins", J. Mol. Biol., vol. 48, pp. 443–453 (1970).

Nishimura, Y. et al., "Recombinant Human–Mouse Chimeric Monoclonal Antibody Specific for Common Acute Lymphocytic Leukemia Antigen", Cancer Research, vol. 47, pp. 999–1005 (1987).

Oi, V.T. et al., "Chimeric Antibodies", BioTechniques, vol. 4, No. 3, pp. 214–221 (1986).

Parker, W. et al., "Preparation of crystalline salts of [3S(Z)]–2–[[[1–(2–amino–4–thiozolyl)–2–[[2,2–dimethyl–4–oxo–1–(sulfooxy)–3–azetidinyl]amino]–2–oxyethylidene]amino] oxy]acetic acid with choline and erthromycin as antibacterials", Chemical Abstracts, No. 109:116074a, p. 371 (1988).

Patel, R.N. et al., "Preparation of chiral synthon for HIV protease inhibitor: stereoselective microbial reduction of N–protected α–aminochioreketone", Tetrahedron: Asymmetry, vol. 8, No. 15, pp. 2547–1552 (1997).

Patel, R.N. et al., "Stereoselective reduction of β–keto esters by *Geotrichum candidum*", Enzyme Microb. Technol., vol. 14, pp. 731–738 (1992).

Phizicky, E.M. et al., "Protein–Protein Interactions: Methods for Detection and Analysis", Microbiological Reviews, vol. 59, No. 1, pp. 94–123 (1995).

Raap, A.K., "Advances in fluorescence in situ hybridization", Mutation Research, vol. 400, pp. 287–298 (1998).

Ren, L.–Q. et al., "Lipopolysaccaride–induced expression of IP–10 mRNA in rat brain and in cultured rat astrocytes and microglia", Molecular Brain Research, vol. 59, pp. 256–263 (1998).

Richardson, C.D., ed., Methods in Molecular Biology, vol. 39: Baculorvirus Expression Protocols, Humana Press, Inc., publ., pp. ix–x (table of contents) (1995).

Robl, J.A. et al., "Dual Metalloprotease Inhibitors: Mercaptoacetyl–Based Fused Heterocyclic Dipeptide Mimetics as Inhibitors of Angiotensin–Converting Enzyme and Neutral Endopeptidase", J. Med. Chem. vol. 40, pp. 1570–1577 (1997).

Roux, K.H., "Optimization and Troubleshooting in PCR", PCR Methods and Applications, pp. S185–S193 (1995).

Scott, J.K. et al., "Searching for Peptide Ligands with an Epitope Library", Science, vol. 249, pp. 386–390 (1990).

Shaw, D.R. et al., "Mouse/Human Chimeric Antibodies to a Tumor–Associated Antigen: Biologic Activity of the Four Human IgG Subclasses", J. Natl. Cancer Inst., vol. 80, No. 19, pp. 1553–1559 (1988).

Sjölander, S. et al., "Integrated Fluid Handling System for Biomolecular Interaction Analysis", Anal. Chem., vol. 63, pp. 2338–2345 (1991).

Slusarchyk, W.A. et al., "β–lactam Synthesis: Chemospecific Sulfonation and Cyclization of the β–hydroxyvaline Nucleus", Tetrahedron Letters, vol. 27, No. 25, pp. 2789–2792 (1986).

Songyang, Z. et al., "SH2 Domains Recognize Specific Phosphopeptide Sequences", Cell, vol. 72, pp. 767–778 (1993).

Spector, T. et al., "Herpes and Human Ribonucleotide Reductases: Inhibition by 2–acetylpyridine 5–[(2–chloroanilino)–thiocarbonyl]–thiocarbonohydrazone (384U87)", Biochemical Pharmacology, vol. 42, No. 1, pp. 91–96 (1991).

Sun, L.K. et al., "Chimeric antibody with human constant regions and mouse variable regions directed against carcinoma–associated antigen 17–1A", Proc. Natl. Acad. Sci. USA, vol. 84, pp. 214–218 (1987).

Szabo, A. et al., "Surface plasmon resonance and its use in biomolecular interaction analysis (BIA)", Current Opinion in Structural Biology, vol. 5, pp. 699–705 (1995).

Szwajcer, E. et al., "Production of α–keto acids: 2. Immobilized whole cells of Providencia sp. PCM 1298 containing L–amino acid oxidase", Enzyme Microb. Technol., vol. 4, pp. 409–413 (1982).

Tam, T.F. et al., "Intriguing Structure–Activity Relations Underlie the Potent Inhibition of HIV Protease by Norstatine–Based Peptides", J. Med. Chem. vol. 35, pp. 1318–1320 (1992).

Tarr, G.E., Chapter 6: "Manual Edman Sequencing System", Methods of Protein Microcharacterization, Humana Press, Clifton, NJ, publ., J.E. Silver, ed., pp. 155–194 (1986).

Tessier, D.C. et al., "Enhanced secretion from insect cells of a foreign protein fused to the honeybee melittin signal peptide", Gene, vol. 98, pp. 177–183 (1991).

Tom, R.L. et al., "Improved yields of the extracellular domain of the epidermal growth factor receptor produced using the baculovirus expression system by medium replacement following infection", Appl. Microbiol. Biotechnol., vol. 44, pp. 53–58 (1995).

Tom, R.L. et al., Chapter 12: "Scale–Up of Recombinant Virus and Protein Production in Stirred–Tank Reactors", Methods in Molecular Biology, vol. 39: Baculovirus Expression Protocols, Humana Press, Inc., Totowa, NJ, publ., Richardson, C.D., ed., pp. 203–224 (1995).

Verhoeyen, M. et al., "Reshaping Human Antibodies: Grafting an Antilysozyme Activity", Science, vol. 239, pp. 1534–1536 (1988).

Vidal, M. et al., "Reverse two–hybrid and one–hybrid systems to detect dissociation of protein–protein and DNA–protein interactions", Proc. Natl. Acad. Sci. USA, vol. 93, pp. 10315–10320 (1996).

Weiss, S.A. et al., Chapter 4: "Insect Cell Culture in Serum–Free Media", Methods in Molecular Biology, vol. 39: Baculovirus Expression Protocols, Humana Press, Totowa, NJ, publ., Richardson, C.D., ed., pp. 79–95 (1995).

Wie, S.I. et al., "Suppression of Reaginic Antibodies with Modified Allergens", Int. Archs Allergy Appl. Immun., vol. 64, pp. 84–99 (1981).

Wong, C.–H. et al., "Enzyme–Catalyzed Organic Synthesis: NAD(P)H Cofactor Regeneration by Using Glucose 6–Phosphate and the Glucose–6–phosphate Dehydrogense from *Leuconostoc mesenteroides*", J. Am. Chem. Soc., vol. 103, pp. 4890–4899 (1981).

Wong, C.-H. et al., "Enzyme–Catalyzed Organic Synthesis: NAD(P)H Cofactor Regeneration Using Ethanol/Alcohol Dehydrogenase/Aldehyde Dehydrogenase and Methanol/Alcohol Dehydrogenase/Aldehyde Dehydrogenase/Formate Dehydrogenase", J. Org. Chem., vol. 47, pp. 2816–2818 (1982).

Wong, C.H. et al., Enzymes in Synthetic Organic Chemistry, Elsevier Science Ltd., publ., pp. v–xi (table of contents) (1994).

Wood, C.R. et al., "The synthesis and in vivo assembly of functional antibodies in yeast", Nature, vol. 314, pp. 446–449 (1985).

Wu, S.-Y. et al., "Insecticidal Activity of Optically Active 1,3,2–Oxazaphospholidine 2–Sulfides and 1,3,2–Benzodioxaphosphorin 2–Sulfides", J. Pesticide Sci., vol. 12, pp. 221–227 (1987).

Yang, M. et al., "Protein–peptide interactions analyzed with the yeast two–hybrid system", Nucleic Acids Research, vol. 23, No. 7, pp. 1152–1156 (1995).

Yeh, M.-Y. et al., "A Cell–Surface Antigen which is Present in the Ganglioside Fraction and Shared by Human Melanomas", Int. J. Cancer, vol. 29, pp. 269–275 (1982).

Yeh, M.-Y. et al., "Cell surface antigens of human melanoma identified by monoclonal antibody", Proc. Natl. Acad. Sci. USA, vol. 76, No. 6, pp. 2927–2931 (1979).

Yoshida, C. et al., "Studies on Monocyclic β–lactam Antibiotics: II. Synthesis and Antibacterial Activity of 3–acylamino–2–azetidinone–1–oxysulfonic Acids", The Journal of Antibiotics, vol. 38, No. 11, pp. 1536–1549 (1985).

Zang, M. et al, "Production of Recombinant Proteins in Chinese Hamster Ovary Cells Using A Protein–Free Cell Culture Medium", Bio/Technology, vol. 13, pp. 389–392 (1995).

Zervos, A.S. et al., "Mxi1, a Protein That Specifically Interacts with Max to Bind Myc–Max Recognition Sites", Cell, vol. 72, pp. 223–232 (1993).

Zuckermann, R.N. et al., "Discovery of Nanomolar Ligands for 7–Transmembrane G–Protein–Coupled Receptors from a Diverse N–(Substituted)glycine Peptoid Library", J. Med. Chem., vol. 37, pp. 2678–2685 (1994).

```
 +1    Met Lys Ile Val Leu Val Leu Tyr Ser Ala Gly Lys His Ala Ala Asp Glu Pro Lys Leu
   1   ATGAAAATCGTTCTCGTTTTGTACTCCGCTGGTAAGCACGCCGCCGATGAACCAAAGTTG
       TACTTTTAGCAAGAGCAAAACATGAGGCGACCATTCGTGCGGCGGCTACTTGGTTTCAAC
 +1    Tyr Gly Cys Ile Glu Asn Glu Leu Gly Ile Arg Gln Trp Leu Glu Lys Gly Gly His Gln
  61   TATGGTTGTATCGAAAATGAATTGGGTATTAGACAATGGCTTGAGAAGGGCGGCCATGAA
       ATACCAACATAGCTTTTACTTAACCCATAATCTGTTACCGAACTCTTCCCGCCGGTACTT
 +1    Leu Val Thr Thr Ser Asp Lys Glu Gly Glu Asn Ser Glu Leu Glu Lys His Ile Pro Asp
 121   TTGGTTACTACATCAGACAAAGAGGGTGAAAACTCTGAGTTAGAAAAGCACATTCCTGAC
       AACCAATGATGTAGTCTGTTTCTCCCACTTTTGAGACTCAATCTTTTCGTGTAAGGACTG
 +1    Ala Asp Val Ile Ile Ser Thr Pro Phe His Pro Ala Tyr Ile Thr Lys Glu Arg Ile Gln
 181   GCTGATGTGATTATTTCCACTCCATTCCATCCAGCCTACATCACGAAGGAGAGAATCCAA
       CGACTACACTAATAAAGGTGAGGTAAGGTAGGTCGGATGTAGTGCTTCCTCTCTTAGGTT
 +1    Lys Ala Lys Lys Leu Lys Leu Leu Val Val Ala Gly Val Gly Ser Asp His Ile Asp Leu
 241   AAAGCCAAGAAGCTGAAGTTGTTGGTCGTTGCTGGTGTCGGTTCCGACCACATTGACTTG
       TTTCGGTTCTTCGACTTCAACAACCAGCAACGACCACAGCCAAGGCTGGTGTAACTGAAC
 +1    Asp Tyr Ile Glu Gln Asn Gly Leu Asp Ile Ser Val Leu Glu Val Thr Gly Ser Asn Val
 301   GACTACATTGAACAAAATGGCCTAGATATTTCGGTCCTAGAGGTTACTGGTTCCAACGTT
       CTGATGTAACTTGTTTTACCGGATCTATAAAGCCAGGATCTCCAATGACCAAGGTTGCAA
 +1    Val Ser Val Ala Glu His Val Val Met Thr Ile Leu Asn Leu Val Arg Asn Phe Val Pro
 361   GTTTCAGTGGCTGAGCATGTCGTTATGACTATATTGAACTTGGTGAGAAACTTTGTTCCA
       CAAAGTCACCGACTCGTACAGCAATACTGATATAACTTGAACCACTCTTTGAAACAAGGT
 +1    Ala His Glu Gln Ile Val Asn Pro Gly Trp Asp Val Ala Ala Ile Ala Lys Asp Ala Tyr
 421   GCTCACGAGCAAATTGTTAACCCCGGCTGGGACGTTGCTGCCATCGCCAAGGACGCCTAC
       CGAGTGCTCGTTTAACAATTGGGGCCGACCCTGCAACGACGGTAGCGGTTCCTGCGGATG
 +1    Asp Ile Glu Gly Lys Thr Ile Ala Thr Ile Gly Ala Gly Arg Ile Gly Tyr Arg Val Leu
 481   GATATTGAAGGTAAGACCATCGCAACAATTGGTGCTGGAAGAATTGGTTACAGAGTCTTA
       CTATAACTTCCATTCTGGTAGCGTTGTTAACCACGACCTTCTTAACCAATGTCTCAGAAT
 +1    Glu Arg Leu Val Ala Phe Asn Pro Lys Glu Leu Leu Tyr Tyr Asp Tyr Gln Gly Leu Pro
 541   GAGAGACTTGTGGCTTTCAACCCTAAGGAATTGTTGTACTACGACTACCAAGGTCTTCCA
       CTCTCTGAACACCGAAAGTTGGGATTCCTTAACAACATGATGCTGATGGTTCCAGAAGGT
 +1    Lys Glu Ala Glu Glu Lys Val Gly Ala Arg Arg Val Asp Thr Val Glu Glu Leu Val Ala
 601   AAAGAGGCCGAGGAAAAAGTTGGTGCCAGAAGAGTCGACACTGTCGAGGAGCTGGTTGCT
       TTTCTCCGGCTCCTTTTTCAACCACGGTCTTCTCAGCTGTGACAGCTCCTCGACCAACGA
 +1    Gln Ala Asp Val Val Thr Val Asn Ala Pro Leu His Ala Gly Thr Lys Gly Leu Val Asn
 661   CAAGCCGATGTTGTTACCGTCAATGCCCCACTGCACGCAGGTACTAAGGGTTTAGTTAAC
       GTTCGGCTACAACAATGGCAGTTACGGGGTGACGTGCGTCCATGATTCCCAAATCAATTG
 +1    Lys Glu Leu Leu Ser Lys Phe Lys Lys Gly Ala Trp Leu Val Asn Thr Ala Arg Gly Ala
 721   AAGGAGCTTCTGTCCAAGTTCAAGAAGGGTGCTTGGTTGGTTAACACAGCCAGAGGTGCC
       TTCCTCGAAGACAGGTTCAAGTTCTTCCCACGAACCAACCAATTGTGTCGGTCTCCACGG
 +1    Ile Cys Asn Ala Gln Asp Val Ala Asp Ala Val Ala Ser Gly Gln Leu Arg Gly Tyr Gly
 781   ATCTGCAATGCTCAAGATGTCGCTGATGCCGTTGCATCTGGTCAATTGAGAGGTTACGGT
       TAGACGTTACGAGTTCTACAGCGACTACGGCAACGTAGACCAGTTAACTCTCCAATGCCA
 +1    Gly Asp Val Trp Phe Pro Gln Pro Ala Pro Lys Asp His Pro Trp Arg Asp Met Arg Asn
 841   GGTGACGTCTGGTTCCCTCAGCCAGCTCCAAAGGACCATCCATGGAGAGATATGAGAAAC
       CCACTGCAGACCAAGGGAGTCGGTCGAGGTTTCCTGGTAGGTACCTCTCTATACTCTTTG
 +1    Lys Tyr Gly Tyr Gly Asn Ala Met Thr Pro His Tyr Ser Gly Thr Thr Leu Asp Ala Gln
 901   AAGTACGGATACGGAAACGCCATGACTCCTCATTACTCAGGTACCACTTTGGACGCCCAG
       TTCATGCCTATGCCTTTGCGGTACTGAGGAGTAATGAGTCCATGGTGAAACCTGCGGGTC
```

FIGURE 1A

```
      +1     Val Arg Tyr Ala Glu Gly Thr Lys Asn Ile Leu Asn Ser Phe Leu Thr Lys Lys Phe Asp
     961    GTCAGATATGCCGAAGGTACCAAGAACATCTTGAACTCATTCCTTACCAAGAAGTTTGAC
            CAGTCTATACGGCTTCCATGGTTCTTGTAGAACTTGAGTAAGGAATGGTTCTTCAAACTG
      +1     Tyr Arg Pro Gln Asp Val Ile Leu Leu Asn Gly Lys Tyr Lys Thr Lys Ala Tyr Gly Asn
    1021    TACAGACCTCAAGATGTCATTCTTTTGAACGGTAAGTACAAGACCAAGGCTTATGGTAAT
            ATGTCTGGAGTTCTACAGTAAGAAAACTTGCCATTCATGTTCTGGTTCCGAATACCATTA
      +1     Asp Lys Lys Val Ala ***
    1081    GACAAAAAGGTCGCATAAA
            CTGTTTTTCCAGCGTATTT
```

FIGURE 1B

```
   1    CTAATTCTATTCAGTGTGCTGACCTACACGTAATGATGTCGTAACCCAGTTAAA
        GATTAAGATAAGTCACACGACTGGATGTGCATTACTACAGCATTGGGTCAATTT
  55    TGGCCGAAAAACTATTTAAGTAAGTTTATTTCTCCTCCAGATGAGACTCTCCTT
        ACCGGCTTTTTGATAAATTCATTCAAATAAAGAGGAGGTCTACTCTGAGAGGAA
 109    CTTTTCTCCGCTAGTTATCAAACTATAAACCTATTTTACCTCAAATACCTCCAA
        GAAAAGAGGCGATCAATAGTTTGATATTTGGATAAAATGGAGTTTATGGAGGTT
 163    CATCACCCACTTAAACAATGAAAATCGTTCTCGTTTTGTACTCCGCTGGTAAGC
        GTAGTGGGTGAATTTGTTACTTTTAGCAAGAGCAAAACATGAGGCGACCATTCG
 217    ACGCCGCCGATGAACCAAAGTTGTATGGTTGTATCGAAAATGAATTGGGTATTA
        TGCGGCGGCTACTTGGTTTCAACATACCAACATAGCTTTTACTTAACCCATAAT
 271    GACAATGGCTTGAGAAGGGCGGCCATGAATTGGTTACTACATCAGACAAAGAGG
        CTGTTACCGAACTCTTCCCGCCGGTACTTAACCAATGATGTAGTCTGTTTCTCC
 325    GTGAAAACTCTGAGTTAGAAAAGCACATTCCTGACGCTGATGTGATTATTTCCA
        CACTTTTGAGACTCAATCTTTTCGTGTAAGGACTGCGACTACACTAATAAAGGT
 379    CTCCATTCCATCCAGCCTACATCACGAAGGAGAGAATCCAAAAAGCCAAGAAGC
        GAGGTAAGGTAGGTCGGATGTAGTGCTTCCTCTCTTAGGTTTTTCGGTTCTTCG
 433    TGAAGTTGTTGGTCGTTGCTGGTGTCGGTTCCGACCACATTGACTTGGACTACA
        ACTTCAACAACCAGCAACGACCACAGCCAAGGCTGGTGTAACTGAACCTGATGT
 487    TTGAACAAAATGGCCTAGATATTTCGGTCCTAGAGGTTACTGGTTCCAACGTTG
        AACTTGTTTTACCGGATCTATAAAGCCAGGATCTCCAATGACCAAGGTTGCAAC
 541    TTTCAGTGGCTGAGCATGTCGTTATGACTATATTGAACTTGGTGAGAAACTTTG
        AAAGTCACCGACTCGTACAGCAATACTGATATAACTTGAACCACTCTTTGAAAC
 595    TTCCAGCTCACGAGCAAATTGTTAACCCCGGCTGGGACGTTGCTGCCATCGCCA
        AAGGTCGAGTGCTCGTTTAACAATTGGGGCCGACCCTGCAACGACGGTAGCGGT
 649    AGGACGCCTACGATATTGAAGGTAAGACCATCGCAACAATTGGTGCTGGAAGAA
        TCCTGCGGATGCTATAACTTCCATTCTGGTAGCGTTGTTAACCACGACCTTCTT
 703    TTGGTTACAGAGTCTTAGAGAGACTTGTGGCTTTCAACCCTAAGGAATTGTTGT
        AACCAATGTCTCAGAATCTCTCTGAACACCGAAAGTTGGGATTCCTTAACAACA
 757    ACTACGACTACCAAGGTCTTCCAAAAGAGGCCGAGGAAAAAGTTGGTGCCAGAA
        TGATGCTGATGGTTCCAGAAGGTTTTCTCCGGCTCCTTTTTCAACCACGGTCTT
 811    GAGTCGACACTGTCGAGGAGCTGGTTGCTCAAGCCGATGTTGTTACCGTCAATG
        CTCAGCTGTGACAGCTCCTCGACCAACGAGTTCGGCTACAACAATGGCAGTTAC
 865    CCCCACTGCACGCAGGTACTAAGGGTTTAGTTAACAAGGAGCTTCTGTCCAAGT
        GGGGTGACGTGCGTCCATGATTCCCAAATCAATTGTTCCTCGAAGACAGGTTCA
 919    TCAAGAAGGGTGCTTGGTTGGTTAACACAGCCAGAGGTGCCATCTGCAATGCTC
        AGTTCTTCCCACGAACCAACCAATTGTGTCGGTCTCCACGGTAGACGTTACGAG
 973    AAGATGTCGCTGATGCCGTTGCATCTGGTCAATTGAGAGGTTACGGTGGTGACG
        TTCTACAGCGACTACGGCAACGTAGACCAGTTAACTCTCCAATGCCACCACTGC
1027    TCTGGTTCCCTCAGCCAGCTCCAAAGGACCATCCATGGAGAGATATGAGAAACA
        AGACCAAGGGAGTCGGTCGAGGTTTCCTGGTAGGTACCTCTCTATACTCTTTGT
1081    AGTACGGATACGGAAACGCCATGACTCCTCATTACTCAGGTACCACTTTGGACG
        TCATGCCTATGCCTTTGCGGTACTGAGGAGTAATGAGTCCATGGTGAAACCTGC
1135    CCCAGGTCAGATATGCCGAAGGTACCAAGAACATCTTGAACTCATTCCTTACCA
        GGGTCCAGTCTATACGGCTTCCATGGTTCTTGTAGAACTTGAGTAAGGAATGGT
1189    AGAAGTTTGACTACAGACCTCAAGATGTCATTCTTTTGAACGGTAAGTACAAGA
        TCTTCAAACTGATGTCTGGAGTTCTACAGTAAGAAAACTTGCCATTCATGTTCT
1243    CCAAGGCTTATGGTAATGACAAAAAGGTCGCATAATTGAAATGTATTTAATTTG
        GGTTCCGAATACCATTACTGTTTTTCCAGCGTATTAACTTTACATAAATTAAAC
1297    ATATTAAGTAAATGAATGATTATGACTTTATGAATTCACGTGGCCCAGCCGGCC
        TATAATTCATTTACTTACTAATACTGAAATACTTAAGTGCACCGGGTCGGCCGG
1351    GTCTCGGATCGGTACCTCGAGCCGCGGCGGCCGCCAGCTTGGGCCCGAACAAAA
        CAGAGCCTAGCCATGGAGCTCGGCGCCGCCGGCGGTCGAACCCGGGCTTGTTTT
1405    ACTCATCTCAGAAGAGGATCTGAATAGCGCCGTCGACCATCATCATCATCATCA
        TGAGTAGAGTCTTCTCCTAGACTTATCGCGGCAGCTGGTAGTAGTAGTAGTAGT
1459    TTGAGTTTTAGCCTTAGACATGACTGTTCCTCAGTTCAAGTTGGGCACTTACGA
        AACTCAAAATCGGAATCTGTACTGACAAGGAGTCAAGTTCAACCCGTGAATGCT
```

FIGURE 1C

1513  GAAGACCGGTCTTGCTAGATTCTAATCAAGAGGATGTCAGAATGCCATTTGCCT
      CTTCTGGCCAGAACGATCTAAGATTAGTTCTCCTACAGTCTTACGGTAAACGGA
1567  GAGAGATGCAGGCTTCATTTTTGATACTTTTTTATTTGTACCCTATATAGTATA
      CTCTCTACGTCCGAAGTAAAAACTATGAAAAAATAAACATGGGATATATCATAT
1621  GGATTTTTTTTGTCATTTTGTTTCTTCTCGTACGAGCTTGCTCCTGATCAGCCT
      CCTAAAAAAAACAGTAAAACAAAGAAGAGCATGCTCGAACGAGGACTAGTCGGA
1675  ATCTCCCAGCTGATGA
      TAGAGGGTCGACTACT

FIGURE 1D

```
   1 atgaagatcg ttttagtctt atatgatgct ggtaagcacg ctgctgatga
  51 agaaaaatta tatggttgta ctgaaaataa attaggtatt gctaattggt
 101 taaaagatca aggtcatgaa ctaattacta cttctgataa agaaggtgaa
 151 acaagtgaat tggataaaca tatcccagat gctgatatta tcatcaccac
 201 tcctttccat cctgcttata tcactaagga aagacttgac aaggctaaga
 251 acttaaaatt agtcgttgtc gctggtgttg gttctgatca cattgattta
 301 gattatatta atcaaacagg taagaaaatc tcagtcttgg aagttacagg
 351 ttctaatgtt gtctctgttg ctgaacacgt tgtcatgacc atgcttgtct
 401 tggttagaaa tttcgttcca gcacatgaac aaattattaa ccacgattgg
 451 gaggttgctg ctatcgctaa ggatgcttac gatatcgaag gtaaaactat
 501 tgctaccatt ggtgctggta gaattggtta cagagtcttg gaaagattac
 551 tcccttttaa tccaaaagaa ttattatact acgattatca agctttacca
 601 aaagaagctg aagaaaaagt tggtgctaga agagttgaaa atattgaaga
 651 attagttgct caagctgata tcgttacagt taatgctcca ttacacgcag
 701 gtacaaaagg tttaattaat aaggaattat tatctaaatt taaaaaaggt
 751 gcttggttag tcaataccgc aagaggtgct atttgtgttg ctgaagatgt
 801 tgcagcagct ttagaatctg gtcaattaag aggttacggt ggtgatgttt
 851 ggttcccaca accagctcca aaggatcacc catggagaga tatgagaaat
 901 aaatatggtg ctggtaatgc catgactcct cactactctg gtactacttt
 951 agatgctcaa acaagatacg ctgaaggtac taaaaatatc ttggaatcat
1001 tctttactgg taaatttgat tacagaccac aagatattat cttattaaat
1051 ggtgaatacg ttactaaagc ttacggtaaa cacgataaga aataa
```

FIGURE 1E

```
-504  CGG GGN DDD SGG NSG GCG GVV ATA GGC GND GDA

-468  CCS CCT KDD TTY CCC GGR AAG AAG ACA TSS SBC YCA

-432  TGG ATG GAA ATT TCC CCA TGA TGC CCA TGG ATT TCC

-396  CSS YTG AAG ATC ATC CGG SGD AAA CGA AGG CAT CGT

-360  NAC GCC CTG GAT TTC GGG AAT ATG GAC GGA CGA CAC

-324  CAG GAC CTR AAG CCA TTC CCT CAT CGC TGA TGC CAC

-288  CAA AGG TCT CAA AAA CGG CAC TAA TGC TGT CCG TGT

-252  GGT TCA TCA AGT CCT GCC GAG GCT CTT CGT AAC GTT

-216  TAT TTA ACG CAT CCT CGC AGG CCC GGA AAC AGA TGA

-180  CCA GAG TAG GTT TAT GAA AAT TAT CCT TAC CCA GGA

-144  CAG GCC CCG TCC CCT TTG ACA CAA TCC TGT GTC AGG

-108  CCT GCC GAA CAG GCG TTT TTT TGT GGA ATA CGG AAA

-72  GCA AAG GGT TGA TGG TTC CCG CCG TCA TGG CAG TCA

-36  CAT GCC GAT GAC GGA CAA TCG AAG GAT CTT TTT TCA

M   S   L   S   G   K   I   A   A   V   T   G
   1  ATG TCC CTT TCT GGA AAA ATC GCC GCA GTC ACG GGT

A   A   Q   C   I   G   K   A   I   A   L   R
  37  GCA GCC CAG TGT ATC GGC AAG GCC ATT GCG CTT CGT
```

FIGURE 1F

```
        L   A   K   D   G   A   D   V   I   L   L   D
 73    CTG GCC AAG GAT GGC GCG GAT GTC ATC CTG CTC GAC

V   K   Q   D   T   L   A   E   T   A   K   E
109    GTC AAG CAG GAC ACG CTT GCC GAA ACC GCA AAG GAA

V   E   A   L   G   R   R   A   V   A   L   T
145    GTT GAA GCT CTC GGC CGG CGC GCT GTG GCC CTG ACG

A   D   I   S   N   R   D   Q   F   R   S   T
181    GCC GAT ATC AGC AAC CGC GAC CAG TTC CGC AGC ACG

L   A   D   A   A   K   T   L   G   G   L   D
217    CTG GCC GAT GCA GCA AAG ACG CTC GGC GGC CTG GAC

I   M   V   N   N   A   G   I   C   Q   V   K
253    ATC ATG GTC AAC AAT GCG GGG ATC TGT CAG GTC AAG

P   I   L   D   I   E   P   A   E   I   E   K
289    CCG ATC CTG GAC ATC GAG CCT GCG GAA ATC GAG AAG

I   F   S   I   N   V   Q   G   V   L   W   G
325    ATC TTC AGC ATC AAC GTT CAG GGC GTG CTC TGG GGC

M   Q   A   A   A   T   L   F   K   E   K   G
361    ATG CAG GCG GCT GCG ACC CTC TTC AAG GAG AAG GGC

T   K   G   K   I   I   N   A   C   S   I   A
397    ACC AAG GGC AAG ATC ATC AAT GCC TGC TCG ATC GCC

G   H   E   G   Y   P   L   L   G   A   Y   S
433    GGC CAT GAA GGC TAT CCC CTT CTG GGC GCC TAT TCC

A   T   K   F   A   V   R   A   L   T   Q   S
469    GCG ACC AAA TTC GCC GTC CGC GCC CTG ACG CAG TCG

A   A   K   E   L   A   S   S   G   I   T   V
505    GCC GCC AAG GAA CTC GCG TCC TCG GGC ATT ACC GTC

N   S   Y   C   P   G   I   V   G   T   D   M
541    AAT TCC TAC TGC CCC GGC ATT GTC GGA ACC GAC ATG

W   V   T   I   D   K   R   M   A   E   I   T
577    TGG GTC ACG ATC GAC AAG CGC ATG GCC GAA ATC ACC

G   T   E   I   G   A   T   Y   K   K   Y   V
613    GGT ACG GAA ATC GGC GCG ACC TAC AAG AAA TAC GTT

E   G   I   A   L   G   R   V   E   T   A   D
649    GAA GGA ATC GCT CTT GGC CGC GTG GAG ACG GCG GAC
```

FIGURE 1G

```
      D   V   A   G   F   V   A   Y   L   S   S   S
685   GAT GTG GCG GGC TTC GTC GCC TAT TTG TCC AGC AGT

D   A   D   Y   M   T   G   Q   S   V   L   I
721   GAC GCC GAT TAC ATG ACG GGT CAG TCC GTC CTG ATC

N   G   G   P   V   F   R   *----------------
757   AAC GGT GGT CCC GTT TTC CGC TGA GAT CAT AAA AAA

----------------------------------------------
769   SAG GGC CGG TTT CCC GCG CCC CCT TTT TTG TCA GCG

----------------------------------------------
781   GCC GAT CAG ACG GCC GBG CTG CCA GGC TTC GGC GGC

----------------------------------------------
793   CCC TTC CGG GTC CTG MMC TTC AAC GGA AAT GAC ATA

----------------------------------------------
805   GTC CAG GGC GCT CAT GAC CCT GTT GCC AAG CAT CAT

----------------------------------------------
817   TTC CGA AAG CTC GTC GAG NAG ATC GCT GTC CGC CTG

----------------------------------------------
829   ACG GGC CAC ATC TTC ACG CAT GAT CAT CCG GGC CGA

----------------------------------------------
841   CAT TTC TCC GCC CAG CAG GTG GGC CGG ATC CGA GCT

----------------------------------------------
853   CGG TAC CAA GCK TGA TGC ATA GCT TGA GTA
```

FIGURE 1H

PICHIA PASTORIS FORMATE DEHYDROGENASE AND USES THEREFOR

This invention claims priority from provisional U.S. application Ser. No. 60/341,933 filed Dec. 19, 2001 and provisional U.S. application Ser. No. 60/375,530 filed Apr. 25, 2002, which are incorporated herein by reference in their entirety.

FIELD OF THE INVENTION

This invention relates to a recombinant formate dehydrogenase (FDH) cloned from *Pichia pastoris* which catalyzes the oxidation of formate to carbon dioxide and the simultaneous reduction of nicotinamide adenine dinucleotide (NAD+) to its reduced form (NADH). The invention also relates to isolated nucleic acids comprising nucleotide sequences which encode *P. pastoris* FDH polypeptides, vectors and host cells comprising these nucleic acids, isolated *P. pastoris* FDH polypeptides, and antibodies that specifically bind to *P. pastoris* FDH polypeptides. The invention further relates to methods of obtaining isolated *P. pastoris* FDH nucleic acids, polypeptides, and antibodies, and methods of using *P. pastoris* FDH in reactions required for the synthesis of industrial or pharmaceutical compounds.

BACKGROUND OF THE INVENTION

Many enzymes that are useful in the synthesis of fine chemicals and pharmaceutical intermediates require co-factors such as NAD(H) or NADP(H), for example the bioconversion of ketones to alcohols (see M.-R. Kula, 1994, "Enzyme Catalyzed Reductions or Carbonyl Groups", *Proceedings of Chiral Europe*, 27–33). However, it is prohibitively expensive to add the co-factor as needed in large-scale reactions. A method of regenerating the co-factor is required to make such syntheses economically feasible. This can often be accomplished by the use of a second enzyme capable of reducing the oxidized form of the co-factor, which is then utilized by the primary enzyme to complete the desired conversion.

Enzymatic regeneration has been accomplished through the use of glucose-6-phosphate dehydrogenase (C.-H. Wong and G. M. Whitesides, 1994, *J. Am. Chem. Soc.* 103:4890–4899), alcohol dehydrogenase (C.-H. Wong and G. M. Whitesides, 1982, *J. Org. Chem.* 47:2816–2818), and formate dehydrogenase (M.-R. Kula, 1994, "Enzyme Catalyzed Reductions or Carbonyl Groups", *Proceedings of Chiral Europe*, 27–33; also see C.-H. Wong and G. M. Whitesides, 1994, "Enzymes in Organic Chemistry", Pergamon Press, Elsevier Science Ltd., Oxford, UK).

FDH is the preferred enzyme for reactions requiring NADH as co-factor because it uses an inexpensive substrate, sodium formate, as a hydrogen source and releases only $CO_2$ as a byproduct. This enzyme has been isolated from a number of methylotropic bacterial (Berezin et al., SU 543672) and yeast (Cordes et al., EP 86109675 and U.S. Pat. No. 4,879,234; Hollenberg et al., U.S. Pat. No. 5,389,525) strains for use in large-scale co-factor regeneration. In addition, the FDH enzyme has been isolated from *P. pastoris* strain NRRL-Y-7556 (C. T. Hou et al., 1982, *Arch. Biochem. Biophys.* 216:296–305).

Despite the great interest in the various forms of formate dehydrogenase, the isolation of the FDH gene and expression of the recombinant enzyme from *Pichia pastoris* has not been reported. Given the importance of FDH, it is highly desirable to have an additional source of the enzyme. Although use of the native organism to induce expression of FDH would require the use of methanol, a flammable and hazardous solvent, heterologous expression of the protein in a host such as *Escherichia coli* would allow inexpensive, high-level production of the enzyme while avoiding the requirement of methanol induction. In addition, recombinant production of the enzyme is expected to be a faster and less expensive process than purification. Accordingly, the present invention provides an novel recombinant formate dehydrogenase isolated from *P. pastoris* which can be used in various reactions, including those useful for synthesis of fine chemicals and pharmaceutical intermediates.

SUMMARY OF THE INVENTION

It is an object of the present invention to provide a novel recombinant FDH cloned from the yeast *Pichia pastoris*, and variants, modifications, and fragments thereof.

It is also an object of the invention to provide isolated *P. pastoris* FDH polynucleotides, e.g., DNA and RNA molecules, comprising nucleotide sequences encoding *P. pastoris* FDH polypeptides, as well as nucleic acid variants, modifications, fragments, and complementary sequences thereof.

It is a further object of the present invention to provide nucleic acid probes and primers, as well as vectors and host cells, comprising *P. pastoris* FDH polynucleotides.

It is yet a further object of the present invention to provide isolated, recombinant *P. pastoris* FDH enzyme, and fragments, variants, and modifications thereof.

It is another object of the present invention to provide antibodies and antibody fragments that specifically bind to the *P. pastoris* FDH enzyme, or enzyme variants, modifications, or fragments thereof.

It is yet another object of the present invention to provide methods of using the *P. pastoris* FDH polynucleotides, vectors, and host cells to produce *P. pastoris* formate dehydrogenase.

It is still another object of the present invention to provide methods of using the recombinant *P. pastoris* FDH enzyme in enzymatic reactions requiring the presence of the co-factor NADH. In various aspects, this process uses cell-free extracts or whole cells expressing recombinant *P. pastoris* formate dehydrogenase.

It is a further object of the present invention to provide methods of purifying the *P. pastoris* FDH enzyme, or enzyme variants, modifications, or fragments thereof, using the disclosed antibodies or antibody fragments.

Additional objects and advantages afforded by the present invention will be apparent from the detailed description and exemplification hereinbelow.

BRIEF DESCRIPTION OF THE FIGURES

The appended drawings of the figures are presented to further describe the invention and to assist in its understanding through clarification of its various aspects. In the figures of the present invention, the nucleotide and amino acid sequences are represented by their one-letter abbreviations.

FIGS. 1A–1B illustrate the protein-coding sequence and the protein encoded by the *Pichia pastoris* FDH gene. The middle line shows the sense strand of the protein-coding sequence (SEQ ID NO:1); the bottom line shows the antisense strand of the protein-coding sequence (SEQ ID NO:2); the top line shows the deduced amino acid sequence (SEQ ID NO:5).

FIGS. 1C–1D illustrate the coding and non-coding regions of the *Pichia pastoris* FDH gene. The top line shows the sequence of the sense strand (SEQ ID NO:3); the bottom line shows the sequence of the antisense strand (SEQ ID NO:4); the sequence in bold represents the coding sequence; the non-bold sequence represents the non-coding sequence.

FIG. 1E illustrates the nucleotide sequence of the PCR probe used to identify the *Pichia pastoris* FDH gene (SEQ ID NO:25).

FIGS. 1F–1H illustrate the nucleotide and encoded amino acid sequence of the *Gluconobacter oxydans* 2-ketoreductase gene (Examples 3 and Examples 9–15). The bottom line shows the nucleotide sequence (SEQ ID NO:23); the top line shows the amino acid sequence (SEQ ID NO:24). In the nucleotide sequence, "Y"=C+T; "R"=A+G; "I"=deoxyinosine; "M"=A+C; "V"=A+C+G; "B"=C+T+G; "S"=C+G; "D"=A+T+G; "K"=T+G; and "N"=A+T+C+G.

DETAILED DESCRIPTION OF THE INVENTION

Figure 2:
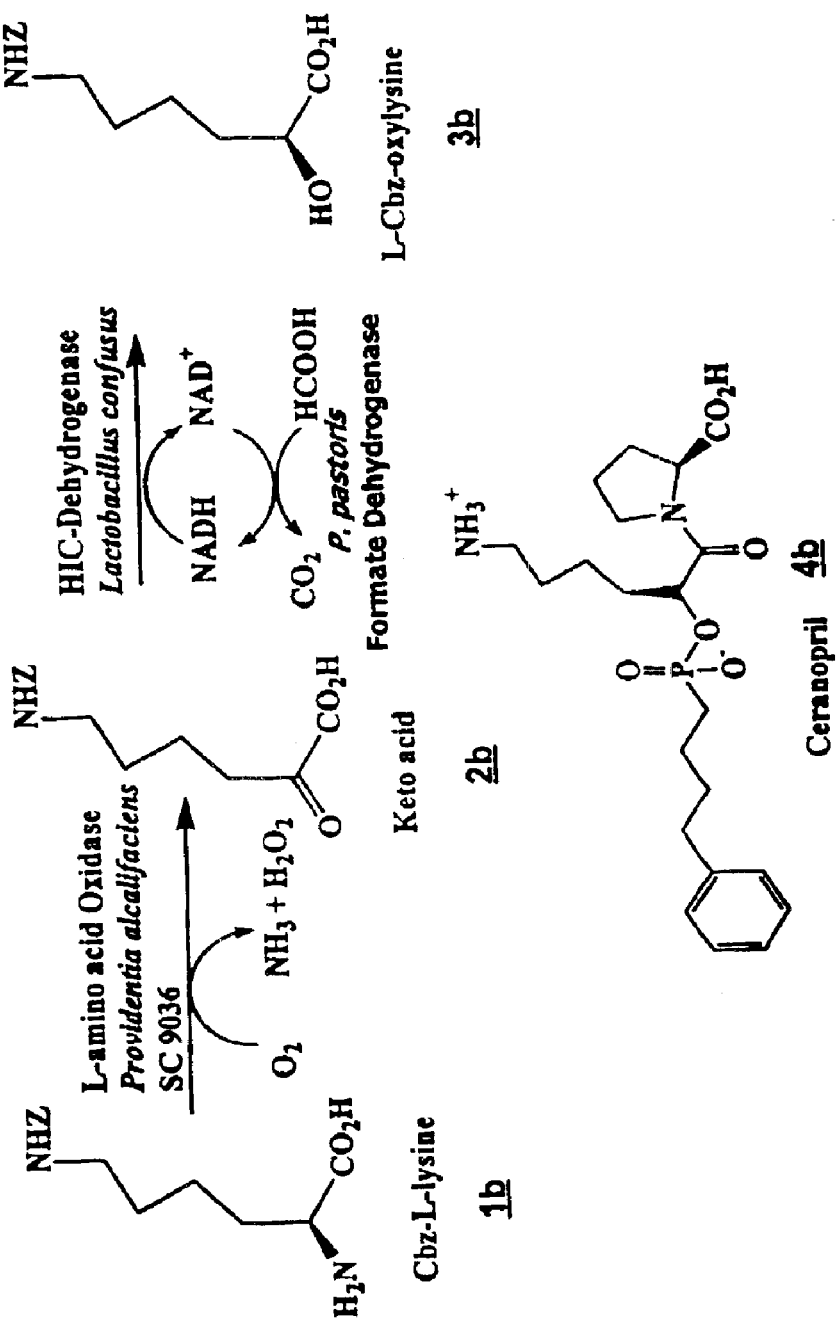
FIG. 2 illustrates the use of *P. pastoris* FDH in the chiral synthon for ceranopril (adapted from R. L. Hanson et al., 1992, *Appl. Microbiol. Biotechnol.* 37:599–603). 1b represents NE-Cbz-L-lysine; 2b represents the corresponding keto acid; 3b represents ceranopril.

The present invention relates to nucleotide sequences that comprise the non-coding and protein-coding regions for a *Pichia pastoris* enzyme with formate dehydrogenase (FDH) activity. The present invention also relates to recombinant proteins or peptides encoded by these regions. Also related are isolated nucleic acids and polypeptides comprising the disclosed sequences, as well as reagents (e.g., probes, primers, vectors, and antibodies) relating to these sequences. The *P. pastoris* nucleic acids and polypeptides of the present invention are useful for various biotechnology and pharmaceutical applications as disclosed in detail herein.

Definitions

Use of the terms "SEQ ID NO:6–SEQ ID NO:15" etc., is intended, for convenience, to refer to each individual SEQ ID NO. individually, and is not intended to refer to the sequences collectively. The invention encompasses each sequence individually, as well as any combination thereof.

"Nucleic acid or "polynucleotide" as used herein refers to purine- and pyrimidine-containing polymers of any length, either polyribonucleotides or polydeoxyribonucleotide or mixed polyribo-polydeoxyribonucleotides. This includes single-and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases. Polynucleotides, e.g., oligonucleotides, include naturally-occurring species or synthetic species formed from naturally-occurring subunits or their close homologs. The term may also refer to moieties that function similarly to polynucleotides, but have non-naturally-occurring portions. Thus, polynucleotides may have altered sugar moieties or inter-sugar linkages. Exemplary among these are phosphorothioate and other sulfur containing species which are known in the art.

A "coding sequence" or a "protein-coding sequence" is a polynucleotide sequence capable of being transcribed into mRNA and/or capable of being translated into a polypeptide. The boundaries of the coding sequence are typically determined by a translation start codon at the 5'-terminus and a translation stop codon at the 3'-terminus.

A "complement" or "complementary sequence" of a nucleic acid sequence as used herein refers to the antisense sequence that participates in Watson-Crick base-pairing with the original sequence.

A "probe" or "primer" refers to a nucleic acid or oligonucleotide that forms a hybrid structure with a sequence in a target region due to complementarily of at least one sequence in the probe or primer with a sequence in the target region.

"Isolated", as used herein, refers to a substantially purified *P. pastoris* FDH molecule (e.g., nucleic acid, polypeptide, peptide, protein fusion, or antibody) that is substantially free of cellular material, culture medium, or other components. Such isolated molecules contain less than 50%, preferably less than 25%, more preferably less than 10%, and most preferably less than 1% of the components with which they were associated.

The term "vector" as used herein refers to a nucleic acid molecule capable of replicating itself and another nucleic acid molecule to which it has been linked. A vector, for example, can be a plasmid, recombinant virus, or transposon.

"Host" includes prokaryotes and eukaryotes. The term includes an organism or cell that is the recipient of a replicable vector.

A "recombinant" *P. pastoris* FDH polypeptide or peptide refers to an amino acid sequence encoded by a *P. pastoris* FDH nucleotide sequence described herein.

As used herein, the terms "protein" and "polypeptide" are synonymous. "Peptides" are defined as fragments or portions of polypeptides, preferably fragments or portions having at least one functional activity (e.g., catalytic or antigenic activity) as the complete polypeptide sequence.

The term "antigenic" refers to the ability of a molecule (e.g., a polypeptide or peptide) to bind to its specific antibody, or an antibody fragment, with sufficiently high affinity to form a detectable antigen-antibody complex.

A "sample" as used herein refers to a biological sample, for example, cells, cell culture media, cell components (e.g., cell membranes or cellular organelles), cell extracts (e.g., cytoplasm, cytosol, or nuclear extracts), as well as samples obtained from, for example, a laboratory procedure.

General descriptions of the foregoing terms and others are known in the art. See, e.g., Roitt et al., 1989, *Immunology*, 2nd Edition, C. V. Mosby Company, New York; Male et al., 1991, *Advanced Immunology*, 2nd Edition, Grower Medical Publishing, New York.

Nucleic Acids

One aspect of the present invention pertains to isolated *P. pastoris* FDH nucleic acids having a nucleotide sequence such as SEQ ID NO:1, SEQ ID NO:2, SEQ ID NO:3, or SEQ ID NO:4, or variants, modifications, or fragments thereof. The nucleic acid molecules of the invention can be DNA or RNA. A preferred nucleic acid is a DNA encoding the *P. pastoris* FDH (SEQ ID NO:5), or fragments or functional equivalents thereof. Such nucleic acids can comprise at least 15, 20, 21, 25, 50, 100, 200, 250, 300, 400, 500, or 1000 contiguous nucleotides.

The term "functional equivalent" is intended to include nucleotide sequences encoding functionally equivalent *P. pastoris* FDH polypeptides. A functional equivalent of a *P. pastoris* FDH polypeptide includes fragments or variants that perform at least one characteristic function of the FDH enzyme (e.g., catalysis or antigenicity). For example, DNA sequence polymorphisms within the nucleotide sequence of a *P. pastoris* FDH polypeptide, especially those within the third base of a codon, may result in "silent" mutations, which do not affect the encoded amino acid sequence of the polypeptide due to the degeneracy of the genetic code.

Preferred embodiments include an isolated nucleic acid sharing at least 60, 70, 77, 80, 85, 90, 95, 99, or 100% sequence identity with a polynucleotide sequence of *P. pastoris* FDH (e.g., SEQ ID NO:1, SEQ ID NO:2, SEQ ID NO:3, or SEQ ID NO:4). This polynucleotide sequence may be identical to the nucleotide sequence of *P. pastoris* FDH (e.g., SEQ ID NO:1, SEQ ID NO:2, SEQ ID NO:3, or SEQ ID NO:4), or may include up to a certain integer number of nucleotide alterations as compared to the reference sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in Lesk, A. M. (Ed.), 1988, *Computational Molecular Biology*, Oxford University Press, New York; Smith, D. W. (Ed.), 1993, *Biocomputing. Informatics and Genome Projects*, Academic Press, New York; Griffin, A. M., and Griffin, H. G. (Eds.), 1994, *Computer Analysis of Sequence Data, Part I*, Humana Press, New Jersey; von Heinje, G., 1987, *Sequence Analysis in Molecular Biology*, Academic Press; Gribskov, M. and Devereux, J. (Eds.), 1991, *Sequence Analysis Primer*, M. Stockton Press, New York; and Carillo, H., and Lipman, D., 1988, SIAM *J. Applied Math.* 48:1073.

For nucleic acids, sequence identity can be determined by comparing a query sequences to sequences in publicly available sequence databases (NCBI) using the BLASTN2 algorithm (S. F. Altschul et al., 1997, *Nucl. Acids Res.*, 25:3389–3402). The parameters for a typical search are: E=0.05, v=50, B=50, wherein E is the expected probability score cutoff, V is the number of database entries returned in the reporting of the results, and B is the number of sequence alignments returned in the reporting of the results (S. F. Altschul et al., 1990, *J. Mol. Biol.*, 215:403–410).

In another approach, nucleotide sequence identity can be calculated using the following equation: % identity= (number of identical nucleotides)/(alignment length in nucleotides)*100. For this calculation, alignment length includes internal gaps but not includes terminal gaps. Alternatively, nucleotide sequence identity can be determined experimentally using the specific hybridization conditions described below.

In accordance with the present invention, nucleic acid alterations are selected from the group consisting of at least one nucleotide deletion, substitution, including transition and transversion, insertion, or modification (e.g., via RNA or DNA analogs, dephosphorylation, methylation, or labeling). Alterations may occur at the 5' or 3' terminal positions of the reference nucleotide sequence or anywhere between those terminal positions, interspersed either individually among the nucleotides in the reference sequence or in one or more contiguous groups within the reference sequence. Alterations of a nucleic acid sequence of *P. pastoris* FDH (e.g., SEQ ID NO:1 or SEQ ID NO:3) may create nonsense, missense, or frameshift mutations in the coding sequence, and thereby alter the polypeptide encoded by the nucleic acid.

The present invention also encompasses naturally-occurring nucleotide polymorphisms of *P. pastoris* FDH (e.g., SEQ ID NO:1, SEQ ID NO:2, SEQ ID NO:3, or SEQ ID NO:4). As will be understood by those in the art, the genomes of all organisms undergo spontaneous mutation in the course of their continuing evolution generating variant forms of gene sequences (Gusella, 1986, *Ann. Rev. Biochem.* 55:831–854). Restriction fragment length polymorphisms (RFLPs) include variations in DNA sequences that alter the length of a restriction fragment in the sequence (Botstein et al., 1980, *Am. J. Hum. Genet.* 32, 314–331). Short tandem repeats (STRs) include tandem di-, tri- and tetranucleotide repeated motifs, also termed variable number tandem repeat (VNTR) polymorphisms.

Single nucleotide polymorphisms (SNPs) are far more frequent than RFLPS, STRs, and VNTRs. SNPs may occur in protein coding (e.g., exon), or non-coding (e.g., intron, 5'UTR, and 3'UTR) sequences. SNPs in protein coding regions may comprise silent mutations that do not alter the amino acid sequence of a protein. Alternatively, SNPs in protein coding regions may produce conservative or non-conservative amino acid changes, described in detail below. In non-coding sequences, SNPs may also result in defective protein expression (e.g., as a result of defective splicing). Other single nucleotide polymorphisms have no phenotypic effects.

Further encompassed by the present invention are nucleic acid molecules that share moderate homology with the *P. pastoris* FDH nucleic acid sequence (e.g., SEQ ID NO:1, SEQ ID NO:2, SEQ ID NO:3, or SEQ ID NO:4), and hybridize to a *P. pastoris* FDH nucleic acid molecule under moderate stringency hybridization conditions. More preferred are nucleic acid molecules that share substantial homology with the *P. pastoris* FDH nucleic acid sequence (e.g., SEQ ID NO:1, SEQ ID NO:2, SEQ ID NO:3, or SEQ ID NO:4) and hybridize to the *P. pastoris* FDH nucleic acid molecules under high stringency hybridization conditions.

As used herein, the phrase "moderate homology" refers to sequences which share at least 60% sequence identity with a FDH sequence (e.g., SEQ ID NO:1, SEQ ID NO:2, SEQ ID NO:3, or SEQ ID NO:4), whereas the phrase "substantial homology" refers to sequences that share at least 90% sequence identity with a FDH sequence. It is recognized, however, that polypeptides and the nucleic acids encoding such polypeptides containing less than the above-described level of homology arising as splice variants or that are modified by conservative amino acid substitutions (or substitution of degenerate codons) are contemplated to be within the scope of the present invention.

The phrase "hybridization conditions" is used herein to refer to conditions under which a double-stranded nucleic acid hybrid is formed from two single nucleic acid strands, and remains stable. As known to those of skill in the art, the stability of the hybrid sequence is reflected in the melting temperature ($T_m$) of the hybrid (see F. M. Ausubel et al.

(Eds.), 1995, *Current Protocols in Molecular Biology*, John Wiley and Sons, Inc., New York, N.Y.). The $T_m$ decreases approximately 0.5° C. to 1.5° C. with every 1% decrease in sequence homology. In general, the stability of a hybrid sequence is a function of the length and guanine/cytosine content of the hybrid, the sodium ion concentration, and the incubation temperature. Typically, the hybridization reaction is initially performed under conditions of low stringency, followed by washes of varying, but higher, stringency. Reference to hybridization stringency relates to such washing conditions.

In accordance with the present invention, "high stringency" conditions can be provided, for example, by hybridization in 50% formamide, 5× Denhardt's solution, 5×SSPE, and 0.2% SDS at 42° C., followed by washing in 0.1×SSPE and 0.1% SDS at 65° C. By comparison, "moderate stringency" can be provided, for example, by hybridization in 50% formamide, 5× Denhardt's solution, 5×SSPE, and 0.2% SDS at 42° C., followed by washing in 0.2×SSPE and 0.2% SDS at 65° C. In addition, "low stringency" conditions can be provided, for example, by hybridization in 10% formamide, 5× Denhardt's solution, 6×SSPE, and 0.2% SDS at 42° C., followed by washing in 1×SSPE and 0.2% SDS at 50° C. It is understood that these conditions may be varied using a variety of buffers and temperatures well known to those skilled in the art.

In a preferred embodiment of the present invention, the nucleic acid is a DNA molecule encoding at least a portion of the *P. pastoris* FDH polypeptide (SEQ ID NO:5). A nucleic acid molecule encoding a FDH polypeptide can be obtained from mRNA present in *Pichia pastoris* cells. It may also be possible to obtain nucleic acid molecules encoding FDH polypeptides from *Pichia pastoris* genomic DNA. In addition, a nucleic acid encoding a *P. pastoris* FDH polypeptide can be cloned from either a cDNA or a genomic library in accordance with the protocols described in detail herein.

Nucleic acids encoding *P. pastoris* FDH enzymes can also be cloned using established polymerase chain reaction (PCR) techniques (see K. Mullis et al., 1986, *Cold Spring Harbor Symp. Quant. Biol.* 51:260; K. H. Roux, 1995, *PCR Methods Appl.* 4:S185) in accordance with the nucleic acid sequence information provided herein. For example, PCR techniques can be used to produce the nucleic acids of the invention, using either RNA (e.g., mRNA) or DNA (e.g., genomic DNA) as templates. Primers used for PCR can be synthesized using the sequence information provided herein and can further be designed to introduce appropriate new restriction sites, if desirable, to facilitate incorporation into a given vector for recombinant expression.

The nucleic acid molecules of the invention, or fragments thereof, can also be chemically synthesized using standard techniques. Various methods of chemically synthesizing polydeoxynucleotides are known, including solid-phase synthesis which, like peptide synthesis, has been fully automated in commercially available DNA synthesizers (see, for example, U.S. Pat. No. 4,598,049 to Itakura et al.; U.S. Pat. No. 4,458,066 to Caruthers et al.; U.S. Pat. Nos. 4,401,796 and 4,373,071 to Itakura).

It will be appreciated by one skilled in the art that variations in one or more nucleotides (up to about 3–4% of the nucleotides) of the nucleic acid molecules encoding a *P. pastoris* FDH polypeptide may exist among organisms within a population due to natural allelic variation. Any and all such nucleotide variations and resulting amino acid polymorphisms are within the scope of the invention. Furthermore, there may be one or more isoforms or related family members of the *P. pastoris* FDH polypeptide described herein. Such isoforms or family members are defined as polypeptides that are related in function and amino acid sequence to a FDH polypeptide (e.g., SEQ ID NO:5), but encoded by genes at different loci. In addition, it is possible to modify the DNA sequence of the FDH gene using genetic techniques to produce proteins or peptides with altered amino acid sequences.

DNA sequence mutations can be introduced into a nucleic acid encoding a *P. pastoris* FDH polypeptide by any one of a number of methods, including those for producing simple deletions or insertions, systematic deletions, insertions or substitutions of clusters of bases or substitutions of single bases, to generate desired variants. Mutations of the *P. pastoris* FDH nucleic acid molecule to generate amino acid substitutions or deletions are preferably obtained by site-directed mutagenesis.

Site directed mutagenesis systems are well known in the art, and can be obtained from commercial sources (see, for example, Amersham-Pharmacia Biotech, Inc., Piscataway, N.J.). Guidance in determining which amino acid residues may be substituted, inserted, or deleted without abolishing biological or immunological activity may be found using computer programs well known in the art, for example, DNASTAR software (DNASTAR, Inc., Madison, Wis.). Mutant forms of the *P. pastoris* FDH nucleic acid molecules are considered within the scope of the present invention, where the expressed polypeptide or peptide is capable catalytic or antigenic activity.

A fragment of the nucleic acid molecule encoding a *P. pastoris* FDH polypeptide is defined as a nucleotide sequence having fewer nucleotides than the nucleotide sequence encoding the entire amino acid sequence of the FDH polypeptide. In one embodiment of the present invention, a nucleic acid molecule corresponding to a fragment of a *P. pastoris* FDH nucleic acid sequence can be used as a probe for assaying a biological sample (e.g., cells or cell extracts) for the expression of one or more FDH nucleic acid sequences, or as a primer for DNA sequencing or PCR amplification. Preferably, such fragments are at least 8, 12, 15, 20, or 21 contiguous nucleotides in length.

In certain embodiments, the nucleic acid molecules of the invention may include linker sequences, modified restriction endonuclease sites, and other sequences useful for molecular cloning, expression, or purification of recombinant protein or fragments thereof. Nucleic acid molecules in accordance with the present invention may also be conjugated with radioisotopes, or chemiluminescent, fluorescent, or other labeling compounds (e.g., digoxigenin). In addition, the nucleic acid molecules of the present invention may be modified by nucleic acid modifying enzymes, for example, kinases or phosphatases. These and other modifications of nucleic acid molecules are well known in the art. In addition, a nucleic acid molecule that encodes a *P. pastoris* FDH polypeptide, or a functional fragment thereof, can be ligated to a heterologous sequence to encode a fusion protein (also called a chimeric protein) as described in detail herein.

Vectors and Host Cells

Another aspect of the present invention pertains to vectors comprising a nucleic acid encoding a *P. pastoris* FDH polypeptide, as described herein, operably linked to at least one regulatory sequence. "Operably linked" is intended to mean that the nucleotide acid sequence is linked to a regulatory sequence in a manner that allows expression of the nucleotide sequence (i.e., production of mRNA and/or amino acid sequences). Regulatory sequences are known in the art and are selected to direct expression of the desired protein in an appropriate host cell or cell-free expression system. Accordingly, the term regulatory sequence includes promoters, enhancers and other expression control elements (see D. V. Goeddel, 1990, *Methods Enzymol.* 185:3–7). It should be understood that the design of the expression vector may depend on such factors as the choice of the host cell or expression system to be utilized and/or the type of polypeptide desired to be expressed.

Suitable expression vectors include, but are not limited to, pUC, pBluescript (Stratagene), pET (Novagen, Inc., Madison, Wis.), as well as pREP, pSE420, and pLEX (Invitrogen). Vectors can contain one or more replication and inheritance systems for cloning or expression, one or more markers for selection in the host, e.g. antibiotic resistance, and one or more expression cassettes. The inserted coding sequences can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods.

Preferred replication and inheritance systems include M13, ColE1, SV40, baculovirus, lambda, adenovirus, CEN ARS, 2 μm, ARS, and the like. Several regulatory elements (e.g., promoters) have been isolated and shown to be effective in the transcription and translation of heterologous proteins in the various hosts. Such regulatory regions, methods of isolation, manner of manipulation, etc. are known in the art. Non-limiting examples of bacterial promoters include the β-lactamase (penicillinase) promoter; lactose promoter; tryptophan (trp) promoter; araBAD (arabinose) operon promoter; lambda-derived $P_1$ promoter and N gene ribosome binding site; and the hybrid tac promoter derived from sequences of the trp and lac UV5 promoters.

Non-limiting examples of yeast promoters include the 3-phosphoglycerate kinase promoter, glyceraldehyde-3-phosphate dehydrogenase (GAFDH or GAP) promoter, galactokinase (GAL1) promoter, galactoepimerase promoter, and alcohol dehydrogenase (ADH1) promoter. Suitable promoters for mammalian cells include, without limitation, viral promoters, such as those from Simian Virus 40 (SV40), Rous sarcoma virus (RSV), adenovirus (ADV), and bovine papilloma virus (BPV). Alternatively, the endogenous *P. pastoris* regulatory elements (e.g., in SEQ ID NO:3) can be used.

Eukaryotic cells may also require terminator sequences, polyadenylation sequences, and enhancer sequences that modulate gene expression. Sequences that cause amplification of the gene may also be desirable. These sequences are well known in the art. Furthermore, sequences that facilitate secretion of the recombinant product from cells, including, but not limited to, bacteria, yeast, and animal cells, such as secretory signal sequences and/or preprotein or proprotein sequences, may also be included in accordance with established methods. Secretory signal sequences are generally positioned 5' to the nucleotide sequence encoding the protein of interest, although certain signal sequences can be positioned 3' to the nucleotide sequence of interest (see, e.g., Welch et al., U.S. Pat. No. 5,037,743; Holland et al., U.S. Pat. No. 5,143,830). Cell-specific secretory signals can be used with certain cell types (e.g., yeast cells).

Expression and cloning vectors will likely contain a selectable marker, a gene encoding a protein necessary for survival or growth of a host cell transformed with the vector. The presence of this gene ensures growth of only those host cells that express the inserts. Typical selection genes encode proteins that 1) confer resistance to antibiotics or other toxic substances, e.g., ampicillin, neomycin, methotrexate, etc.; 2) complement auxotrophic deficiencies, or 3) supply critical nutrients not available from complex media, e.g., the gene encoding D-alanine racemase for Bacilli. Markers may be an inducible or non-inducible gene and will generally allow for positive selection. Non-limiting examples of markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable cell-free expression systems for use with the present invention include, without limitation, rabbit reticulocyte lysate, wheat germ extract, canine pancreatic microsomal membranes, *E. coli* S30 extract, and coupled transcription/translation systems (Promega Corp., Madison, Wis.). Suitable host cells include bacteria, fungi, yeast, plant, insect, and animal, mammalian, and human cells. Specifically included are SF9, C129, 293, NIH 3T3, CHO, COS, HeLa, and Neurospora cells. Insect cell systems (i.e., lepidopteran host cells and baculovirus expression vectors) (Luckow and Summers, 1988, *Biotechnology* 6:47–55) are also included.

Preferred host cells include fungal cells, such as Aspergillus (*A. niger, A. oryzae*, and *A. fumigatus*), *Fusarium venenatum, Schizosaccharomyces pombe, Saccharomyces cerevisiae, Kluyveromyces lactis, Kluyveromyces fragilis, Ustilago maydis, Candida* (e.g., *C. albicans, C. methylica, C. boidinii, C. tropicalis, C. wickerhamii, C. maltosa*, and *C. glabrata*), *Hansenula* (e.g., *H. anomala, H. polymorpha, H. wingei, H. jadinii* and *H. saturnus,*); and *Pichia* (e.g., *P. angusta, P. pastoris, P. anomala, P. stipitis, P. methanolica*, and *P. guilliermondii*) cells. Particularly preferred are bacterial cells, such as *Staphylococcus aureus, Escherichia coli* Bacillus (e.g., *B. licheniformis*, B. amyloliquefaciens, and *B. subtilis*) and *Streptomyces* (e.g., *Streptomyces lividans* and *Streptomyces coelicolor*) cells.

In general, host cells can be transformed, transfected, or infected as appropriate by any suitable method including electroporation, calcium chloride-, lithium chloride-, lithium acetate/polyethylene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, e.g., by injection (see, Kubo et al., 1988, *FEBS Letts.* 241:119).

Methods for transforming *S. cerevisiae* cells with exogenous DNA and producing recombinant proteins therefrom are found in, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; Murray et al., U.S. Pat. No. 4,845,075, and Kawasaki et al., U.S. Pat. No. 4,931,373). Transformation methods for other yeasts, including *H. polymorpha/P. angusta, S. pombe, K. lactis, K. fragilis, U. maydis, P. pastoris, P. methanolica/C. methylica*, and *C. maltosa* are known in the art (see, for example, Gleeson et al., 1986, *J. Gen. Microbiol.* 132:3459–3465; Cregg, U.S. Pat. No. 4,882,279; and Hiep et al., 1993, *Yeast* 9:1189–1197). *Aspergillus* cells can be transformed according to the methods of McKnight et al., U.S. Pat. No. 4,935,349, while *Acremonium chrysogenum* cells can be transformed in accordance with Sumino et al., U.S. Pat. No. 5,162,228. In general, host cells may integrate the nucleic acid molecules of this invention into chromosomal loci. Alternatively, the host cells may maintain the nucleic acid molecules via episomal vectors.

In one embodiment, an expression vector comprises a nucleic acid encoding at least a portion of a P. pastoris FDH polypeptide. In another embodiment, the expression vector comprises a DNA sequence encoding at least a portion of a P. pastoris FDH polypeptide fused in-frame to a DNA sequence encoding a heterologous polypeptide or peptide. Such expression vectors can be used to transfect host cells to thereby produce P. pastoris FDH polypeptides or peptides, including fusion proteins or peptides encoded by nucleic acid molecules as described below.

Several well-established techniques can be used to determine the expression levels and patterns of P. pastoris FDH. For example, mRNA levels can be determined utilizing Northern blot analysis (J. C. Alwine et al., 1977, *Proc. Natl. Acad. Sci. USA* 74:5350–5354; I. M. Bird, 1998, *Methods Mol. Biol.* 105:325–36), whereby poly(A)$^+$ RNA is isolated from cells, separated by gel electrophoresis, blotted onto a support surface (e.g., nitrocellulose or Immobilon-Ny+ (Millipore Corp., Bedford, Mass.)), and incubated with a-labeled (e.g., fluorescently labeled or radiolabeled) oligonucleotide probe that is capable of hybridizing with the mRNA of interest.

Alternatively, mRNA levels can be determined by quantitative (for review, see W.M. Freeman et al., 1999, *Biotechniques* 26:112–122) or semi-quantitative RT-PCR analysis (Ren et al., *Mol. Brain Res.* 59:256–63). In accordance with this technique, poly(A)$^+$ RNA is isolated from cells, used for cDNA synthesis, and the resultant cDNA is incubated with PCR primers that are capable of hybridizing with the template and amplifying the template sequence to produce levels of the PCR product that are proportional to the cellular levels of the mRNA of interest. Another technique, in situ hybridization, can also be used to determine mRNA levels (reviewed by A. K. Raap, 1998, *Mutat. Res.* 400:287–298). In situ hybridization techniques allow the visual detection of mRNA in a cell by incubating the cell with a labeled (e.g., fluorescently labeled or digoxigenin labeled) oligonucleotide probe that hybridizes to the mRNA of interest, and then examining the cell by microscopy.

P. pastoris FDH polypeptides, fragments, modifications, or variants can be also be assessed directly by well-established techniques. For example, host cell expression of the recombinant polypeptides can be evaluated by western blot analysis using antibodies specifically reactive with these polypeptides (see above). Production of secreted forms of the polypeptides can be evaluated by immunoprecipitation using monoclonal antibodies that are specifically reactive the polypeptides. Other, more preferred, assays take advantage of the functional characteristics of the P. pastoris FDH polypeptides. As previously set forth, FDH enzymes can be used in various reactions to regenerate NADH. Thus, the P. pastoris FDH polypeptide function can be assessed by measuring the products of these reactions requiring co-factor regeneration. In specific aspects, any one of the assays described herein can be employed.

Polypeptides

A further aspect of the present invention pertains to isolated P. pastoris FDH polypeptides. The present invention encompasses the P. pastoris FDH polypeptide (e.g., SEQ ID NO:5), and fragments and functional equivalents thereof. Polypeptide fragments (i.e., peptides) can range in size from 5 amino acid residues to all but one residue of the entire amino acid sequence. Thus, a peptide can be at least 5, 15, 20, 25, 30, 50, 100, 200, 236, 250, 300, 500, 800, or more consecutive amino acid residues of a FDH polypeptide. Preferred are polypeptides that share moderate homology with the P. pastoris FDH polypeptide (e.g., SEQ ID NO:5). More preferred are polypeptides that share substantial homology with the P. pastoris FDH polypeptide.

The term "functional equivalent" is intended to include proteins which differ in amino acid sequence from the P. pastoris FDH polypeptide (e.g., SEQ ID NO:5), but where such differences result in a modified protein which performs at least one characteristic function of polypeptide (e.g., catalytic or antigenic activity). For example, a functional equivalent of a P. pastoris FDH polypeptide may have a modification such as a substitution, addition or deletion of an amino acid residue which is not directly involved in the function of this polypeptide. Various modifications of the P. pastoris FDH polypeptide to produce functional equivalents of these polypeptides are described in detail herein.

It is also possible to modify the structure of a P. pastoris FDH polypeptide for such purposes as increasing solubility, enhancing reactivity, or increasing stability (e.g., shelf life ex vivo and resistance to proteolytic degradation in vivo). Such modified proteins are considered functional equivalents of the P. pastoris FDH polypeptide as defined herein. Preferably, P. pastoris FDH polypeptides are modified so that they retain catalytic activity. Those residues shown to be essential for activity can be modified by replacing the essential amino acid with another, preferably similar amino acid residue (a conservative substitution) whose presence is shown to enhance, diminish, but not eliminate, or not effect receptor interaction. In addition, those amino acid residues that are not essential for catalysis can be modified by being replaced by another amino acid whose incorporation may enhance, diminish, or not effect reactivity.

In order to enhance stability and/or reactivity, a P. pastoris FDH polypeptide can be altered to incorporate one or more polymorphisms in the amino acid sequence. Additionally, D-amino acids, non-natural amino acids, or non-amino acid analogs can be substituted or added to produce a modified polypeptide. Furthermore, the polypeptides disclosed herein can be modified using polyethylene glycol (PEG) according to known methods (S. I. Wie et al., 1981, *Int. Arch. Allergy Appl. Immunol.* 64(1):84–99) to produce a protein conjugated with PEG. In addition, PEG can be added during chemical synthesis of the protein. Other possible modifications include phosphorylation, sulfation, reduction/alkylation (Tarr, 1986, *Methods of Protein Microcharacterization*, J. E. Silver, Ed., Humana Press, Clifton, N.J., pp.155–194); acylation (Tarr, supra); chemical coupling (Mishell and Shiigi (Eds.), 1980, *Selected Methods in Cellular Immunology*, W H Freeman, San Francisco, Calif.; U.S. Pat. No. 4,939,239); and mild formalin treatment (Marsh, 1971, *Int. Arch. of Allergy and Appl. Immunol.* 41:199–215).

Modified polypeptides can have conservative changes, wherein a substituted amino acid has similar structural or chemical properties, e.g., replacement of leucine with isoleucine. More infrequently, a modified polypeptide can have non-conservative changes, e.g., substitution of a glycine with a tryptophan. Guidance in determining which amino acid residues can be substituted, inserted, or deleted without abolishing biological or immunological activity can be found using computer programs well known in the art, for example, DNASTAR software (DNASTAR, Inc., Madison, Wis.)

As non-limiting examples, conservative substitutions in P. pastoris FDH amino acid sequence can be made in accordance with the following table:

| Original Residue | Conservative Substitution(s) |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunogenicity can be made by selecting substitutions that are less conservative than those shown in the table, above. For example, non-conservative substitutions can be made which more significantly affect the structure of the polypeptide in the area of the alteration, for example, the alpha-helical, or beta-sheet structure; the charge or hydrophobicity of the molecule at the target site; or the bulk of the side chain. The substitutions which generally are expected to produce the greatest changes in the polypeptide's properties are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

Preferred polypeptide embodiments further include an isolated polypeptide comprising an amino acid sequence sharing at least 60, 70, 80, 85, 86, 90, 95, 97, 98, 99, 99.5 or 100% identity with the amino acid sequence of *P. pastoris* FDH (SEQ ID NO:5). This polypeptide sequence may be identical to the sequence of *P. pastoris* FDH (SEQ ID NO:5), or may include up to a certain integer number of amino acid alterations as compared to the reference sequence Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, *Bioinformatics: Sequence and Genome Analysis*, Cold Spring Harbor Laboratory Press, Cold Spring Harbor, N.Y.). The BLASTP and TBLASTN programs are publicly available from NCBI and other sources. The well-known Smith Waterman algorithm may also be used to determine identity.

Exemplary parameters for amino acid sequence comparison include the following: 1) algorithm from Needleman and Wunsch, 1970, *J Mol. Biol.* 48:443–453; 2) BLOSSUM62 comparison matrix from Hentikoff and Hentikoff, 1992, *Proc. Natl. Acad. Sci. USA* 89:10915–10919; 3) gap penalty=12; and 4) gap length penalty=4. A program useful with these parameters is publicly available as the "gap" program (Genetics Computer Group, Madison, Wis.). The aforementioned parameters are the default parameters for polypeptide comparisons (with no penalty for end gaps). Alternatively, polypeptide sequence identity can be calculated using the following equation: % identity=(the number of identical residues)/(alignment length in amino acid residues)*100. For this calculation, alignment length includes internal gaps but does not include terminal gaps.

In accordance with the present invention, polypeptide sequences may be identical to the sequence of *P. pastoris* FDH (e.g., SEQ ID NO:5), or may include up to a certain integer number of amino acid alterations. Polypeptide alterations are selected from the group consisting of at least one amino acid deletion, substitution, including conservative and non-conservative substitution, or insertion. Alterations may occur at the amino- or carboxy-terminal positions of the reference polypeptide sequence or anywhere between those terminal positions, interspersed either individually among the amino acids in the reference sequence or in one or more contiguous groups within the reference sequence. In specific embodiments, polypeptide variants may be encoded by *P. pastoris* FDH nucleic acids comprising single nucleotide polymorphisms and/or alternate splice variants.

*P. pastoris* FDH polypeptides may also be modified by conjugation with a label capable of providing a detectable signal, either directly or indirectly, including, for example, radioisotopes and fluorescent compounds. Non-limiting examples of fluorescent compounds include Cy3, Cy5, GFP (e.g., EGFP, DsRed, dEFP, etc. (CLONTECH, Palo Alto, Calif.)), Alexa, BODIPY, fluorescein (e.g., FluorX, DTAF, and FITC), rhodamine (e.g., TRITC), auramine, Texas Red, AMCA blue, and Lucifer Yellow. Suitable isotopes include, but are not limited to, $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

The invention also relates to isolated, synthesized and/or recombinant portions or fragments of a *P. pastoris* FDH polypeptide (e.g., SEQ ID NO:5), as described herein. Polypeptide fragments (i.e., peptides) can be made which have full or partial function on their own, or which when mixed together (though fully, partially, or nonfunctional alone), spontaneously assemble with one or more other polypeptides to reconstitute a functional protein having at least one functional characteristic of a *P. pastoris* FDH protein of this invention. In addition, *P. pastoris* FDH polypeptide fragments may comprise, for example, one or more domains of the polypeptide (e.g., NAD-binding and catalytic domains) disclosed herein. Specifically, the NAD-binding and catalytic domains of *P. pastoris* FDH can be used to study the structure/function of the enzyme.

The polypeptides of the present invention, including function-conservative variants, may be isolated from wild-type or mutant *P. pastoris* FDH cells, from heterologous organisms or cells (e.g., bacteria, yeast, insect, plant, or mammalian cells) comprising recombinant *P. pastoris* FDH, or from cell-free translation systems (e.g., wheat germ, microsomal membrane, or bacterial extracts) in which a *P. pastoris* FDH protein-coding sequence has been introduced and expressed. Furthermore, the polypeptides may be part of recombinant fusion proteins. The polypeptides can also, advantageously, be made by synthetic chemistry. Polypeptides may be chemically synthesized by commercially available automated procedures, including, without limitation, exclusive solid phase synthesis, partial solid phase methods, fragment condensation or classical solution synthesis.

Isolation of Polypeptides

Yet another aspect of the present invention pertains to methods of isolating *P. pastoris* FDH polypeptides, or variants, modifications, or fragments thereof from biological samples (e.g., cells, cell extracts or lysates, cell membranes, growth media, etc.). Fragments of FDH polypeptides (i.e., peptides) include portions, preferably, having the same or equivalent function or activity as the full-length polypeptide. Both naturally occurring, synthetic, and recombinant forms of the *P. pastoris* FDH polypeptides or peptides may be used in the methods according to the present invention. Methods for directly isolating and purifying polypeptides or peptides from cellular or extracellular lysates are well known in the art (see E. L. V. Harris and S. Angal (Eds.), 1989, *Protein Purification Methods: A Practical Approach*, IRL Press, Oxford, England). Such methods include, without limitation, preparative disc-gel electrophoresis, isoelectric focusing, high-performance liquid chromatography (HPLC), reversed-phase HPLC, gel filtration, ion exchange and partition chromatography, and countercurrent distribution, and combinations thereof.

In addition, antibody-based methods can be used to isolate natural, synthetic, or recombinantly produced *P. pastoris* FDH polypeptides or peptides. Antibodies that recognize these polypeptides, or peptides derived therefrom, can be produced and isolated using methods known and practiced in the art (see below). *P. pastoris* FDH polypeptides or peptides can then be purified from a crude lysate by chromatography on antibody-conjugated solid-phase matrices (see E. Harlow and D. Lane, 1999, *Using Antibodies: A Laboratory Manual*, Cold Spring Harbor Laboratory, Cold Spring Harbor, N.Y.). Other isolation methods known and used in the art may also be employed.

To produce recombinant *P. pastoris* FDH polypeptides or peptides, DNA sequences encoding the polypeptides or peptides can be cloned into a suitable vector for expression in intact host cells or in cell-free translation systems as described above (see also J. Sambrook et al., 1989, *Molecular Cloning: A Laboratory Manual*, 2d Ed., Cold Spring Harbor Laboratory Press, Cold Spring Harbor, N.Y.). DNA sequences can be optimized, if desired, for more efficient expression in a given host organism. For example, codons can be altered to conform to the preferred codon usage in a given host cell or cell-free translation system using techniques routinely practiced in the art.

For some purposes, it may be preferable to produce *P. pastoris* FDH peptides or polypeptides in a recombinant system wherein the peptides or polypeptides carry additional sequence tags to facilitate purification. Such markers include epitope tags and protein tags. Non-limiting examples of epitope tags include c-myc, haemagglutinin (HA), polyhistidine (6X-HIS), GLU-GLU, and DYKDDDDK (FLAG®) epitope tags. Non-limiting examples of protein tags include glutathione-S-transferase (GST), green fluorescent protein (GFP), and maltose binding protein (MBP).

Epitope and protein tags can be added to peptides by a number of established methods. For example, DNA sequences encoding epitope tags can be inserted into protein-coding sequences as oligonucleotides or as primers used in PCR amplification. As an alternative, protein-coding sequences can be cloned into specific vectors that create fusions with epitope tags; for example, pRSET vectors (Invitrogen Corp., San Diego, Calif.). Similarly, protein tags can be added by cloning the coding sequence of a polypeptide or peptide into a vector that creates a fusion between the polypeptide or peptide and a protein tag of interest. Suitable vectors include, without limitation, the exemplary plasmids, pGEX (Amersham-Pharmacia Biotech, Inc., Piscataway, N.J.), pEGFP (CLONTECH Laboratories, Inc., Palo Alto, Calif.), and pMAL™ (New England BioLabs, Inc., Beverly, Mass.). Following expression, the epitope or protein tagged polypeptide or peptide can be purified from a crude lysate of the translation system or host cell by chromatography on an appropriate solid-phase matrix. In some cases, it may be preferable to remove the epitope or protein tag (i.e., via protease cleavage) following purification.

In various embodiments, the recombinant *P. pastoris* FDH polypeptides are secreted to the cell surface, retained in the cytoplasm of the host cells, or secreted into the growth media. In each case, the production of *P. pastoris* FDH polypeptides can be established using anti-FDH antibodies, or catalytic assays. The cell-surface and cytoplasmic recombinant *P. pastoris* FDH polypeptides can be isolated following cell lysis and extraction of cellular proteins, while the secreted recombinant *P. pastoris* FDH polypeptides can be isolated from the cell growth media by standard techniques (see I. M. Rosenberg (Ed.), 1996, *Protein Analysis and Purification: Benchtop Techniques*, Birkhauser, Boston, Cambridge, Mass.).

Methods to improve polypeptide production may include 1) the use of bacterial expressed fusion proteins comprising signal peptides or targeting sequences to promote secretion (Tessier et al., 1991, *Gene* 98:177–83; Gamier et al., 1995, *Biotechnology* 13:1101–4); 2) the use of serum-free and protein-free culture systems for economical polypeptide production (Zang et al., 1995, *Biotechnology* 13:389–92); 3) the use of the eukaryotic regulated secretory pathway for increased production and harvesting efficiency (see Chen et al., 1995, *Biotechnology* 13:1191–97). Polypeptide production may also be optimized by the utilization of a specific vector, host cell, expression system, or production protocol, as described in detail herein.

Large-scale microbial protein production can be achieved using well-established methods (see, e.g., W. Crueger and A. Crueger, 1990, *Biotechnology: A Textbook of Industrial Microbiology* Sinauer Associates, Sunderland, M. A.; A. N. Glazer and H. Nikaido, 1995, *Microbial biotechnology: fundamentals of applied microbiology* Freeman, New York, N.Y.; C. M. Brown et al., 1987, *Introduction to Biotechnology: Basic Microbiology*, Vol. 10, Blackwell, Oxford, UK). Methods for scaling-up baculovirus protein production can be found, for example, in R. L. Tom et al., 1995, *Methods Mol. Biol.* 39:203–24; R. L. Tom et al., 1995, *Appl. Microbiol. Biotechnol.* 44:53–8; S. A. Weiss, et al., 1995, *Methods Mol. Biol.* 39:79–95; and C. D. Richardson (Ed.), 1995, *Baculovirus Expression Protocols: Methods in Molecular Biology*, Vol. 39, Humana Press, Totowa, N.J. In additional, large-scale protein production services are commercially available from, e.g., PanVera Corp., Madison, Wis.; Oxford Expression Technologies, Oxford UK; BioXpress Laboratory, Athens, Ga.; and Recombinant Protein Expression Laboratory, Gainesville, Fla.

In general, large-scale microbial enzyme production systems employ the following procedures. Screens are used to test enzyme activity, pH optimum, temperature optimum, secretion (downstream processing), and the ability to grow the organism in inexpensive large-scale fermentation systems (high population densities from inexpensive carbon and nitrogen feedstocks, e.g., corn syrup, molasses, soybean meal, gluten, etc.). Strain improvements are created by random mutagenesis and screening or directed genetic manipulation (e.g., in *Bacillus*, *Streptomyces*, *Aspergillus* and *Saccharomyces* strains). For example, mutant strains can provide 1) relief of repression (e.g., catabolite repression); 2) increased promoter strength; 3) higher affinity ribosome-binding sites; 4) higher efficiency of mRNA leader translation; 5) increased mRNA half life; 6) increased translation efficiency through altered codon usage; 7)

improvement of secretion efficiency; and 8) increased gene dosage (i.e., via chromosomal amplification or plasmid amplification). Process improvements are implemented by screening feeding strategies (e.g., batch, fed-batch, continuous, or recycle), reactor configurations, stirring methods (e.g., via impeller, bubble, air lift, packed bed, solid state, or hollow fiber), pH control, foam, and temperature. Enzymes produced by exemplary large-scale microbial systems include various serine proteinases, Zn metalloproteinases, aspartic proteinases, isomerases, pectinases, lipases, α-amylase, cellases, and glucomylases.

Uses for Polypeptides

The isolated *P. pastoris* FDH polypeptides, peptides, modifications, or variants thereof, are useful for regenerating co-factor (e.g., NADH) for various biosynthetic or pharmaceutical applications. In various aspects, *P. pastoris* FDH can be used in reduction reactions involving ketones (e.g., 2-pentanone, N-P-α-amino chloroketone, and ketoacid acetal), and can also be used in the synthesis of amino acids, chiral hydroxy acids, ethers, alcohols, and other chemical species (see below). In addition, *P. pastoris* FDH can be used in the preparation of chiral synthons, e.g., with substrates 4-chloro-3-oxo-butanoic acid, α-keto-β-hydroxyisovalerate, N-protected α-aminochloroketone and the keto acid of Nε-Cbz-L-lysine, as described in detail herein. *P. pastoris* FDH can also be employed in reduction amination reactions in the synthesis of tert-leucine (3-methylvaline; tert-butyl glycine) in accordance with established methods (A. S. Bommarius et al., 1995, *Tetrahedron: Asymmetry* 8:2547–2552). Further, *P. pastoris* FDH can be employed in conjunction with dehydrogenases (e.g., L-alanine dehydrogenase, L-leucine dehydrogenase, L-phenylalanine dehydrogenase, hydroxy acid dehydrogenases, 2-hydroxy acid dehydrogenases, alcohol dehydrogenases, and diketone reductases) for the synthesis of compounds, especially chiral compounds (see W. Hummel and M.-R. Kula, 1989, *Eur. J. Biochem.* 184:1–13). In particular, *P. pastoris* FDH can be utilized in reactions with leucine dehydrogenase and α-keto-β-hydroxyisovalerate substrate, as described herein below.

In preferred embodiments, the products of reactions involving *P. pastoris* FDH are useful as intermediates for the synthesis of therapeutics or other beneficial compounds. For example, S(−)-4-chloro-3-hydroxy-butanoic acid, produced by reduction of β-keto esters of 4-chloro-3-oxo-butanoic acid, can be used to synthesize HMG-CoA reductase inhibitor (R. N. Patel et al., 1992, *Enzyme Microb. Technol.* 14:731–738). L-Cbz-oxolysine, produced by oxidation of Nε-Cbz-L-lysine and reduction of the resulting keto acid, can be used to synthesize ceranopril (R. L. Hanson et al., 1992, *Appl. Microbiol. Biotechnol.* 37:599–603), a angiotensin converting enzyme inhibitor developed for the treatment of hypertension (D. S. Karenewsky et al., 1988, *J. Med. Chem.* 31:204–212). Allysine ethylene acetal, produced by reductive amination of ketoacid acetal, can be used to synthesize VANLEV (R. L. Hanson et al., 2000, *Enzyme Microb. Technol.* 26:348–358; U.S. Pat. No. 6,140,088 to Hanson et al.; U.S. Pat. No. 6,162,913 to Moniot et al.; U.S. Pat. No. 6,261,810 B1 to Patel et al.), a vasopeptidase inhibitor (J. A. Robl et al., 1997, *J. Med. Chem.* 40:1570–1577).

Further, L-β-hydroxyvaline, produced by conversion of β-keto-β-hydroxyisovalerate, can be used in the synthesis of tigemonam (R. L. Hanson et al., 1990, *Bioorgan. Chem.* 18:116–130), an orally active monobactam antibiotic (E. M. Gordon et al., 1982, *J. Amer. Chem. Soc.* 104:6053–6060; W. L. Parker et al., 1988, *Chem. Abstr.* 109:116074a; U.S. Pat. No. 4,751,220; W. H. Koster et al., 1985, *25th Intersci. Conf.* *Antimicrobial Agents and Chemotherapy*, Abstract 368, September; W. A. Slusarchyk et al., 1986, *Tetrahedron Lett.* 27:2789–2792; C. Yoshida et al., 1985, *J. Antibiot.* 38:1536–1549). Chiral intermediate 3-chloro-2-hydroxy-1-(phenymethyl)propyl carbamic acid, 1-1 dimethylester, produced by reduction of N-protected α-aminochloroketone (R. N. Patel et al., 1997, *Tetrahedron: Asymmetry* 8:2547–2552), can be used in the preparation of a HIV protease inhibitor (J. C. Barrish et al., 1994, *J. Med. Chem.* 37:1758–1771). Chiral hydroxy acids, produced from 2-oxy acids (W. Hummel and M.-R. Kula, 1989, *Eur. J. Biochem.* 184:1–13), can be used in the production of pharmaceuticals, including semisynthetic penicillins (U.S. Pat. No. 3,957,758), cephalosporins, (Ger. Offen. 251492), and anti-obesity compounds (U.S. Pat. No. 4,391,826).

In addition, tert-leucine can be used as a component in the synthesis of HIV-protease inhibitors (EP 560269; A. K. Gosh et al., 1993, *J. Med. Chem.* 36:2300–2310; E. De Clercq, 1995, *J. Med. Chem.* 38:2491–2517; EP 0432695; T. F. Tam et al., 1992, *J. Med. Chem.* 35:1318–1320; EP 0490667; R. Kato et al., 1994, *Chem. Pharm. Bull.* 42:176–178; P. Ettmayer et al., 1994, *Bioorg. Med. Chem. Lett.* 4:2851–2856; Pat. Appl. EP 486948); anti-arthritic agents (Pat. Appl. EP 0497192); anti-HSV agents (P. Ettmayer et al., 1994, *Bioorg. Med. Chem. Lett.* 4:2851–2856; Pat. Appl. EP 0560274); gelatinase inhibitors (WO 93/24449); thymidylate synthase inhibitors (EP 0284338; T. Spector et al., 1991, *Biochem. Pharmacol.* 42:91–96); and anti-tumor peptides (N. K. Gulavita et al., 1992, *J. Org. Chem.* 57:1767–1772).

In other embodiments, the *P. pastoris* FDH of the invention can be used in enzymatic assays for serum formate levels following methanol poisoning, in accordance with available methods (S. Grady and J. Osterloh, 1986, *J. Analyt. Toxicol.* 10:1–5). *P. pastoris* FDH can also be used with dehydrogenases that are employed for wide-ranging applications in clinical and food-related fields (described by H. U. Bergmeyer, 1985, *Methods in Enzymatic Analysis*, Verlag Chemie, Weinheim). *P. pastoris* FDH can also be used in the synthesis of key components for insecticides (S.-Y. Wu et al., 1987, *J. Pesticide Sci.* 12:221–227).

For use in medical or industrial applications, *P. pastoris* FDH polypeptides, peptides, modifications, or variants thereof can be added to a particular chemical reaction by any available means. For example, *P. pastoris* FDH isolated from natural (e.g., *P. pastoris* cells), recombinant, or synthetic sources may be used. Alternatively, cell extracts or whole cells expressing a secreted form of *P. pastoris* FDH may be used. Different sources of *P. pastoris* FDH can be compared to determine the *P. pastoris* FDH source that results in, for example, the highest yields of product or the lowest production costs. Notably, recombinant production of *P. pastoris* FDH is expected to have lower production costs and time requirements than required for the purification of the native *P. pastoris* FDH enzyme.

Antibodies

Another aspect of the invention pertains to antibodies directed to *P. pastoris* FDH polypeptides, or portions or variants thereof. The invention provides polyclonal and monoclonal antibodies that bind *P. pastoris* FDH polypeptides or peptides. The antibodies may be elicited in an animal host (e.g., non-human mammal) by immunization with enzyme components. Antibodies may also be elicited by in vitro immunization (sensitization) of immune cells. The immunogenic components used to elicit the production of antibodies may be isolated from cells or chemically synthesized. The antibodies may also be produced in recombinant systems programmed with appropriate antibody-encoding DNA. Alternatively, the antibodies may be constructed by biochemical reconstitution of purified heavy and light chains. The antibodies include hybrid antibodies, chimeric antibodies, and univalent antibodies. Also included are Fab fragments, including $Fab_1$ and $Fab(ab)_2$ fragments of antibodies.

In accordance with the present invention, antibodies are directed to a *P. pastoris* FDH polypeptide (e.g., SEQ ID NO:5), or variants, or portions thereof. For example, antibodies can be produced to bind to a *P. pastoris* FDH polypeptide encoded by an alternate splice variant or SNP variant of SEQ ID NO:1, SEQ ID NO:2, SEQ ID NO:3, or SEQ ID NO:4. An isolated *P. pastoris* FDH polypeptide (e.g., SEQ ID NO:5), or variant, or portion thereof, can be used as an immunogen to generate antibodies using standard techniques for polyclonal and monoclonal antibody preparation. A full-length *P. pastoris* FDH polypeptide can be used or, alternatively, the invention provides antigenic peptide portions of the polypeptide for use as immunogens. An antigenic peptide comprises at least 5 contiguous amino acid residues, preferably at least 32 contiguous amino acid residues, of the amino acid sequence shown in SEQ ID NO:5, or a variant thereof, and encompasses an epitope of a *P. pastoris* FDH polypeptide such that an antibody raised against the peptide forms a specific immune complex with a *P. pastoris* FDH amino acid sequence.

An appropriate immunogenic preparation can contain, for example, recombinantly produced *P. pastoris* FDH polypeptide or a chemically synthesized polypeptide, or portions thereof. The preparation can further include an adjuvant, such as Freund's complete or incomplete adjuvant, or similar immunostimulatory agent. A number of adjuvants are known and used by those skilled in the art. Non-limiting examples of suitable adjuvants include incomplete Freund's adjuvant, mineral gels such as alum, aluminum phosphate, aluminum hydroxide, aluminum silica, and surface-active substances such as lysolecithin, pluronic polyols, polyanions, peptides, oil emulsions, keyhole limpet hemocyanin, and dinitrophenol. Further examples of adjuvants include N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-Lalanyl-D-isoglutaminyl-L-alanine-2-(1'-2'-dipalmitoyl-sn-glycero-3 hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. A particularly useful adjuvant comprises 5% (wt/vol) squalene, 2.5% Pluronic L121 polymer and 0.2% polysorbate in phosphate buffered saline (Kwak et al., 1992, *New Eng. J. Med.* 327:1209–1215). Preferred adjuvants include complete BCG, Detox, (RIBI, Immunochem Research Inc.), ISCOMS, and aluminum hydroxide adjuvant (Superphos, Biosector). The effectiveness of an adjuvant may be determined by measuring the amount of antibodies directed against the immunogenic peptide.

Polyclonal antibodies to *P. pastoris* FDH polypeptides can be prepared as described above by immunizing a suitable subject (e.g., horse, donkey, goat, rabbit, rat, mouse, chicken, or other non-human animal) with a *P. pastoris* FDH immunogen. The antibody titer in the immunized subject can be monitored over time by standard techniques, such as with an enzyme linked immunosorbent assay (ELISA) using immobilized *P. pastoris* FDH polypeptide or peptide. If desired, the antibody molecules can be isolated from the mammal (e.g., from the blood) and further purified by well-known techniques, such as protein A chromatography to obtain the IgG fraction.

At an appropriate time after immunization, e.g., when the antibody titers are highest, antibody-producing cells can be obtained from the subject and used to prepare monoclonal antibodies by standard techniques, such as the hybridoma technique (see Kohler and Milstein, 1975, *Nature* 256:495–497; Brown et al., 1981, *J. Immunol.* 127:539–46; Brown et al., 1980, *J. Biol. Chem.* 255:4980–83; Yeh et al., 1976, *PNAS* 76:2927–31; and Yeh et al., 1982, *Int. J. Cancer* 29:269–75), the human B cell hybridoma technique (Kozbor et al., 1983, *Immunol. Today* 4:72), the EBV-hybridoma technique (Cole et al., 1985, *Monoclonal Antibodies and Cancer Therapy*, Alan R. Liss, Inc., pp. 77–96) or trioma techniques.

The technology for producing hybridomas is well-known (see generally R. H. Kenneth, 1980, *Monoclonal Antibodies: A New Dimension In Biological Analyses*, Plenum Publishing Corp., New York, N.Y.; E. A. Lerner, 1981, *Yale J. Biol. Med.*, 54:387–402; M. L. Gefter et al., 1977, *Somatic Cell Genet.* 3:231–36). In general, an immortal cell line (typically a myeloma) is fused to lymphocytes (typically splenocytes) from a mammal immunized with a *P. pastoris* FDH immunogen as described above, and the culture supernatants of the resulting hybridoma cells are screened to identify a hybridoma producing a monoclonal antibody that binds *P. pastoris* FDH polypeptides or peptides.

Any of the many well known protocols used for fusing lymphocytes and immortalized cell lines can be applied for the purpose of generating an monoclonal antibody to a *P. pastoris* FDH polypeptide (see, e.g., G. Galfre et al., 1977, *Nature* 266:55052; Gefter et al., 1977; Lerner, 1981; Kenneth, 1980). Moreover, the ordinarily skilled worker will appreciate that there are many variations of such methods. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin, and thymidine (HAT medium). Any of a number of myeloma cell lines can be used as a fusion partner according to standard techniques, e.g., the P3-NS1/1-Ag4-1, P3-x63-Ag8.653, or Sp2/O-Ag14 myeloma lines. These myeloma lines are available from ATCC (American Type Culture Collection, Manassas, Va.). Typically, HAT-sensitive mouse myeloma cells are fused to mouse splenocytes using polyethylene glycol (PEG). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind *P. pastoris* FDH polypeptides or peptides, e.g., using a standard ELISA assay.

Alternative to preparing monoclonal antibody-secreting hybridomas, a monoclonal antibody can be identified and isolated by screening a recombinant combinatorial immunoglobulin library (e.g., an antibody phage display library) with the corresponding *P. pastoris* FDH polypeptide to thereby isolate immunoglobulin library members that bind the polypeptide. Kits for generating and screening phage display libraries are commercially available (e.g., the Pharmacia Recombinant Phage Antibody System, Catalog No.

27-9400-01; and the Stratagene SurfZAP™ Phage Display Kit, Catalog No. 240612).

Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al., 1991, *Bio/Technology* 9:1370–1372; Hay et al., 1992, *Hum. Antibod. Hybridomas* 3:81–85; Huse et al., 1989, *Science* 246:1275–1281; Griffiths et al., 1993, *EMBO J* 12:725–734; Hawkins et al., 1992, *J. Mol. Biol.* 226:889–896; Clarkson et al., 1991, *Nature* 352:624–628; Gram et al., 1992, *PNAS* 89:3576–3580; Garrad et al., 1991, *Bio/Technology* 9:1373–1377; Hoogenboom et al., 1991, *Nuc. Acid Res.* 19:4133–4137; Barbas et al., 1991, *PNAS* 88:7978–7982; and McCafferty et al., 1990, *Nature* 348:552–55.

Additionally, recombinant antibodies to a *P. pastoris* FDH polypeptide, such as chimeric monoclonal antibodies, can be made using standard recombinant DNA techniques. Such chimeric monoclonal antibodies can be produced by recombinant DNA techniques known in the art, for example using methods described in Robinson et al. International Application No. PCT/US86/02269; Akira, et al. European Patent Application 184, 187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125, 023; Better et al., 1988, *Science* 240:1041–1043; Liu et al., 1987, *PNAS* 84:3439–3443; Liu et al., 1987, *J. Immunol.* 139:3521–3526; Sun et al., 1987, *PNAS* 84:214–218; Nishimura et al., 1987, *Canc. Res.* 47:999–1005; Wood et al., 1985, *Nature* 314:446–449; and Shaw et al., 1988, *J. Natl. Cancer Inst.* 80:1553–1559; S. L. Morrison, 1985, *Science* 229:1202–1207; Oi et al., 1986, *BioTechniques* 4:214; Winter U.S. Pat. No. 5,225,539; Jones et al., 1986, *Nature* 321:552–525; Verhoeyan et al., 1988, *Science* 239:1534; and Beidler et al., 1988, *J. Immunol.* 141:4053–4060.

An antibody against a *P. pastoris* FDH polypeptide (e.g., monoclonal antibody) can be used to isolate the corresponding polypeptide by standard techniques, such as affinity chromatography or immunoprecipitation. For example, antibodies can facilitate the purification of a natural *P. pastoris* FDH polypeptide from cells and of a recombinantly produced *P. pastoris* FDH polypeptide or peptide expressed in host cells. In addition, an antibody that binds to a *P. pastoris* FDH polypeptide can be used to detect the corresponding protein (e.g., in a cell, cellular lysate, or cell supernatant) in order to evaluate the abundance, localization, or pattern of expression of the protein. Detection methods employing antibodies include well-established techniques, such as Western blot, dot blot, colony blot, ELISA, immunocytochemical, and immunohistochemical analysis.

Modulators

The *P. pastoris* FDH polypeptides, polynucleotides, variants, or fragments thereof, can be used to screen for test agents (e.g., agonists, antagonists, inhibitors, or other modulators) that alter the levels or activity of the corresponding *P. pastoris* FDH polypeptide. In addition, these *P. pastoris* FDH molecules can be used to identify endogenous modulators that bind to polypeptides or polynucleotides in the *P. pastoris* cell. In one aspect of the present invention, the full-length *P. pastoris* FDH polypeptide (e.g., SEQ ID NO:5) is used to identify modulators. Alternatively, variants or fragments of a *P. pastoris* FDH polypeptide are used. Such fragments may comprise, for example, one or more domains of the *P. pastoris* FDH polypeptide (e.g., the NAD-binding and catalytic domains) disclosed herein. A wide variety of assays may be used for these screens, including in vitro protein-protein binding assays, electrophoretic mobility shift assays, immunoassays, and the like.

The term "modulator" as used herein describes any test agent, molecule, protein, peptide, or compound with the capability of directly or indirectly altering the physiological function, stability, or levels of a *P. pastoris* FDH polypeptide. Modulators that bind to *P. pastoris* FDH polypeptides or polynucleotides of the invention are potentially useful in biotechnology or pharmaceutical applications, as described in detail herein. Test agents that are useful as modulators may encompass numerous chemical classes, though typically they are organic molecules, preferably small organic compounds having a molecular weight of more than 50 and less than about 2,500 daltons. Such molecules can comprise functional groups necessary for structural interaction with proteins, particularly hydrogen bonding, and typically include at least an amine, carbonyl, hydroxyl or carboxyl group, preferably at least two of the functional chemical groups. Test agents which can be used as modulators often comprise cyclical carbon or heterocyclic structures and/or aromatic or polyaromatic structures substituted with one or more of the above functional groups. Test agents can also comprise biomolecules including peptides, saccharides, fatty acids, steroids, purines, pyrimidines, derivatives, structural analogs, or combinations thereof.

Test agents finding use as modulators may include, for example, 1) peptides such as soluble peptides, including Ig-tailed fusion peptides and members of random peptide libraries (see, e.g., Lam et al., 1991, *Nature* 354:82–84; Houghten et al., 1991, *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang et al, (1993) *Cell* 72:767–778); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules.

Test agents and modulators can be obtained from a wide variety of sources including libraries of synthetic or natural compounds. Synthetic compound libraries are commercially available from, for example, Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich Chemical Company, Inc. (Milwaukee, Wis.). Natural compound libraries comprising bacterial, fungal, plant or animal extracts are available from, for example, Pan Laboratories (Bothell, Wash.). In addition, numerous means are available for random and directed synthesis of a wide variety of organic compounds and biomolecules, including expression of randomized oligonucleotides.

Alternatively, libraries of natural compounds in the form of bacterial, fungal, plant and animal extracts can be readily produced. Methods for the synthesis of molecular libraries are readily available (see, e.g., DeWitt et al., 1993, *Proc.*

Natl. Acad. Sci. USA 90:6909; Erb et al., 1994, *Proc. Natl. Acad. Sci. USA* 91:11422; Zuckermann et al., 1994, *J. Med. Chem.* 37:2678; Cho et al., 1993, *Science* 261:1303; Carell et al., 1994, *Angew. Chem. Int. Ed. Engl.* 33:2059; Carell et al., 1994, *Angew. Chem. Int Ed. Engl.* 33:2061; and in Gallop et al., 1994, *J. Med. Chem.* 37:1233). In addition, natural or synthetic compound libraries and compounds can be readily modified through conventional chemical, physical and biochemical means (see, e.g., Blondelle et al., 1996, *Trends in Biotech.* 14:60), and may be used to produce combinatorial libraries. In another approach, previously identified pharmacological agents can be subjected to directed or random chemical modifications, such as acylation, alkylation, esterification, amidification, and the analogs can be screened for *P. pastoris* FDH-modulating activity.

Numerous methods for producing combinatorial libraries are known in the art, including those involving biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer, or small molecule libraries of compounds (K. S. Lam, 1997, *Anticancer Drug Des.* 12:145).

Libraries may be screened in solution (e.g., Houghten, 1992, *Biotechniques* 13:412–421), or on beads (Lam, 1991 *Nature* 354:82–84), chips (Fodor, 1993 *Nature* 364:555–556), bacteria or spores (Ladner U.S. Pat. No. 5,223,409), plasmids (Cull et al., 1992 *Proc. Natl. Acad. Sci. USA* 89:1865–1869), or on phage (Scott and Smith, 1990, *Science* 249:386–390; Devlin, 1990, *Science* 249:404–406; Cwirla et al., 1990, *Proc. Natl. Acad. Sci. USA* 97:6378–6382; Felici, 1991, *J. Mol. Biol.* 222:301–310; Ladner, supra).

Where the screening assay is a binding assay, a *P. pastoris* FDH polypeptide, polynucleotide, analog, or fragment thereof, may be joined to a label, where the label can directly or indirectly provide a detectable signal. Various labels include radioisotopes, fluorescers, chemiluminescers, enzymes, specific binding molecules, particles, e.g. magnetic particles, and the like. Preferred fluorescent labels include, for example, Cy3, Cy5, GFP (e.g., EGFP, DsRed, dEFP, etc. (CLONTECH, Palo Alto, Calif.)), Alexa, BODIPY, fluorescein (e.g., FluorX, DTAF, and FITC), rhodamine (e.g., TRITC), auramine, Texas Red, AMCA blue, and Lucifer Yellow. Preferred isotope labels include $^{3}$H, $^{14}$C, 32P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re. Non-limiting examples of enzyme labels include peroxidase, β-glucuronidase, β-D-glucosidase, β-D-galactosidase, urease, glucose oxidase plus peroxidase, and alkaline phosphatase (see, e.g., U.S. Pat. Nos. 3,654,090; 3,850,752 and 4,016,043). Enzymes can be conjugated by reaction with bridging molecules such as carbodiimides, diisocyanates, glutaraldehyde, and the like. Enzyme labels can be detected visually, or measured by calorimetric, spectrophotometric, fluorospectrophotometric, amperometric, or gasometric techniques. Other labeling systems, such as avidin/biotin, Tyramide Signal Amplification (TSA™), and digoxin/anti-digoxin, are known in the art, and are commercially available (see, e.g., ABC kit, Vector Laboratories, Inc., Burlingame, Calif.; NEN® Life Science Products, Inc., Boston, Mass.). For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc., that are used to facilitate optimal protein-protein binding and/or reduce non-specific or background interactions. Reagents that improve the efficiency of the assay, such as protease inhibitors, nuclease inhibitors, anti-microbial agents, etc., may be used. The components are added in any order that produces the requisite binding. Incubations are performed at any temperature that facilitates optimal activity, typically between 4° and 40° C. Incubation periods are selected for optimum activity, but may also be optimized to facilitate rapid high-throughput screening. Normally, between 0.1 and 1 hr will be sufficient. In general, a plurality of assay mixtures is run in parallel with different agent concentrations to obtain a differential response to these concentrations. Typically, one of these concentrations serves as a negative control, i.e. at zero concentration or below the level of detection.

To perform cell-free screening assays, it may be desirable to immobilize either the *P. pastoris* FDH polypeptide, polynucleotide, variant, or fragment to a surface to facilitate identification of modulators that bind to these molecules, as well as to accommodate automation of the assay. For example, a fusion protein comprising a *P. pastoris* FDH polypeptide and an affinity-tag can be produced as described in detail herein. In one embodiment, a GST-fusion protein comprising a *P. pastoris* FDH polypeptide is adsorbed onto glutathione sepharose beads (Sigma Chemical, St. Louis, Mo.) or glutathione-derivatized microtiter plates. Cell lysates (e.g., containing $^{35}$S-labeled polypeptides) are added to the polypeptide-coated beads under conditions to allow complex formation (e.g., at physiological conditions for salt and pH). Following incubation, the polypeptide-coated beads are washed to remove any unbound polypeptides, and the amount of immobilized radiolabel is determined. Alternatively, the complex is dissociated and the radiolabel present in the supernatant is determined. In another approach, the beads are analyzed by SDS-PAGE to identify *P. pastoris* FDH-binding polypeptides.

Various binding assays can be used to identify modulators that alter the function or levels of a *P. pastoris* FDH polypeptide. Such assays are designed to detect the interaction of test agents with *P. pastoris* FDH polypeptides, polynucleotides, variants, or fragments thereof. Interactions may be detected by direct measurement of binding. Non-limiting examples of useful binding assays are detailed as follows. Modulators that bind to *P. pastoris* FDH polypeptides, polynucleotides, functional equivalents, or fragments thereof, can be identified using real-time Bimolecular Interaction Analysis (BIA; Sjolander et al., 1991, *Anal. Chem.* 63:2338–2345; Szabo et al., 1995, *Curr. Opin. Struct Biol.* 5:699–705; e.g., BIAcore™; LKB Pharmacia, Sweden). Modulators can also be identified by scintillation proximity assays (SPA, described in U.S. Pat. No. 4,568, 649). Binding assays using mitochondrial targeting signals (Hurt et al., 1985, *EMBO J.* 4:2061–2068; Eilers and Schatz, 1986, *Nature* 322:228–231) a plurality of defined polymers synthesized on a solid substrate (Fodor et al., 1991, *Science* 251:767–773) may also be employed.

Two-hybrid systems may be used to identify modulators (see, e.g., U.S. Pat. No. 5,283,317; Zervos et al., 1993, *Cell* 72:223–232; Madura et al., 1993, *J. Biol. Chem.* 268:12046–12054; Bartel et al., 1993, *Biotechniques* 14:920–924; Iwabuchi et al., 1993, *Oncogene* 8:1693–1696; and Brent WO 94/10300). Alternatively, three-hybrid (Licitra et al., 1996, *Proc. Natl. Acad. Sci. USA* 93:12817–12821), and reverse two-hybrid (Vidal et al., 1996, *Proc. Natl. Acad. Sci. USA* 93:10315–10320) systems may be used. Commercially available two-hybrid systems such as the CLONTECH Matchmaker™ systems and protocols (CLONTECH Laboratories, Inc., Palo Alto, Calif.) are also useful (see also, A. R. Mendelsohn et al., 1994, *Curr. Op. Biotech.* 5:482; E. M. Phizicky et al., 1995, *Microbiological Rev.* 59:94; M. Yang et al., 1995, *Nucleic Acids Res.* 23:1152; S. Fields et al., 1994, *Trends Genet.* 10:286; and U.S. Pat. Nos. 6,283,173 and 5,468,614).

Several methods of automated assays have been developed in recent years so as to permit screening of tens of thousands of test agents in a short period of time. High-throughput screening methods are particularly preferred for use with the present invention. The binding assays described herein can be adapted for high-throughput screens, or alternative screens may be employed. For example, continuous format high throughput screens (CF-HTS) using at least one porous matrix allows the researcher to test large numbers of test agents for a wide range of biological or biochemical activity (see U.S. Pat. No. 5,976,813 to Beutel et al.). Moreover, CF-HTS can be used to perform multi-step assays.

Alternatively, interactions with test agents may be detected by indirect indicators of binding, such as stabilization/destabilization of protein structure, or activation/inhibition of biological function. For example, modulating agents may be identified by an increase or decrease in levels of carbon dioxide or NADH produced by *P. pastoris* FDH upon incubation with formate and NAD+. Specifically, agonist agents would be expected to increase carbon dioxide and NADH levels, whereas antagonist agents would be expected to decrease carbon dioxide and NADH levels produced by the enzyme. In one embodiment of the present invention, an agonist or antagonist is identified by incubating the disclosed *P. pastoris* FDH, or fragments or variants thereof, with a test agent. The *P. pastoris* FDH may be expressed by host cells, or may be isolated therefrom. The *P. pastoris* FDH and test agent is incubated with formate and NAD+, and levels of carbon dioxide or NADH are determined and compared with standard levels. Increased levels of carbon dioxide or NADH indicate identification of an agonist agent, while decreased levels of carbon dioxide or NADH indicate identification of an antagonist agent. The conversion of NAD+ to NADH can be measured, for example, by an increase in OD at 340 nm, as described herein below.

Embodiments

This invention encompasses, but is not limited to the following embodiments:

An isolated nucleic acid comprising a nucleotide sequence encoding amino acid sequence SEQ ID NO:5.

An isolated nucleic acid comprising a nucleotide sequence encoding at least 32 contiguous amino acids of SEQ ID NO:5.

An isolated nucleic acid comprising a nucleotide sequence encoding at least 32 contiguous amino acids of the NAD-binding domain of SEQ ID NO:5.

An isolated nucleic acid comprising a nucleotide sequence encoding at least 21 contiguous amino acids of the catalytic domain of SEQ ID NO:5.

An isolated nucleic acid comprising a nucleotide sequence selected from the group consisting of SEQ ID NO:1, SEQ ID NO:2, SEQ ID NO:3, and SEQ ID NO:4.

An isolated nucleic acid comprising at least 21 contiguous nucleotides of a nucleotide sequence selected from the group consisting of SEQ ID NO:1, SEQ ID NO:2, SEQ ID NO:3, and SEQ ID NO:4.

An isolated nucleic acid comprising a nucleotide sequence which is at least 77% identical to a nucleotide sequence selected from the group consisting of SEQ ID NO:1, SEQ ID NO:2, SEQ ID NO:3, and SEQ ID NO:4.

An isolated nucleic acid comprising a nucleotide sequence which is complementary to a nucleotide sequence of the invention (above).

A vector comprising an isolated nucleic acid of the invention (above).

A host cell comprising a vector of the invention (above), wherein the host cell is selected from the group consisting of bacterial, fungal, insect, mammalian, and plant cells.

The bacterial host cell of the invention (above), wherein the bacterial host cell is selected from the group consisting of *Escherichia coli, Staphlococcus aureus, Bacillus licheniformis, Bacillus amyloliquefaciens,* and *Bacillus subtilis, Streptomyces lividans, Streptomyces coelicolor.*

A probe comprising an isolated nucleic acid of the invention (above). In specific aspects, the probe may comprise an isolated nucleic acid of any one of the sequences SEQ ID NO:6–15.

A primer comprising an isolated nucleic acid of the invention (above). In specific aspects, the primer may comprise an isolated nucleic acid of any one of the sequences SEQ ID NO:6–15.

A recombinant polypeptide comprising amino acid sequence SEQ ID NO:5.

A recombinant polypeptide comprising at least 32 contiguous amino acids of SEQ ID NO:5.

A recombinant polypeptide comprising at least 32 contiguous amino acids of the NAD-binding domain of SEQ ID NO:5.

A recombinant polypeptide comprising at least 21 contiguous amino acids of the catalytic domain of SEQ ID NO:5.

A recombinant polypeptide comprising an amino acid sequence which is at least 86% identical to an amino acid sequence of SEQ ID NO:5.

An antibody which binds to a recombinant polypeptide of the invention (above). In specific aspects, the antibody may comprise a monoclonal antibody.

A kit for detecting a nucleic acid comprising:
 a) a probe of the invention (above); and
 b) at least one component to detect binding of the probe to a nucleic acid.

A kit for detecting an amino acid sequence comprising:
 a) an antibody of the invention (above); and
 b) at least one component to detect binding of the antibody to an amino acid sequence.

A method for detecting a nucleic acid comprising:
 a) incubating a probe of the invention (above) with a biological sample comprising nucleic acids, thereby forming a hybridization complex; and
 b) detecting the complex formed in (a), wherein the presence of the complex indicates detection of a nucleic acid.

A method for detecting a polypeptide comprising:
 a) incubating an antibody of the invention (above) with a biological sample comprising polypeptides, thereby forming a complex; and b) detecting the complex formed in (a), wherein the presence of the complex indicates detection of a polypeptide.

A method for detecting a binding factor comprising:
- a) incubating an isolated nucleic acid of the invention (above) with a test agent, thereby forming a complex; and
- b) detecting the complex formed in (a), wherein the presence of the complex indicates detection of a binding factor.

A method for detecting a binding factor comprising:
- a) incubating a recombinant polypeptide of the invention (above) with a test agent, thereby forming a complex; and
- b) detecting the complex formed in (a), wherein the presence of the complex indicates detection of a binding factor.

A method for producing a recombinant polypeptide comprising:
- a) culturing a host cell of the invention (above) under conditions suitable for the production of a recombinant polypeptide; and
- b) recovering the recombinant polypeptide from the host cell or host cell culture, thereby producing the recombinant polypeptide.

A method of isolating a recombinant polypeptide comprising:
- a) incubating a biological sample obtained from a host cell expressing recombinant polypeptide comprising amino acid sequence SEQ ID NO:5 with an antibody of the invention (above), thereby forming a complex; and
- b) recovering a polypeptide from the complex, thereby isolating the polypeptide.

A method of producing nicotinamide adenine dinucleotide (NAD+) in a reduced form (NADH) comprising: incubating a recombinant polypeptide of the invention (above) with formate and NAD+ under conditions to allow oxidation of the formate and reduction of the NAD+, thereby producing NADH.

A method of producing nicotinamide adenine dinucleotide (NAD+) in a reduced form (NADH) comprising: incubating a host cell of the invention (above) with formate and NAD+ under conditions to allow oxidation of the formate and reduction of the NAD+, thereby producing NADH.

A method of reducing a substrate comprising: incubating a recombinant polypeptide of the invention (above) with formate, nicotinamide adenine dinucleotide (NAD+), substrate, and a reducing enzyme under conditions to allow oxidation of the formate, reduction of the NAD+, and thereby allow reduction of the substrate. In one aspect, the substrate is N-P-α-aminochloroketone and the reducing enzyme is an aminochloroketone dehydrogenase. In another aspect, the substrate is 2-pentanone, and the reducing enzyme is pentanone reductase, also known as 2-ketoreductase. In a further aspect, the substrate is an L-amino acid and the reducing enzyme is an L-amino acid dehydrogenase. In yet another aspect, the L-amino acid is selected from the group consisting of L-alanine, L-leucine, and L-phenylalanine and the reducing enzyme is selected from the group consisting of L-alanine, L-leucine, and L-phenylalanine dehydrogenase. In still another aspect, the substrate is a chloro-2-oxo-1-(phenylmethyl) propylcarbamic acid 1,1-dimethylethyl ester and the reducing enzyme is an amino chloroketone dehydrogenase. In yet a further aspect, the substrate is ketoacid acetal and the reducing enzyme is phenylalanine dehydrogenase. In another aspect, the substrate is α-keto-β-hydroxyisovalerate and the reducing enzyme is leucine dehydrogenase. In a further aspect, the substrate is the keto acid of Nε-Cbz-L-lysine and the enzyme is L-2-hydroxyisocaproate dehydrogenase.

A method of reducing a ketone to produce an alcohol comprising: incubating a recombinant polypeptide of the invention (above) with formate, nicotinamide adenine dinucleotide (NAD+), and the ketone and ketone reductase under conditions to allow oxidation of the formate, reduction of the NAD+, and reduction of the ketone, thereby producing the alcohol. In various aspects, the ketone is selected from the group consisting of 2-pentanone, N-P-α-amino chloroketone, α-keto-β-hydroxyisovalerate, and 5-(1,3-dioxolan-2-yl)-2-oxo-pentanoic acid.

A method of reducing a ketone to produce an alcohol comprising: incubating a host cell of the invention (above) with formate, nicotinamide adenine dinucleotide (NAD+), and the ketone and ketone reductase under conditions to allow oxidation of the formate, reduction of the NAD+, and reduction of the ketone, thereby producing the alcohol. In various aspects, the ketone is selected from the group consisting of 2-pentanone, N-P-α-amino chloroketone, α-keto-β-hydroxyisovalerate, and 5-(1,3-dioxolan-2-yl)-2-oxo-pentanoic acid.

A method of reducing a ketone to produce an alcohol comprising: incubating a recombinant polypeptide of the invention (above) with formate, nicotinamide adenine dinucleotide (NAD+), a 2-pentanone ketone and an isolated *Gluconobacter oxydans* 2-keto reductase reducing enzyme having the amino acid sequence as set forth in SEQ ID NO:24, under conditions to allow oxidation of the formate, reduction of the NAD+, and reduction of the ketone, thereby producing the alcohol.

A method of reducing a ketone to produce an alcohol comprising: incubating a recombinant polypeptide of the invention (above) with formate, nicotinamide adenine dinucleotide (NAD+), a 2-pentanone ketone and an isolated recombinant *Gluconobacter oxydans* 2-keto reductase reducing enzyme having the amino acid sequence as set forth in SEQ ID NO:24, under conditions to allow oxidation of the formate, reduction of the NAD+, and reduction of the ketone, thereby producing the alcohol.

A method for detecting an agonist agent comprising:
- a) incubating a host cell of the invention (above) with a test agent;
- b) incubating the host cell and test agent of (a) with formate and NAD+ under conditions to allow oxidation of formate and reduction of NAD+;
- c) measuring levels of carbon dioxide or NADH, produced in step (b); and
- d) comparing the levels determined in step (c) to levels produced in the absence of the test agent, wherein an increase in levels indicates detection of an agonist agent.

A method for detecting an agonist agent comprising:
- a) incubating a recombinant polypeptide of the invention (above) with a test agent;
- b) incubating the host cell and test agent of (a) with formate and NAD+ under conditions to allow oxidation of formate and reduction of NAD+;

c) measuring levels of NADH produced in step (b); and
d) comparing the levels determined in step (c) to levels produced in the absence of the test agent, wherein an increase in levels indicates detection of an agonist agent.

An American Type Culture Collection deposit corresponding to ATCC Accession No. PTA-3691.

A nucleic acid comprising the nucleotide sequence deposited as ATCC Accession No. PTA-3691.

A recombinant polypeptide encoded by the nucleotide sequence deposited as ATCC Accession No. PTA-3691.

EXAMPLES

The examples as set forth herein are meant to exemplify the various aspects of the present invention and are not intended to limit the invention in any way.

Example 1

Identification of the *P. pastoris* FDH Gene

Library construction: *Pichia pastoris* strain GS115 (ATCC 20864) was grown in 10 ml of medium containing 1% Bacto yeast extract (DIFCO, Detroit, Mich.), 2% Bacto peptone (DIFCO), and 2% dextrose at 30° C. with vigorous shaking. After 24 hr, cells were harvested by centrifugation and chromosomal DNA prepared using the procedure described in Ausubel et al. (Eds.), 1981, *Current Protocols in Molecular Biology*, vol. 2, section 13.11.2, John Wiley and Sons, New York, N.Y. DNA was cleaved with restriction endonucleases BamHI, EcoRI, HindIII, KpnI, and PstI under conditions recommended by the manufacturer (Promega, Madison, Wis.). Approximately 3 μg of each digested DNA was electrophoresed at 20 v for 18 hr through a 0.8% agarose gel in TAE buffer (0.04 M Trizma base, 0.02 M acetic acid, and 0.001 M EDTA, pH 8.3) containing 0.5 μg/ml ethidium bromide. Fragments were transferred to a Hybond N+ nylon filter (Amersham Pharmacia, Piscataway, N.J.) using a VacuGene blotting apparatus (Amersham-Pharmacia).

To identify the *P. pastoris* formate dehydrogenase (FDH) gene, a labeled polymerase chain reaction (PCR) fragment representing the homologous gene from *Candida boidinii* was used as a probe. The chromosomal version of this gene had been previously cloned as a 2.8 kilobase (kb) EcoRI fragment in plasmid pZero1 (Invitrogen, Carlsbad, Calif.). The primers for amplification of the *C. boidinii* FDH gene included the following sequences: 5' ATGAAGATCGTTT-TAGTCTTA 3' (sense; SEQ ID NO:6) and 5' TTTCT-TATCGTGTTTACCGTA 3' (anti-sense; SEQ ID NO:7). The amplification reaction mixture included 50 mM KCl, 10 mM Tris-HCl (pH 9.0), 0.1% Triton® X-100, 0.2 mM each deoxynucleotide triphosphate (dATP, dCTP, dGTP, dTTP), 3 mM MgCl$_2$, 0.4 nM each primer, 2.5 U Tth DNA polymerase (Promega), and 10 pg plasmid DNA containing the cloned *C. boidinii* FDH gene. Amplification was performed using a Perkin-Elmer Model 480 thermocycler with autoextension (Perkin-Elmer, Foster City, Calif.). Amplification conditions included incubation at 94° C., for 4 min, followed by 25 cycles of incubation at 94° C. for 1 min, 50° C. for 1 min, and 72° C. for 1.5 min.

The PCR product was extracted with an equal volume of 1:1 phenol:chloroform (GibcoBRL, Gaithersburg, Md.), and centrifuged at 13,000×g for 5 min. The upper aqueous phase was removed and placed into a new microcentrifuge tube. DNA was precipitated by the addition of 0.1 vol 3 M sodium acetate and 2 vol ice-cold ethanol. After centrifugation at 13,000×g for 5 min, liquid was aspirated from the tube, and the pellet washed with 0.5 ml ice-cold 70% ethanol. Liquid was aspirated again, and the pellet allowed to air dry for 30 min at room temperature. DNA was resuspended in 0.05 ml dH$_2$O. A small aliquot was electrophoresed on a 1.0% agarose gel in TAE buffer for 2 hr at 100 v against DNA mass ladder (GibcoBRL) to determine the concentration of the PCR fragment. The nucleotide sequence of the PCR amplified fragment is shown in FIG. 1E.

Library screening: The PCR fragment was labeled (via non-isotopic labeling), the labeled fragment was hybridized to the filter containing *P. pastoris* chromosomal digests, the filter was washed, and the label was detected using the reagents and instructions provided with the ECL Nucleic Acid Labeling and Detection Kit (Amersham-Pharmacia). Stringent wash conditions used 0.2×SSC (20×SSC=173.5 g NaCl and 88.2 g NaCl, pH 7.0 in 50 ml per wash) and 0.4% SDS at 50° C. A single band was visible from each digest. The EcoRI digest was chosen for further analysis, as it produced the smallest fragment (2.1 kb).

Approximately 10 μg of *P. pastoris* chromosomal DNA was digested with 25 U EcoRI for 2 hr at 37° C. in a final volume of 0.1 ml using buffer recommended by the manufacturer (Promega). The digested DNA was electrophoresed on a 0.8% agarose gel in TAE buffer at 20 v for 18 hr. Fragments between 1.8 and 2.2 kb were identified by comparison to a 1 kb DNA ladder (GibcoBRL), and excised using a scalpel. The 2.1 kb DNA fragment was isolated from the agarose using the QIAquick Gel Extraction Kit (QIAGEN, Chatsworth, Calif.). The isolated fragment was ligated to EcoRI-digested pZero1 vector DNA in a 2:1 molar ratio in a total volume of 10 μl at 22° C. for 2 hr. DNA was precipitated by addition of 15 μl dH$_2$O and 250 μl 1-butanol, and pelleted at 13,000×g in a microcentrifuge for 5 min. Liquid was removed by aspiration, and the DNA was dried in a SpeedVac (Savant Instruments, Farmingdale, N.Y.) for 5 min under low heat. The pellet was resuspended in 5 μl dH$_2$O.

The resuspended DNA (25 ng) was transformed by electroporation into 0.04 ml *E. coli* DH10B competent cells (GibcoBRL). SOC medium was immediately added (0.96 ml; SOC=0.5% yeast extract, 2% tryptone, 10 mM NaCl, 2.5 mM KCl, 10 mM MgCl$_2$, 10 mM MgSO$_4$, and 20 mM glucose per liter), and the cells incubated in a shaker for 1 hr at 37° C. and 225 rpm. Cells were spread onto a 132 mm Hybond N+ membrane (Amersham Pharmacia) placed on top of LB agar medium containing 50 μg/ml Zeocin (Invitrogen) and 0.5 mM ispropyl-β-D-thiogalactopyranoside (IPTG). Cells were incubated at 37° C. for 20 hr.

Following this, colonies were replicated onto two fresh filters that were placed on top of LB Zeocin agar medium. The filters were incubated at 37° C. for 4 hr. Colonies were lysed in situ by placing the filters on a piece of Whatman 3MM paper (Whatman International, Maidstone, UK) saturated with 0.5 M NaOH for 5 min. The filters were dried for 5 min on Whatman paper, then neutralized on 3MM paper soaked in 1.0 M Tris-HCl, pH 7.5 for 2 min, and dried for 2 min. Membranes were placed on top of 3MM paper saturated with 1.0 M Tris-HCl, pH 7.0/1.5 M NaCl for 10 min. DNA was crosslinked to the filters by exposure to ultraviolet light in a Stratagene UV Stratalinker 2400 set to "auto crosslink" mode (Stratagene, La Jolla, Calif.). Cell debris was removed from the membranes by immersing in 3×SSC/0.1% SDS and wiping the surface with a wetted Kimwipe® (Kimberly-Clark Co., Roswell, Ga.), then incubating in the same solution heated to 65° C. for 3 hr with agitation. Filters were rinsed with dH$_2$O and used immediately or wrapped in SaranWrap® and stored at 4° C.

Hybridization, washing, and detection was performed as described above using the Amersham ECL kit with the 2.8 kb C. boidinii FDH gene probe.

Four putative hybridizing colonies were picked from the master plate, inoculated into SOC medium containing 25 μg/ml Zeocin, and grown at 37° C. for 24 hr at 250 rpm. One milliliter of cell culture was centrifuged, and the cells were pelleted. Plasmid DNA was isolated using the S.N.A.P. mini-plasmid kit (Invitrogen). An aliquot (2.5 ml) was digested with either EcoRI or SspI, and electrophoresed on a 1.0% TAE agarose gel for 2 hr at 100 v. The DNA was transferred to Hybond N+ membrane (Amersham Pharmacia) and probed with labeled FDH PCR fragment as described above. The 2.1 kb EcoRI fragment of one of the plasmid isolates hybridized strongly to the probe. This recombinant plasmid was named pFDH2.1.

Sequence analysis: DNA sequencing of the 2.1 kb insert of pFDH2.1 was performed using the ALFexpress unit and the AutoRead kit (Amersham-Pharmacia). The M13 "forward" and "reverse" primers and internal primers were used to cover both strands. Internal primers included the following sequences:

```
5' TTTTCTAACTCAGAGTTTTC 3';      (SEQ ID NO:8)

5' AACCAATTCTTCCAGCACC 3';       (SEQ ID NO:9)

5' TACCTGAGTAATGAGGAGTC 3';      (SEQ ID NO:10)

5' AAACCCAATCGGGAAACTTT 3';      (SEQ ID NO:11)

5' GTACCAAAATGGCAA 3';           (SEQ ID NO:12)

5' CAAAGGCTACAGAAATCCGA 3'.      (SEQ ID NO:13)
```

The complete P. pastoris FDH nucleotide sequence and predicted amino acid sequence is shown in FIGS. 1A–1B and FIGS. 1C–1D. The P. pastoris FDH coding region is 1095 bp in length and encodes a 365 amino acid protein (MW 40,012 daltons). The P. pastoris FDH nucleotide and deduced amino acid sequences showed significant homology to other formate dehydrogenase sequences of the methylotropic yeasts Candida boidinii, Candida methylica and Pichia angusta. The P. pastoris FDH nucleotide and amino acid sequences also showed significant homology to formate dehydrogenase sequences identified in Mycosphaerella graminicola.

BestFit sequence analysis (SeqWeb package, Genetics Computer Group, Madison, Wis.) indicated that the amino acid sequence of P. pastoris FDH shared 85.0% sequence identity with the amino acid sequence of C. boidinii FDH, 84.8% sequence identity with the amino acid sequence of C. methylica FDH, and 82.2% sequence identity with the amino acid sequence of P. angusta FDH. The longest stretch of identical amino acids shared by P. pastoris FDH and P. angusta FDH was 31 contiguous amino acids in length. The longest stretch of identical amino acids shared by P. pastoris FDH and C. boidinii FDH was 24 contiguous amino acids in length. The longest stretch of identical amino acids shared by P. pastoris FDH and C. methylica FDH was also 24 contiguous amino acids in length.

BestFit analysis (Genetics Computer Group) further indicated that the nucleotide sequence of P. pastoris FDH shared 76.5% sequence identity with the nucleotide sequence of P. angusta FDH, 74.4% sequence identity with the nucleotide sequence of C. boidinii FDH, and 74.5% sequence identity with the nucleotide sequence of C. methylica FDH. The longest stretch of identical nucleotides shared by P. pastoris FDH and P. angusta FDH was 15 contiguous nucleotides in length. The longest stretch of identical amino acids shared by P. pastoris FDH and C. boidinii FDH was 20 contiguous nucleotides in length. The longest stretch of identical nucleotides shared by P. pastoris FDH and C. methylica FDH was also 20 contiguous nucleotides in length.

BLASTP 2.21 analysis (http://www.ncbi.nlm.nih.gov/BLAST/) and a conserved domain (CD) search indicated that P. pastoris FDH contained two highly conserved domains: a 2-Hacid_DH_C, D-isomer specific 2-hydroxyacid dehydrogenase, NAD-binding domain (gnl|Pfam|pfam02826), between amino acids 117–309; and a 2-Hacid_DH, D-isomer specific 2-hydroxyacid dehydrogenase, catalytic domain (gnl|Pfam|pfam00389), between amino acids 16–115. Sequence alignments showed that the longest stretch of identical amino acids shared by the P. pastoris FDH NAD-binding domain and previously identified FDH NAD-binding domains was 31 contiguous residues in length. The longest stretch of identical amino acids shared by the P. pastoris FDH catalytic domain and previously identified FDH catalytic domains was 20 contiguous residues in length.

Example 2

Subcloning and Expression of P. pastoris FDH Gene in E. coli

Subcloning: The P. pastoris FDH gene was subcloned into expression vector pBMS2000 (disclosed in U.S. Pat. No. 6,068,991, issued May 30, 2000 to S. W. Liu et al.) as follows. Oligonucleotide primers containing the 5' and 3' end of the P. pastoris FDH gene along with compatible restriction endonuclease cleavage sites were prepared:

```
5' TCGTCATGAAAATCGTTCTCGTTTTG 3'    (5' end; sense)       (SEQ ID NO:14)
      BspHI 5' TACTGTTTTTCCAGCGTATTCCTAGGCT 3'  (3' end; anti-sense)  (SEQ ID NO:15)
                         BamHI
```

High-fidelity PCR amplification of the P. pastoris FDH gene was carried out in four 100 ml aliquots, each containing 1×TaqPlus reaction buffer (Stratagene), 0.2 mM each deoxynucleotide triphosphate (dATP, dCTP, dGTP, and dTTP), 0.4 nM each oligonucleotide, 2.5 U TaqPlus DNA polymerase (Stratagene), and 10 pg plasmid DNA containing the cloned P. pastoris FDH gene. The amplification conditions included incubation at 94° C. for 4 min, followed by 25 cycles of incubation at 94° C. for 1 min; 50° C. for 1 min; and 72° C. for 1.5 min, using a Perkin-Elmer Model 480 thermocycler with autoextension.

The PCR reaction mixture was extracted with an equal volume of 1:1 phenol:chloroform (GibcoBRL), and centrifuged at 13,000×g for 5 min. The upper aqueous phase was removed and placed in a new microcentrifuge tube. DNA was precipitated by addition of 0.1 vol 3 M sodium acetate and 2 vol ice-cold ethanol. After centrifugation at 13,000×g for 5 min, liquid was aspirated from the tube, and the pellet washed with 0.5 ml ice-cold 70% ethanol. Liquid was aspirated again, and the pellet was allowed to air dry for 30 min at room temperature.

Amplified DNA was digested with 20 units each of BspHI and BamHI for 3 hr at 37° C. in a total volume of 50 μl. In parallel, the pBMS2000 vector was digested with BspHI and BamHI. The digested samples were electrophoresed on a 1.0% TAE agarose gel for 2 hr at 100 v. The bands corresponding to the FDH gene (1100 bp fragment) and linearized vector (4700 bp fragment) were excised from the gel and purified using the QIAquick Gel Extraction Kit (QIAGEN). The concentrations of the isolated fragments were estimated by electrophoresis against the low molecular weight mass ladder (GibcoBRL). Ligation and transformation were carried out as described in Example 1. Cells containing plasmid were selected on LB agar containing 30 μg/ml neomycin at 37° C. for 20 hr.

Screening clones: Plasmids with the desired insert were identified by colony PCR in capillary tubes using the Rapid-Cycler (Idaho Technology, Salt Lake City, Utah). Each reaction mixture contained 50 mM Tris-HCl (pH 8.3), 4 mM $MgCl_2$, 0.25 mg/ml bovine serum albumin, 2% sucrose 400, 0.1 mM cresol red, 0.4 nM each primer (above), and 2.5 U Taq DNA polymerase (Promega). The reaction mixture was divided into 10 μl aliquots, and pipetted into the wells of a round-bottom microtiter plate. A neomycin-resistant colony was picked using a disposable plastic inoculation needle, swirled into the reaction mixture, and transferred to LB-neomycin agar. Each reaction mixture aliquot was drawn into a 30 μl capillary tube, and the tube was flame-sealed at both ends. Cells were lysed and DNA denatured by incubation at 94° C. for 30 sec; amplification was performed using 30 cycles of incubation at 94° C. for 0 sec; 40° C. for 0 sec, and 72° C. for 60 sec using a RapidCycler Thermocycler (Idaho Technologies, Salt Lake City, Utah). Samples were electrophoresed on a 1.0 TAE agarose gel for 2 hr at 100 v. Seven samples out of 17 tested showed a strong band at 1100 bp. One colony containing this plasmid (named pBMS2000-PPFDH) was chosen for further study.

Expression and assay: The pBMS2000-PPFDH plasmid was transformed into four additional *E. coli* strains by electroporation: BL21(DE3), BL21(DE3)Star (containing a plasmid encoding three rare tRNAs; Stratagene), JM110, and W3110. Transformed cells were selected on LB-neomycin agar medium. A single colony from each strain was inoculated into 10 ml MT3 medium (1.0% NZAmine A, 2.0% Yeastamin, 2.0% glycerol, 0.6% $Na_2HPO_4$, 0.3% $KH_2PO_4$, 0.125% $(NH_4)_2SO_4$, and 0.0246% $MgSO_4$) containing 30 μg/ml neomycin. The cultures were incubated at 28° C., 250 rpm, for 20 hr. Following this, the cultures were diluted into fresh medium to an $OD_{600}$ nm of 0.25. The cultures were incubated under the same conditions as above until the $OD_{600}$ value reached 1.0±0.1. IPTG was added to a final concentration of 0.1 mM, and the cultures grown at the above conditions for 20 hr. Cells were pelleted by centrifugation (5,000×g) for 7 min, and the growth medium was removed. Cells were then washed with an equal volume ice cold 50 mM $KPO_4$ buffer (pH 7.3)/2 mM dithiothreitol. The cells were pelleted again, and the wet cell weight was recorded.

For formate dehydrogenase activity assay, samples were stored at –20° C. until required, or were used immediately. The cells were resuspended in the $KPO_4$/DTT buffer at 10 ml/g wet cell weight and kept on ice. Lysis was carried out using 0.8 ml of the sample in a 1.5 ml microfuge tube with a Fisher Sonic Dismembrator (Fisher Scientific, Pittsburgh, Pa.) and a microtip on power level 10 for 3×10 sec. Samples were placed on ice for at least 1 min between each cycle of sonication. Debris was pelleted by centrifugation at 13,000×g for 5 min. The assay reaction mixture included 0.7 ml 0.1 M $KPO_4$ buffer (pH 7.7), 0.10 ml 1.0 M sodium formate, 0.15 ml 6.67 mg/ml NAD+ solution, and up to 0.05 ml extract ($dH_2O$ to 1.0 ml if needed). The reaction was carried out in a disposable semi-micro cuvette at room temperature. Two minutes after extract addition, the $OD_{340}$ nm value was recorded. A second measurement was made 3 min later.

Activity based on the reduction of NAD+ to NADH was calculated as follows: $\Delta OD_{340}/6.22 \times 3 \times$ volume extract used (ml), where $\Delta OD_{340}$ is the increase in optical density between 2 and 5 min post-extract addition, 6.22 is the molar extinction coefficient for NADH at 340 nm, and 3 is the time in minutes. No background activity (i.e., reduction of NAD+ without presence of extract) was observed under the stated reaction conditions. Maximum activity was obtained using strain JM110 (pBMS2000-PPFDH): 2.27 U/ml or 22.7 U/g cell. The induction conditions were optimized by varying the IPTG concentration. At 0.05 mM IPTG, formate dehydrogenase activity of the JM110 (pBMS2000-PPFDH) strain reached 4.1 U/ml (41.0 U/mg wet cell weight). The enzyme was specific for NAD+ as no activity was detected with NADP as co-factor.

The cloned *P. pastoris* FDH gene was deposited as plasmid pBMS2000-PPFDH in bacterial strain JM110 at the American Type Culture Collection (ATCC), 10801 University Boulevard, Manassas, Va. 20110-2209 on Sep. 7, 2001 under ATCC Accession No. PTA-3691 according to the terms of the Budapest Treaty.

Example 3

Reduction Reaction for 2-Pentanone Using Recombinant *P. pastoris* FDH

To demonstrate the utility of the recombinant *P. pastoris* FDH enzyme as a means of co-factor regeneration, it was substituted for purchased *C. boidinii* FDH in the reduction of 2-pentanone to 2-pentanol by recombinant pentanone reductase (also known as 2-ketoreductase). The reaction mixture contained 0.18 mg NAD+, 30 mg sodium formate, 0.3 units formate dehydrogenase (purchased from Sigma, St. Louis, Mo., or from cell extract of JM110 (pBMS2000-PPFDH)), 2 mg 2-pentanone (Sigma Chemicals, St. Louis, Mo.) and 0.5 ml extract from an *E. coli* culture expressing a novel pentanone reductase, or 2-ketoreductase (see Examples 9–15, below). A reaction mixture without formate dehydrogenase was prepared in parallel. The reactions were carried out in a culture tube at 28° C. with shaking at 200 rpm. After 16 hr, samples were quenched with 2 ml of ethyl acetate and analyzed by gas chromatography. Complete reduction of 2-pentanone was observed in samples containing formate dehydrogenase obtained commercially or from cell extracts. No reduction took place in the absence of formate dehydrogenase. Previously frozen JM110 (pBMS2000-PPFDH) cells could be substituted for extracts with no loss in conversion efficiency.

Example 4

Biotransformation Reaction for Nε-Carbobenzoxy-L-Lysine Using Recombinant *P. pastoris* FDH The following experiments (adapted from R. L. Hanson et al., 1992, *Appl. Microb. Biotechnol.* 37:599–603) employ *P. pastoris* FDH in the conversion of Nε-carbobenzoxy(Cbz)-L-lysine 1b (FIG. 2) to a keto acid 2b (FIG. 2), which is then converted to Cbz-L-oxylysine 3b (FIG. 2) with appropriate enantioselectivity. Cbz-L-oxylysine, in turn, is a key intermediate in the synthesis of ceranopril 4 (FIG. 2), an angiotensin converting enzyme (ACE) inhibitor for the treatment of hypertension (D. S. Karanewsky et al., 1988, *J. Med. Chem.* 31:204–212). The conversion reaction includes: 1) *P.*

*pastoris* formate dehydrogenase; 2) NAD+; 3) L-amino acid oxidase; 4) L-2-hydroxyisocaproate dehydrogenase; and 5) and NE-Cbz-L-lysine.

Enzyme Assays: L-Amino acid oxidase is monitored by coupling the $H_2O_2$ evolved in the reaction to the oxidation of o-dianisidine catalyzed by horseradish peroxidase (Berezov and Lukasheva, 1988, *Biochem. Int.* 17:529–534). The reaction solution contains in 1 ml: 50 mM potassium phosphate, pH 7.4, 1 mM L-lysine or lysine derivative, 0.2 mM o-dianisidine, and 10 μg (2.17 units (U)) horseradish peroxidase. The reaction is started by the addition of L-amino acid oxidase, and the increase in absorbance at 460 nm is monitored (absorbance=11.3 $mM^{-1}$ $cm^{-1}$). All continuous spectrophotometric assays are performed at 25° C.

The reaction solution for L-2-hydroxyisocaproate dehydrogenase (L-HIC dehydrogenase) coupled to L-amino acid oxidase contains in 1 ml: 0.1 M potassium phosphate, pH 7.4, 1 mM lysine or lysine derivative, 2000 U bovine liver catalase, and 1.7 U L-HIC dehydrogenase. Reactions are started by the addition of L-amino acid oxidase and the absorbance decrease at 340 nm is monitored. The catalase assay contains in 1.0 ml: 0.1 M potassium phosphate, pH 7.4, and 0.06% $H_2O_2$. Absorbance decrease after addition of enzyme is monitored at 240 nm (absorbance=0.0436 $mM^{-1}$ $cm^{-1}$). Protein is determined by the dye-binding method of Bradford (M. M. Bradford, 1976, *Anal. Biochem.* 72:248–254), using bovine serum albumin as standard.

Analytical methods: HPLC analysis of Cbz-L-lysine transformations are performed with a Hewlett-Packard (Palo Alto, Calif.) hypersil C18 20 cm×4.6 cm column, with 5 μm particle size. The column temperature is 40° C., the mobile phase is 37% methanol and 63% water containing 0.05% $H_3PO_4$. The flow rate is 1 ml/min, the detection wave length is 215 nm, and the injection volume is 5 μl. Retention times are 9.8 min for 6-Cbz-amino-2-oxohexanoic acid, 13.7 min for Cbz-L-oxylysine, and 23.3 min for Cbz-L-lysine, with the keto acid peak skewed toward higher retention times. Samples are boiled for 2 min, centrifuged, and filtered before HPLC analysis. Optical purity of Cbz-oxylysine is determined by derivation and separation of diastereomers by gas chromatography (Jemal and Cohen, 1987, *J. Chromatogr.* 394:388–394).

Microbial growth conditions: *Providencia alcalifaciens* SC9036 is obtained as ATCC strain 13159. *P. alcalifaciens* is grown on medium described by Szwajcer et al. (1982, *Enzyme Microb. Technol.* 4:409–413) containing 1% peptone, 0.2% casein hydrolysate, 0.2% yeast extract, and 0.6% NaCl at pH 7.2–7.4. Growth is at 37° C., and 100 rpm in shake flasks. A 200 ml overnight culture is used to inoculate a 15 L tank containing the same medium at 37° C., stirred at 200 rpm, and aerated at 20 L/min. After 11 h, cells are harvested by centrifugation, washed with 50 mM potassium phosphate buffer, pH 7.4, and stored frozen at −18° C. until used for biotransformation.

Enzyme localization: Cells (1.40 g, wet weight) are collected from a 17 h shake flask culture, and sonicated in 15 ml of 50 mM potassium phosphate, pH 7.4. Debris is removed by centrifugation for 10 min at 12,000 g. The extract supernatant is centrifuged for 1 h at 101,000 g to give a supernatant and pellet fraction. The pellet is resuspended in 2 ml of 50 mM potassium phosphate, pH 7.4. Oxidation of Cbz-L-lysine is measured by incubating 5 mM Cbz-L-lysine with 0.6 ml of extract or 101,000 g pellet or supernatant fractions in 1.5 ml containing 0.1 M potassium phosphate, pH 7.4, and 3000 U catalase for 16 h. The amount of 6-Cbz-amino-2-oxohexanoic acid produced by 1 mg *Crotalus adamanteus* venom L-amino acid oxidase under these conditions is used as a standard for 100% conversion in the HPLC assay.

Materials: Commercial sources are: lysyl oxidase (Yamasa Shoyu, Choshi, Chiba, Japan); L-amino acid oxidase Type 1 from *Crotalus adamanteus* (Sigma, St. Louis, Mo.); polyethylene glycol (PEG)-2000-NADH (Braunschweiger Biotechnologie, Braunschweig, FRG).

Cbz-L-lysine conversion to Cbz-L-oxylysine: For the conversion reaction, 5.6 g Z-lysine is added to 1 L of solution containing 0.1 M potassium phosphate, pH 7.4, and 10 g SC9036 cells, and the mixture is shaken at 200 rpm for 27 h at 30° C. After 24 h, HPLC is used to determine complete conversion to the keto acid. Cells are removed by centrifugation, and 0.2 M sodium formate, 1 mM NAD, 32 U *P. pastoris* formate dehydrogenase, and 66 U L-HIC dehydrogenase are added, and the solution is incubated for 64 h at 28° C. HPLC is used to confirm conversion to an expected 19 mM Cbz-L-oxylysine. Cbz-L-oxylysine is extracted from the reaction solution with ethyl acetate. The organic layer is dried with $MgSO_4$ and evaporated to an oil under vacuum. The crude product is redissolved in a small amount of ethyl acetate, precipitated by addition of hexane, cooled, filtered, washed, and dried to yield an expected 4 g Cbz-L-oxylysine.

Example 5

Figure 3:
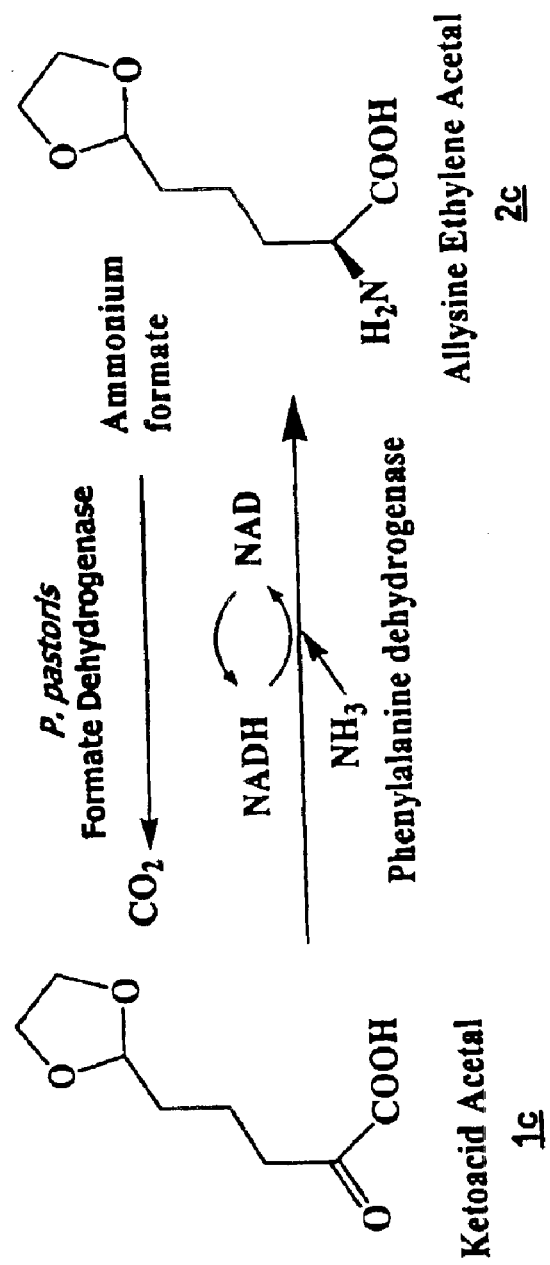
FIG. 3 illustrates the use of *P. pastoris* FDH in the synthesis of allysine ethylene acetal (adapted from R. L. Hanson et al., 2000, *Enzyme Microb. Technol.* 26:348–358). 1c represents ketoacid acetal; 2c represents allysine ethylene acetal.

Reductive Amination Reaction for Ketoacid Acetal Using Recombinant *P. pastoris* FDH The following experiments (adapted from R. L. Hanson et al., 2000, *Enzyme Microb. Technol.* 26:348–358) employ *P. pastoris* FDH in the enzymatic reductive amination of ketoacid acetal 1c (FIG. 3) to allysine ethylene acetal 2c (FIG. 3). Allysine ethylene acetal is a building block in the synthesis of VANLEV (omapatrilat, BMS 186716; U.S. Pat. No. 6,140,088 to Hanson et al.; U.S. Pat. No. 6,162,913 to Moniot et al.; U.S. Pat. No. 6,261,810 B1 to Patel et al.), a vasopeptidase inhibitor in clinical trials (J. A. Robl et al., 1997, *J. Med. Chem.* 40:1570–1577). The reaction includes: 1) *P. pastoris* formate dehydrogenase; 2) NAD+; 3) phenylalanine dehydrogenase; and 4) ketoacid acetal.

Growth of *Thermoactinomyces intermedius*: *Thermoactinomyces intermedius* cells (ATCC 33205) are grown on medium containing 0.5% L-phenylalanine, 2.0% NZ Amine A (Sheffield Products, Chicago, Ill.), 0.5% yeast extract, 0.21% $K_2HPO_4$, 0.1% $NaH_2PO_4$, 0.02% $MgSO_4$·$7OH_2O$, and 0.02% antifoam SAG5693 (OSI Specialties, Inc., South Charleston, W.Va., in fermentors only) at 55° C. Five liters of culture from shake flasks is used to inoculate 100 L medium and the fermentation is conducted under the following conditions: 100 L/min air, 690 mBar gauge pressure, and 500 rev/min agitation. Initial medium pH is 6.5 to 6.9. When the pH exceeds 7.5 (19–21 h), 13 L culture is used to inoculate 240 L medium and the fermentation is conducted under the following conditions: 250 L/min air, 690 mBar gauge pressure, and 210 rev/min agitation. Cells are harvested by centrifugation when the optical density at 600 nm reaches a plateau (3.5–4.5) and are stored frozen until use.

Construction of recombinant strain *E. coli* BL21 (DE3): The *P. pastoris* FDH gene is isolated using PCR and subcloned into plasmid vector pET15b (Novagen, Madison, Wis.). The resulting recombinant vector is then isolated and digested with restriction enzymes AlwNI and EcoRI to drop out the ampicillin resistance marker, which is replaced on ligation with the 1.17 kb AlwNI/EcoRI DNA fragment from plasmid vector pET9b (Novagen) containing the kanamycin resistance gene. The resulting ligation mixture is transformed into *E. coli* strain BL21 (DE3) to yield the final production strain. Expression of the *P. pastoris* FDH gene is under the control of the strong T7 promoter. Induction of FDH expression is with IPTG, and expression of the FDH protein is intracellular.

Growth of *E. Coli* BL21 (DE3) (containing *P. pastoris* FDH): Growth/fermentation medium is as follows: 1.0% NZ Amine A, 2.0% Yeastamin (Staley), 2.0% glycerol, 0.6% $Na_2HPO_4$, 0.3% $KH_2PO_4$, 0.125% $(NH_4)_2SO_4$, 0.025% $MgSO_4 \cdot 7H_2O$, 0.005% kanamycin monosulfate, 0.05% polypropylene glycol (in fermentors only), at 37° C. An overnight (18 h) shake flask culture is used to inoculate fermentation medium to yield an equivalent optical density ($OD_{600}$) of 0.04 at inoculation. Initial medium pH is adjusted to 7.0 to 7.2. No pH control is used during the fermentation. Three 16 L fermentations, two 55 L fermentations, and one 100 L fermentation are carried out. The fermentation is conducted under the following conditions: 1 vvm air, 690 mBar gauge pressure, 300 to 500 rev/min agitation depending on the size of the fermentation. The fermentor is induced with IPTG (100 μM) when the carbon dioxide evolution rate reaches or exceeds 12 mM/L/h and the optical density at 600 nm is greater than or equal to 1.0. After induction, the fermentor is run at existing operating conditions for 8 h. Cells are collected with a Sharples centrifuge, washed with 18 mM potassium phosphate buffer pH 7, then dried under vacuum at 54° C. to less than 6% KF water. The dried cells are milled to less than 10 mesh and stored at 5° C.

Construction of recombinant strain *P. pastoris* SMD1168 (pPICZ-PDH): First, the *T. intermedius* PDH gene is isolated by PCR and subcloned into plasmid vector pPICZ (Invitrogen, SanDiego, Calif.) to give recombinant vector pICZ-PDH. pPICZ-PDH is then digested with restriction enzymes PmeI and NotI. The 2.5 kb DNA fragment containing the PDH gene is ligated into plasmid vector pIC9K (Invitrogen) digested with the same two enzymes to give the final vector pPDH9K. This vector is transformed into *P. pastoris* strain SMD1168, and resulting transformants are screened for resistance to high levels of the antibiotic G418 (4 mg/ml). Drug-resistant transformants producing high levels of PDH are chosen for further experimentation. PDH expression in this system is under the control of the AOX1 promoter, with induction of expression by methanol. Expression of endogenous FDH in this strain is also inducible with methanol. Expression of the PDH protein is intracellular.

Growth of *P. pastoris*: Growth/fermentation media is as follows: 2.0% peptone, 1.0% yeast extract, 1.0% glycerol, 0.282% $K_2HPO_4$, 1.14% $KH_2PO_4$, 1.34% yeast nitrogen base (DIFCO), 0.00004% biotin, and 0.01% antifoam A289 (Sigma, in fermentors only), at 30° C. Fermentor volumes are 16, 55, or 100 L. Overnight shake flask cultures are used to inoculate fermentor medium to give an initial optical density of 0.1. Fermentations are conducted under the following conditions: 1 vvm air and 690 mBar gauge pressure. Dissolved oxygen level is maintained at or above 30% air saturation by increasing the agitation rate manually or automatically. The pH is controlled at 6.0 by addition of $NH_4OH$. The fermentor is induced with a methanol feed (containing % w/v: 19.8% methanol, 2.0% peptone, 1.0% yeast extract, 0.282% $K_2PO_4$, 1.14% $KH_2PO_4$, 1.34% yeast nitrogen base, and 0.00004% biotin) when the glycerol is exhausted. An initial 1.25 ml methanol feed is added per liter, then additional methanol feed is added as needed to maintain a methanol concentration of 0.5 to 1.5 g/L for 48 h. Methanol concentrations are measured every 2 h by gas chromatography or with a YSI 2700 Select analyzer (YSI, Inc., Yellowsprings, Ohio) with an alcohol oxidase membrane installed. Forty-eight hours after initiation of induction, the cells are concentrated 7.1 fold by ceramic membrane crossflow microfiltration, washed with 3 volumes 50 mM potassium phosphate buffer pH 7.2, dried to 1.5% KF water with an Anhydro spray drier (APV Crepaco Inc, Attleboro Falls, Mass.), and stored at 5° C.

Enzyme Assays: *T. intermedius* and *E. coli* cell suspensions in 50 mM potassium phosphate buffer containing 1 mM dithiothreitol are disrupted by sonication. *P. pastoris* cell suspensions in 50 mM potassium phosphate buffer pH 7.3 containing 1 mM dithiothreitol and 0.2% Triton X-100, are disrupted with a Mini-Beadbeater-8TM Cell Disrupter (Biospec Products Inc., Bartlesville, Okla.). The PDH assay contains in 1.0 ml at 40° C.: 0.4 mM NADH, 10 mM sodium phenylpyruvate, 0.75 M $NH_4OH$ adjusted to pH 8.75 with HCl. Absorbance decrease is monitored at 340 nm. The FDH assay contains in 1.0 ml at 35° C.: 1.5 mM NAD, 100 mM sodium formate, 70 mM potassium phosphate buffer, pH 7.7. Absorbance increase is monitored at 340 nm. Enzyme activity units are calculated as micromoles/min based on the rates of absorbance change.

Screening reactions for reductive amination procedures: Reaction mixtures contain in a final volume of 1.0 ml at pH 8.7: 1 M ammonium formate (adjusted to pH 8.7 with $NH_4OH$), 0.1 M keto acid 1c, 1 mM NAD, 0.53 U *P. pastoris* FDH, and glutamate, alanine, leucine, or phenylalanine dehydrogenases. Solutions are incubated at 30° C. for 16 h, then analyzed by HPLC.

Biotransformation of 1c to 2c using heat-dried cells of *T. intermedius* and *E. coli*: Keto acid 1c (10.0 g, 53.14 mmoles) and ammonium formate (3.509 g, 55.65 mmoles), are stirred in 150 ml water containing 4.5 ml (66.6 mmoles) concentrated ammonium hydroxide solution (14.8 M) until the solids are dissolved. The pH is adjusted to 8 by adding additional ammonium hydroxide as necessary. Dithiothreitol (36.2 mg, 0.235 mmoles) and NAD (145.2 mg, 0.212 mmoles) are added, the volume is brought to 200 ml, and the solution is placed in a 250 ml jacketed reactor, maintained at 40° C. and stirred at 280 rev/min. *T. intermedius* heat-dried cells (4.08 g, 333 U PDH) and *E. coli* heat-dried cells (1.64 g, 150 U *P. pastoris* FDH) are added to the stirred solution. After 30 min when the cells are dispersed by the stirrer, the pH is brought from about 7.1 back to pH 8 by addition of concentrated ammonium hydroxide solution (about 0.5 ml). After 3 h, a small addition of ammonium hydroxide is added as required to adjust the pH to 8.0. Thereafter the pH is expected to rise to 8.1 to 8.2 after 6 h, and about 8.5 after 19 h. After the conversion of 1c to 2c is complete, as judged by HPLC, cells are removed by centrifugation, and the cell pellet is washed 4× with 20 ml portions of water.

Biotransformation of 1c to 2c using heat-dried cells of *E. coli* and *P. pastoris*: The lithium salt of 1c (20.0 g, 103.03 mmoles) and ammonium formate (7.796 0 g, 123.63 mmoles) are added to a 1-1 jacketed reactor. Four hundred milliliters of water is added to the reactor and stirred at 350 rev/min until the solids are dissolved. The pH is adjusted to 8 by adding concentrated ammonium hydroxide or 99% formic acid as necessary. Dithiothreitol (65.6 mg, 0.425 mmoles) and NAD (282 mg, 0.425 mmoles are added, then the reactor is heated to 40° C. and maintained at that temperature. *E. coli* BL21 (DE3) (expressing *P. pastoris* FDH) heat-dried cells (2 g, 130 U FDH) and *P. pastoris* SMD 1168 (expressing *T. intermedius* PDH) heat-dried cells (1.954 g, 110 u FDH) are added to the stirred solution. After 5 to 10 min when the cells are dispersed by the stirrer, the pH is brought back to 8 by addition of concentrated ammonium hydroxide solution. After 8 h, a small addition of 99% formic acid is needed to adjust the pH from 8.3 to 8.0. Thereafter the pH is expected to rise to about 8.6 after 23 h. Alternately, a more tightly covered vessel is used to prevent the pH from rising above 8. The pH rise on the 20 g scale is attributable to the loss of $CO_2$ from the more open 1-1 reactor. When the conversion of 1c to 2c is complete, as judged by HPLC, cells are removed by vacuum filtration after 5% (w/v) celite admix and precoat. The solution is then passed through a 10,000 MW cutoff membrane to screen out large molecular weight solubles, such as proteins. Loss of 2c across these two filtration steps is expected to range from 5 to 10%.

For scaleup, the reaction is run at the same reagent concentrations in a 5000 l tank maintained at 40° C. and stirred at 80 rev/min for about 27 h. Cells and protein are removed via crossflow microfiltration using a ceramic crossflow microfilter fitted with 0.2 micron porosity ceramic cartridges totaling nearly 7.4 square meters of filtration area. Protein removal is accomplished via crossflow filtration using a 9.3 $m^2$ of spiral wound 10,000 MW cutoff membrane.

Reactions with immobilized enzymes: Recombinant *E. coli* (8 g) in 32 ml 1 M potassium phosphate buffer, pH 7, containing 6 g of sodium formate, is disrupted by sonication, heated for 15 min at 60° C., clarified by centrifugation and mixed with 3 g Eupergit C(Röhm Pharma, Darmstadt, Germany) for 42 h. The resin is filtered and washed with 1 M potassium phosphate buffer, pH 7.5; and at least 40.6% of the activity is expected to be recovered on the resin. Recombinant *P. pastoris* in 60 ml 1 M potassium phosphate buffer, pH 7, is disrupted by sonication, heated for 30 min at 60° C., clarified by centrifugation and mixed with 5 g of Eupergit C250L (Röhm Pharma) for 72 h. The resin is filtered and washed with 1 M potassium phosphate buffer, pH 7, and at least 17.7% of the activity is expected to be recovered on the resin. The reactions contain in a volume of 100 ml: 1c (5.0 g, 25.8 mmoles), ammonium formate (1.754 g, 27.8 mmoles), dithiothreitol (16.4 mg, 0.106 mmoles), NAD (70.5 mg, 0.103 mmoles), recombinant FDH immobilized on Eupergit C L (4.35 g, 166.5 units), and recombinant PDH immobilized on Eupergit C250 L (7.29 g., 27.5 units). pH is adjusted to 8.0 with $NH_4OH$ and formic acid. Reactions are run in a jacketed reactor maintained at 40° C. At the end of each reaction, the solution is drained from the reactor through a stainless steel sieve, 80/400 mesh, which retained the immobilized enzymes.

Isolation Of 2c: Enzymatic reductive amination of 987 g of 1c is expected to yield 32.3 L of a solution containing 771 g of 2c. The solution is sparged with nitrogen while the pH is adjusted with 30% acetic acid (885 ml) until stable at 6.5. To make the calcium concentration 20 mM in excess of oxalate present (0.2 mM), 740 ml of 1 M $CaCl_2$ is added. The mixture is stirred and heated at 55–61° C. for 1 h and then cooled to room temperature. The solution is concentrated in vacuo (50 mm Hg, 58–61° C. bath temperature, and vapor temperature at 38° C.) to 8.8 kg, warmed to 38° C., and filtered, washing the solids with water. One third of the filtrate (2.92 kg) is further concentrated at 50 mm Hg to 1.61 kg. At this concentration (approximately 160 g/L), the product crystallizes. While being stirred, the warm mixture (40° C.) is diluted with 6.44 L of methanol and then held at 2–4° C. for 2 h. The product is filtered out, washed with 1.6 ml of cold methanol, and dried in vacuo at 50° C. to give an expected yield of 212.9 g of 2c. Isolation of 2c from the remaining filtrate in the same way is expected to yield 423.5 g for a total first crop yield of 636.4 g with a purity of 98.3%.

The combined mother liquors and washes are concentrated to 1.27 kg, warmed to 61° C., and filtered to remove a small amount of insoluble material. The filtrate is further concentrated to 1.20 kg, mixed with 4.8 L of methanol, held at 60° C. for 1 h, and then at 1–5° C. for 1 h. The product is filtered out, washed with 1.2 L of cold methanol and dried in vacuo at 50° C. to give an expected yield of 74.5 g of 2c with a purity of 97.7%. The recovery of 2c is expected to be 90.5% and the yield from 1c is expected to be 82.2%.

NMR chemical shifts, δ, are reported in ppm downfield from internal 3-(trimethylsilyl)propionic-2,2,3,3,-$d_4$ acid, sodium salt. Expected values are: IR (KBr) 2873, 2139, 1581, 1513, 1406, 1319, 1145, 1061, 944, 818, 658, 518 $cm^{-1}$; $^1H$ NMR (400 MHz, $D_2O$) δ 1.50 (m, 2H), 1.75 (m, 2H), 1.90 (m, 2H), 3.74 (t, 1H), 3.98 (m, 4H), 5.05 (t,1H); $^{13}C$ NMR (101 MHz, $D_2O$) δ 21.92, 33.12, 35.06, 57.47, 67.44, 104.94, 175.87.

HPLC methods: Samples are diluted with water and heated in a boiling water bath for 1 min to stop the reaction and precipitate proteins, and then assayed with a Hewlett-Packard 1090 HPLC. Amount and optical purity of 2c is assayed with a Chiralpak WH 25×0.46 cm column (Daicel Chemical Industries, Ltd., Tokyo, Japan) using 0.3 mM $CuSO_4$ mobile phase, 1 ml/min flow rate, 40° C. column temperature, 230 nm detection, and 20 μl injection volume. Retention times are: L-enantiomer 28.044 min, D-enantiomer 23.842 min. Retention times are expected to decrease with use of column and changed with concentration of samples. Keto acid acetal 1c is assayed with a YMC ODS-A, 5 micron, 4.6×150 mm column (YMC, Inc., Kyoto, Japan) using a mobile phase of 0.055 M $KH_2PO_4$, adjusted to pH 4.0 with phosphoric acid, 1 ml/min flow rate, ambient temperature, 210 nm detection, and 10 μl injection volume. Retention time of 1c is about 25 min.

Example 6

Enzymatic Assay for Serum Formate Using Recombinant *P. pastoris* FDH

The following experiments (adapted from S. Grady and J. Osterloh, 1986, *J. Anal. Toxicol.* 10:1–5) employ *P. pastoris* FDH in enzymatic assays for serum formate. Formate is a toxic metabolite produced following methanol poisoning (G. Martin-Amat et al., 1978, *Toxicol. Appl. Pharmacol.* 45:201–205; K. E. McMartin et al., 1980, *Am. J. Med.* 63:414–418; S. Shahangian et al., 1984, *Clin. Chem.* 30:1413–1414; D. H. Morton et al., 1983, *Vet. Hum. Toxicol.* 25:281).

Reagents: Lyophilized nicotinamide adenine dinucleotide-diaphorase (NAD-diaphorase), p-iodonitortetrazolium violet (INT), formate dehydrogenase, and sodium formate are all obtained from Sigma Chemical Co. Acetonitrile, $Na_2HPO_4$, and $KH_2PO_4$ are of analytic grade, and reverse osmosis-deionized water is used. Phosphate buffer (100 mmol/L, pH 6.0) is prepared by mixing 100 mmol/L $KH_2PO_4$ and 100 mmol/L $Na_2HPO_4$ (5:1). Buffered NAD-diaphorase is prepared by adding 150 ml of buffer to one bottle of lyophyhlized NAD-diaphorase (Sigma). Buffered NAD-diaphorase-INT is prepared by addition of 140 mg INT (Sigma) to 140 ml of buffered NAD-diaphorase, and recombinant *P. pastoris* FDH is lyophilized. Specific activity of the *P. pastoris* FDH is 0.4 to 1.0 unites/mg solid (0.4 to 1.8 units/mg protein). Portions (5 to 15 mg) are weighed into 1.5 ml glass vials and stored at −70° C. One vial is used for each batch analysis. Each is reconstituted with about 100 to 200 μl/mg buffered NAD-diaphorase (5° C.) and kept in an ice bath during analysis. Serum and aqueous standards (10 ml each) are supplemented with stock aqueous sodium formate solutions containing 10.0 or 1.0 g/L to produce concentrations ranging from 0 to 400 mg/L with less than 1% volumetric alteration of the matrix. Working reagent and final reaction (cuvette) concentrations are shown in the table, below.

| Reagent | Commercial form | Working conc. | Cuvette conc. |
|---------|-----------------|---------------|---------------|
| NAD | lyophilized | 1.51 mmol/L (1 g/L) | 1.43 mmol/L |
| Diaphorase | lyophilized | 800 U/L | 759 U/L |
| INT | analytic grade powder | 2.10 mmol/L (1 g/L) | 1.99 mmol/L |
| FDH | lyophilized | 5400 U/L | 102 U/L |
| formate | sodium salt | 0–8.89 mmol/L (0–400 mg/L) | 0.014 mmol/L |

Procedure: Serum samples and standards (100 μl) are vortexed (5 sec) with 100 μl acetonitrile in 1.5 ml polypropylene centrifuge tubes and centrifuged (14,000 g) for 2 min. Supernatants (100 ul) are added to 5 ml disposable plastic tubes containing 3.0 ml buffered NAD-diaphorase-INT. After mixing, 60 μl of P. pastoris FDH (5 U/ml at 5° C.) is added. These are mixed and left at room temperature for 10 min. Each preparation is subsequently aspirated into the sipper-cuvette of a Stasar III (Gilford (CIBA-Corning Diagnostics, East Walpole, Mass.), or similar single-beam spectophotometer. The instrument is zeroed on water and absorbances are read at 500 nm. Absorbances vs. concentrations of the standards are plotted. A direct procedure is also used for this study, wherein 20 μl of serum is added to the NAD-diaphorase-INT.

Reaction completeness and end product stability are assessed by measuring the change in absorbance from 1 to 55 min after the addition of P. pastoris FDH. Absorbance readings are taken at 30 sec intervals with the spectophotometer connected to a CP 5000 Processor (Sylva Co.) for both direct and pretreated sample procedures at several concentrations. Calibration response is determined using supplemented aqueous and serum matrices. The absorbance vs. concentration is assessed by least squares linear regression. Calibration response (absorbance/mg/L, slope) is compared over a period of several months for both direct and acetonitrile pretreatment procedures. To assess recovery, additional formate is added to sera from patients overdosed on methanol to increase the concentration by 13 and 66 mg/L using the acetonitrile pretreatment procedure.

Sera containing formate (140 mg/L) is reassayed after supplementation with toxicologically significant concentrations of ethanol, methanol, or acetone (up to 5000 mg/L), with ethylene glycol (up to 100 mg/L), formaldehyde or acetaldehyde (up to 1000 mg/L), lactate (up to 900 mg/L, 10 mmol/L), and/or acetonitrile (up to 600 μl/reaction mix/tube). Clear, lipemic, icteric, and hemolyzed samples from non-poisoned patients are also assayed. For these specimens, only 40 μl of supernatant from acetonitrile pretreatment samples (containing 20 μl of serum) and 20 μl of serum added directly are used so that equal sample sizes will be compared.

Sera supplemented with 5, 10, 15, 25, and 140 mg/L are assayed in the acetonitrile pretreatment protocol for within-run precision. Frozen (−70° C.) supplemented sera are assayed 25 and 140 mg/L) on 12 occasions over a three-month period for between-run precision. To estimate the accuracy of the new procedure, seven samples from actual methanol overdoses representing a range 0 to 257 mg/L are assayed and sent for commercial analysis by headspace gas chromatography (GC) followed by the formation of methyl formate derivatives.

Buffered NAD-diaphorase and buffered NAD-diaphorase-INT is stored at 20 to 8° C. After 6 weeks, slopes and intercepts are compared by performing standard curves for stored and freshly prepared reagents. Buffered NAD-diaphorase is also reassessed after an additional 13 weeks of storage at 20 to 8° C.

Figure 4:
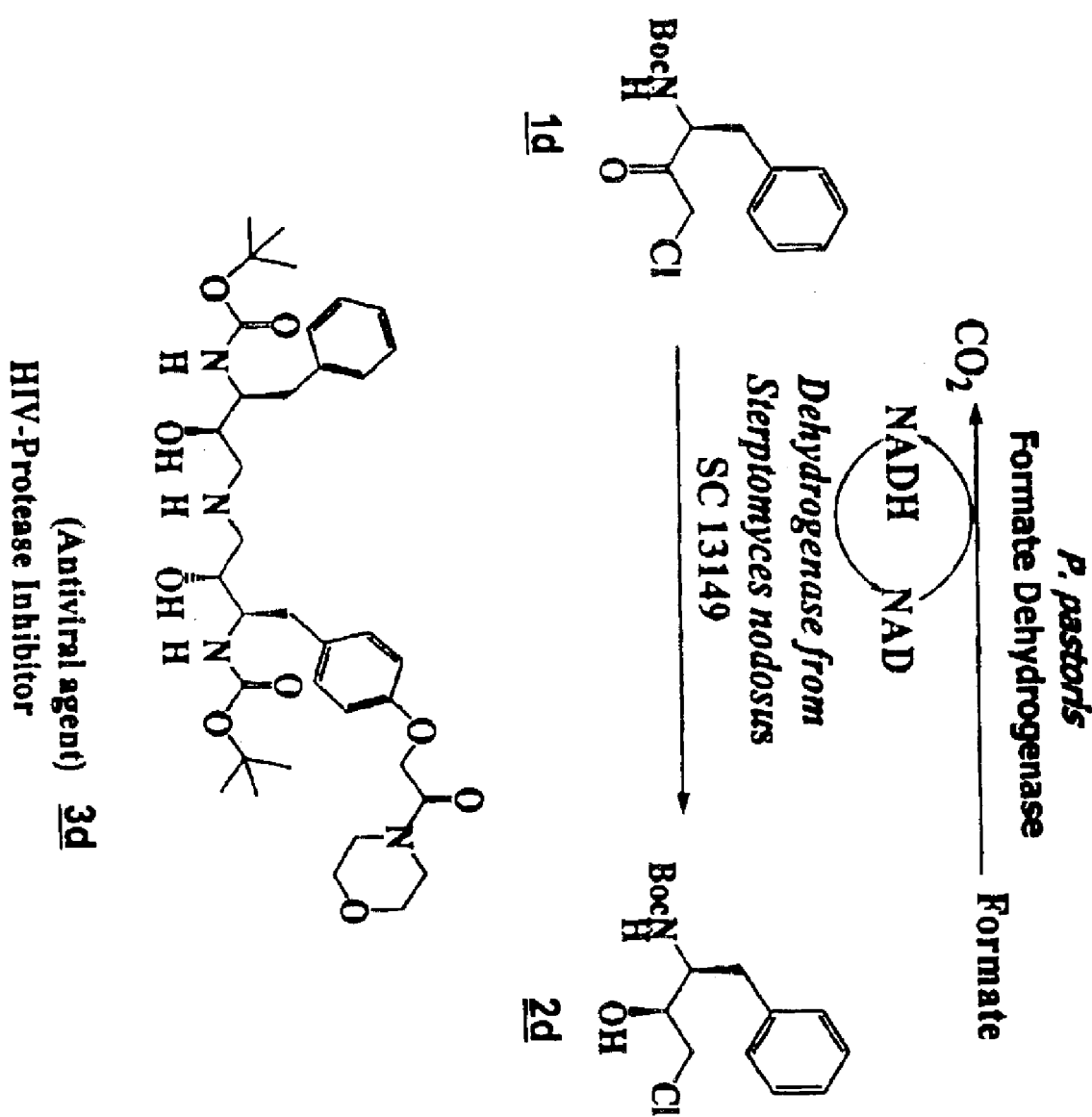
FIG. 4 illustrates the use of *P. pastoris* FDH in the chiral synthon for a HIV protease inhibitor (adapted from R. N. Patel et al., 1997, *Tetrahedron: Asymmetry* 8:2547–2552). 1d represents N-P-α-amino chloroketone; 2d represents the corresponding chiral alcohol; 3d represents a HIV protease inhibitor (J. C. Barrish et al., 1994, *J. Med. Chem.* 37:1758–1771).

Example 7
Reduction Reaction for N-protected α-Aminochloroketone Using P. pastoris FDH The following experiments (adapted from R. N. Patel et al., 1997, Tetrahedron: Asymmetry 8:2547–2552) employ P. pastoris FDH in the stereoselective reduction of N-P-α-amino chloroketone 1d (FIG. 4) to produce the corresponding chiral alcohol 2d (FIG. 4). The chiral alcohol is key intermediate in the synthesis of a HIV protease inhibitor (J. C. Barrish et al., 1994, J. Med. Chem. 37:1758–1771). The reduction reaction includes: 1) P. pastoris formate dehydrogenase; 2) NAD+; 3) N-P-α-amino chloroketone; 4) formate; and 5) aminochloroketone dehydrogenase.

Materials and methods: Starting substrate 1d and reference compound 2d are synthesized in the Chemical Process Research Department, Bristol-Myers Squibb Pharmaceutical Research Institute as described previously (Barrish et al., 1994, J. Med. Chem. 37:1758–1771). The physicochemical properties including spectral characteristics ($^1$H-NMR, $^{13}$C-NMR, Mass spectra) are checked to be in full accord for all these compounds. The proton magnetic resonance ($^1$H-NMR) and carbon magnetic resonance ($^{13}$C-NMR) are recorded on a Brucker AM-300 spectrometer.

Microorganisms: Streptomyces nodosus SC 13149, Pullularia pullulans SC 13849, Candida boidinii SC 13821, Nocardioides albus SC 13910, Mortierrella ramanniana SC 13850, Caldariomyces fumigo SC 13901 are obtained from the American Type Culture Collection, Rockville, Md. Microbial cultures are stored at −90° C. in vials.

Growth of microorganisms: For screening purposes, one vial of each culture is used to inoculate 100 ml of medium A containing 1% malt extract, 1% yeast, 2% glucose, and 0.3% peptone. The medium is adjusted to pH 6.8 before sterilization. Cultures are grown at 28° C. and 280 RPM for 48 hr. Cultures are harvested by centrifugation at 18,000×g for 15 min, washed with 0.1 M potassium phosphate buffer pH 7.0, and used for reduction studies.

Reduction of 1d by cell-suspensions: Cells of various microorganisms expressing recombinant P. pastoris FDH and endogenous aminochloroketone dehydrogenase are suspended separately in 100 mM potassium phosphate buffer (pH 7.0) at 20% (w/v, wet cells) cell concentration and supplemented with 1 mg/ml of 1d and 30 mg/ml of glucose. Reduction is conducted at 28° C. and 150 RPM. Periodically, samples of 1 ml are taken and extracted with 5 ml of tert.butylmethylether:toleune (60:40). After centrifugation, the separated organic phase is collected and dried with a nitrogen stream. The oily residue obtained is dissolved in 1 ml of ethanol, filtered through a 0.2 μm LID/X filter, and analyzed by HPLC.

Two-stage process for reduction of 1d: Streptomyces nodosus SC 13149 and Mortierella ramannina SC 13850 culture expressing recombinant P. pastoris FDH and endogenous aminochloroketone dehydrogenase are grown in a 25 L fermentor containing 15 L of medium A with 0.025% UCON antifoam (Union Carbide, Danbury, Conn.). Growth comprises several inoculum development stages and fermentation. Inoculum development includes F1 and F2 stages. In the F1 stage, a frozen vial of each culture is inoculated into 100 ml medium A in a 500 ml flask. Growth is carried out at 28° C. and 280 RPM for 48 hr on a rotary shaker. In the F2 stage, 10 ml of F1 stage culture is inoculated into 1 L medium A and incubated at 28° C. and 280 RPM for 24 hr. Fermentors containing 15 L medium A are inoculated with 1 L inoculum of each culture from a F2 stage. Fermentation is conducted at 25° C. and 500 RPM with 15 LPM (liter per min) aeration for 48 hr. After 48 hr, cells are collected and stored at −90° C. until further use. About 1 kg of wet cell pastes is collected from each fermentation.

Frozen cells from the above batches are used to conduct the reduction of 1d in a 5 L reactor. Cell suspensions (10% w/v, wet cells) in 3 L 0.1 M potassium phosphate buffer (pH 6.0) are used. Compound 1d (3 g) and glucose (30 g) are added to the reactor and the reduction is carried out at 28° C. and 160 RPM with 1 LPM aeration for 24 hr. The pH is maintained between 6.6 and 6.8. Periodically, samples are prepared as described above and analyzed by HPLC to determine the percent conversion of 1d to 2d. The diastereomeric purity and the optical purity of 2d are determined by HPLC.

Single-stage process for reduction of 1d: *Streptomyces nodosus* SC 13149 culture expressing recombinant *P. pastoris* FDH and endogenous aminochloroketone dehydrogenase is grown in a 25 L fermentor as described above. After a 30 hr growth period, 15 g of ketone 1d is added to the fermentor and the biotransformation process is continued for 48 hr. The pH is maintained at 6.8 during biotransformation. Periodically, samples are prepared as described above and analyzed by HPLC to determine the percent conversion of 1d to 2d. The diastereomeric purity and the optical purity of 2d is determined by HPLC.

Isolation of 2d: At the end of a single-stage bioreduction, 12 L reaction mixture is extracted with 24 L of tert.butylmethylether:toluene (60:40). The separated organic phase (20 L) is washed with 10 L 0.1 M sodium chloride, dried over anhydrous sodium sulfate, and evaporated under reduced pressure to obtain a projected yield of 7.5 g crude product. This is recrystallized from ethyl acetate to obtain a projected yield of 6.5 g (62% overall yield) of white needle crystals of 2d. The diastereomeric purity and the optical purity of the isolated chiral alcohol 2d are expected to be >99% and >99.8%, respectively. $^1$H-NMR (CDCl$_3$) d 1.4 (S, 9H), 2.9 (d, 2H, J=13 Hz), 3.2 (S, 1H); 3.6 (m, 2H), 3.85 (m, 1H), 4.5 (S, 1H), 7.2–7.4 (m, 5H. MS m/z 302 (M+H)+ (calcd for C$_{15}$H$_{22}$ClNO$_2$, 301).

Analytical methods: Analysis of 1d and 2d are carried out using a Hewlett Packard HPLC. A YMC-PACK-ODS-A column (100×4.5 mm, ID 5 m) is used under the following conditions. Mobile phase is 10% methanol (solvent A) and 90% methanol (solvent B) used in a gradient as follows:

| Time (min) | Solvent A (%) | Solvent B (%) |
|---|---|---|
| 0 | 100 | 0 |
| 25 | 25 | 75 |
| 25.2–30 | 100 | 0 |

The flow rate is 1 ml/min and the detection wavelengths are 224, 250 and 280 nm. The retention times for substrate 1d and compound 2d are 24 min and 23.5 min, respectively. The optical purity of chiral alcohol 2d is determined by chiral HPLC. A Bakerbond chiralpak AD column (100×4.5 mm, ID 5 m; Mallinckrodt Baker Inc., Phillipsburg, N.J.) is used at ambient temperature; injection volume is 10 μl; mobile phase is 97.5% hexane:1% cyclohexanol:1.5% ethyl acetate mixture; flow rate is 0.8 ml/min; and detection wavelength is 210 nm. The retention time for the compounds 2d is 14 min.

Example 8

Figure 5:
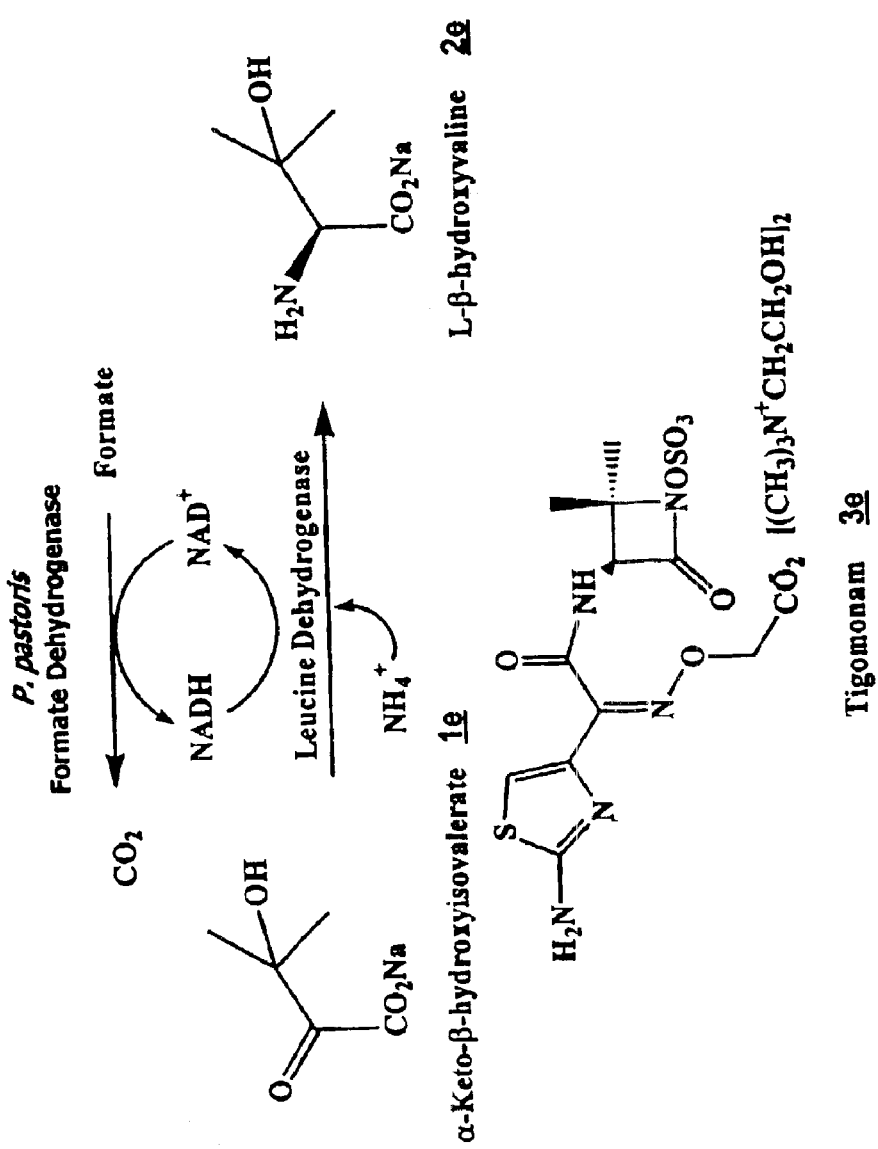
FIG. 5 illustrates the use of *P. pastoris* FDH in the chiral synthon for tigemonam (adapted from R. L. Hanson et al., 1990, *Bioorg. Chem.* 18:116–130). 1e represents α-keto-β-hydroxyisovalerate; 2e represents L-β-hydroxyvaline; 3e represents monobactum antibiotic tigemonam.

Reductive Amination Reaction of α-keto-β-hydroxyisovalerate Using *P. pastoris* FDH The following experiments (adapted from R. L. Hanson et al., 1990, *Bioorg. Chem.* 18:116–130) employ *P. pastoris* FDH in the stereoselective reductive amination of α-keto-β-hydroxyisovalerate 1e (FIG. 5) to produce L-β-hydroxyvaline 2e (FIG. 5). L-β-hydroxyvaline is a key intermediate required for the synthesis of the monobactam antibiotic, tigemonam (E. M. Gordon et al., 1982, *J. Amer. Chem. Soc.* 104:6053–6060; W. L. Parker et al., 1988, *Chem. Abstr.* 109:116074a; U.S. Pat. No. 4,751,220; W. H. Koster et al., 1985, 25$^{th}$ *Intersci. Conf. Antimicrobial Agents and Chemotherapy*, Abstract 368, September; W. A. Slusarchyk et al., 1986, *Tetrahedron Lett.* 27:2789–2792; C. Yoshida et al., 1985, *J. Antibiot.* 38:1536–1549). The reductive amination reaction includes: 1) *P. pastoris* formate dehydrogenase; 2) NAD+; 3) α-keto-β-hydroxyisovalerate; 4) formate; and 5) leucine dehydrogenase.

Chemical synthesis and isolation: A solution of β-hydroxyvaline (16 ml, ~353 mmol obtained by enzymatic reductive amination) is boiled for 2 min, centrifuged to remove protein, and then chromatographed over Dowex-50H$^+$ in a column (3×13.5 cm) (Dow Chemical Co., Midland, Mich.). The material is eluted with H$_2$O (250 ml) and 1 M NH$_4$OH (250 ml) and fractions (25 ml each) are monitored by TLC (silica gel, EtOAc:EtOH:AcOH:H$_2$O, 5:2:1:1; R$_f$ of 2e 0.21). Homogeneous fractions are combined and water is evaporated on a rotary evaporator. The residue is dissolved in water (25 ml) and evaporated under vacuum. This process is repeated two more times. The product is redissolved in water (25 ml) and lyophilized to give an expected yield of 0.593 g (54%) of 2e as a light brown solid. The product is projected to contain ~0.5 mol H$_2$O by KF analysis. The sample is dried over P$_2$O$_5$ at 40° C. under vacuum for 4 h, mp 202° C. dec.

Ir (KBr): v (C=O), 1611 cm$^{-1}$; $^1$H NMR (D$_2$O): δ, 1.15 (s, 3H), 1.38 (s, 3H), 3.5 (s, 1H) ppm; $^{13}$C NMR (D$_2$O): δ, 24.3, 28.3, 64.4, 70.8, 173.1 ppm; [α]D+3° (c=3.5, (H$_2$O); +11.9° (c=1.3, 6 N HCl).

Bacterial strains and growth conditions: *Bacillus* strains are obtained from the American Type Culture Collection as listed in the table, below.

| Strain | Number |
|---|---|
| B. subtilis | SC 13794[1] |
| B. subtilis | SC 10253 |
| B. subtilis | SC 8548 |
| B. megaterium | ATCC 39118 |
| B. megaterium | SC 3593[1] |
| B. megaterium | SC 6394[1] |
| B. megaterium | SC 6423[1] |
| B. megaterium | SC 6446[1] |
| B. megaterium | SC 3781 |
| B. megaterium | SC 3782 |
| B. stearothermophilus | ATCC 12980[2] |
| B. stearothermophilus | ATCC 7953[2] |
| B. sphaericus | ATCC 4525 |
| B. spaericus | SC 3574 |
| B. cereus | ATCC 14579 |
| B. cereus | SC 12147 |
| B. cereus | SC 10856 |
| B. pumilus | SC 11128 |
| B. pumilus | SC 8513 |
| B. licheniformis | SC 12148 |
| B. licheniformis | SC 11075 |
| B. circulans | SC 12999 |
| B. circulans | SC 10275 |

-continued

| Strain | Number |
| --- | --- |
| B. polymyxa | SC 1522 |
| B. thuringiensis | SC 2928 |
| B. brevis | SC 3812 |
| B. coagulans | SC 9261 |
| B. alvei | SC 9230 |

[1]L-β-Hydroxyvaline is assayed after 68 h.
[2]Cells are grown and incubations are carried out at 55° C.

For screening purposes, 1 ml of each culture is used to inoculate 100 ml of medium containing per liter: tryptone (17 g), soytone (3 g), NaCl (5 g), glucose (2.5 g), yeast extract (1 g), and $K_2HPO_4$ (2.5 g). The medium is adjusted to pH 7 with HCl. After 16 h of growth at 30° C., cells are collected by centrifugation, washed with 0.1 M potassium phosphate, pH 7, and resuspended in 5 ml of this buffer. Bacteria are disrupted by sonication and 0.2 ml samples are evaluated in two 1 ml reaction systems for synthesis of L-β-hydroxyvaline: Systems A and B. System A: 1 M $NH_4Cl$, 1 M glucose, 2 mM NAD, and 0.1 M α-keto-β-hydroxyisovalerate; System B: 1 M ammonium formate, 2 mM NAD, 0.1 M α-keto-β-hydroxyisovalerate, and 40 U/ml formate dehydrogenase from P. pastoris. Reactions are run at 30° C. for 48 h except as noted in the table, above, and initial pH is 8.2.

For preparative purposes, B. sphaericus ATCC 4525 is grown at 30° C. in a 250 L fermentor to the end of log phase on medium containing per liter: yeast extract (20 g), glucose (10 g), and $K_2HPO_4$ (2 g). The medium is adjusted to pH 7. Bacteria in 10 mM potassium phosphate buffer, pH 7, containing 0.01% mercaptoethanol are disrupted by sonication. The sonicate is partially purified by heating for 20 min at 60° C. followed by centrifugation for 10 min at 28,000 g. The supernatant is stored at −20° C. and used as a source of leucine dehydrogenase.

Enzyme assays and reactions: Activity of leucine dehydrogenase is determined in a system that included in 1.0 ml: α-keto-β-hydroxysovalerate or α-ketoisovalerate, 0.75 M $NH_4C$—$NH_4OH$ buffer, 0.3 mM NADH, and 3 to 10 μl cell extract. Absorbance decrease at 340 nm is monitored. All components except the keto acid are added and a blank value of rNADH oxidation is measured before the reaction is started by the addition of keto acid.

The glucose dehydrogenase assay used for screening strains contain in 1.0 ml: 0.5 M glucose, 3 mM NAD, 0.1 M Tris-Cl, pH 8, and 10 μl sonicated cell extract. For determining optimum pH, 0.75 M $NH_4OH$ buffer is substituted for Tris. The reaction is started by addition of enzyme, and absorbance increase at 340 nm is monitored. Protein levels are determined by the dye-binding method of Bradford (M. M. Bradford, 1976, Anal. Biochem. 72:248–254) using bovine serum albumin as standard.

Preparative reactions with glucose dehydrogenase and leucine dehydrogenase are run in an initial volume of 16 ml at pH 8.5 and 30° C. The pH is maintained by addition of 3 M $NH_4OH$ with a Brinkmann pH stat (Brinkmann, Brinkman Instruments, Westbury, N.Y.). Reactions contain 0.1 to 0.5 M α-keto-β-hydroxyisovalerate, 1 M glucose, 0.2 M $MN_4Cl$, 0.5 mM NAD, 0.01% mercaptoethanol, 44 U leucine dehydrogenase from B. sphaericus ATCC 4525, and 29 U glucose dehydrogenase from B. megaterium.

HPLC analysis: Samples are diluted with water and heated in a boiling water bath for 2 min to stop the reaction and precipitate proteins. L-β-hydroxyvaline is assayed with a Hewlett-Packard 1090 HPLC equipped with a diode array detector. A Bakerbond Chiralpak WH 25×0.46-cm column is used (Bakerbond, Mallinckrodt Baker Inc., Phillipsburg, N.J.). Injection volume is 20 μl, mobile phase is 0.3 mM $CUSO_4$, flow rate is 1.5 ml/min, temperature is 45° C., and detection wavelength is 230 nm. The standard is racemic β-hydroxyvaline.

Example 9

Purification of G. Oxydans 2-Ketoreductase

Fermentation: Gluconobacter oxydans (SC13851) was grown on a glycerol-containing medium as follows. Cultures were grown in 500 ml Erlenmeyer flasks for 24 hr in 100 ml medium A (5% glycerol, 0.5% yeast extract, 0.05% ammonium sulfate, 0.3% peptone, 0.05% $K_2HPO_4$, 0.02% $MgSO_4 \cdot 7H_2O$, 0.001% NaCl, 0.001% $FeSO_4 \cdot 7H_2O$, and 0.001% $MnSO_4 \cdot 7H_2O$). After 24 hr, the flask cultures were used to inoculate (1% v/v inoculum) a 15 L fermentor containing medium A. The fermentation was carried out at 28° C. for 24 hr. A 4000 L fermentor (Expend Industries, Inc., Brooklyn, N.Y.) was inoculated with 10 L inoculum from the 15 L fermentor. The 4000 L fermentor contained medium A with 0.05% antifoam SAG 5693. The fermentor was operated at 28° C., 100 LPM airflow, 690 mbar pressure, and 620 rpm agitation for 48 hr.

Cell recovery: The fermentor broth was cooled to 8° C. at the harvest. The tank was pressurized to 15 psig and broth was diverted to a Sharples (Alfa Laval Separation, Inc., Warminster, Pa.) centrifuge running at 18,000×g. The broth was processed at 3.2 L/min and recovered cells were stored at −70° C. until further use.

Purification of 2-ketoreductase: All the purification steps were carried out at 4° C. Forty-four grams of cells were suspended in 0.3 L buffer A (50 mM Tris-HCl, pH 7.5,1 mM $CaCl_2$, and 1 mM $MgCl_2$). After 30 min of homogenization, the cell suspension was passed through a microfluidizer (Microfludics International Corporation, Newton, Mass.) twice at 12,000 psi. The supernatant obtained by centrifugation (at 30,000×g for 30 min) was loaded onto DEAE cellulose column (400 ml) (Whatman, Maidstone, England), which was pre-equilibrated with buffer A. The enzyme activity was eluted with a 0 to 0.8 M NaCl gradient in buffer A.

The active fractions were pooled, and ammonium sulfate at 132 g/L was added before loading onto a phenylsepharose column (350 ml), which was pre-equilibrated with buffer A containing 1 M ammonium sulfate. The column was then washed with buffer A containing 1 M ammonium sulfate and the enzyme was eluted with a 1 M to 0 M ammonium sulfate gradient (total volume, 1.2 L). The fractions containing the active enzyme were pooled (150 ml) and concentrated with an Amicon YM-30 membrane (Amicon, Beverly, Mass.) to 8 ml.

The enzyme was then loaded onto a Sephacryl S-200 gel-filtration column (400 ml column) (Pharmacia, Piscataway, N.J.). The enzyme was eluted with buffer A containing 0.1 M NaCl with a flow rate of 0.8 ml/min. The active fractions from the gel-filtration column were pooled, and then loaded onto a mono Q ion-exchange (BioRad Q2) column (Bio-Rad, Hercules, Calif.). The enzyme activity was eluted with a 0 to 0.8 M NaCl gradient in buffer A.

The fractions containing the active enzyme were pooled (5.6 ml) and concentrated with a Centricon-30 membrane to 0.6 ml. The enzyme was then loaded onto a Superdex-75 gel-filtration column (FPLC; Pharmacia) and eluted with buffer A containing 0.1 M NaCl. The enzyme present in fraction 14 was analyzed by sodium dodecyl sulfate-polyacrylamide (SDS-PAGE) electrophoresis. This analysis indicated that the enzyme was present as a single band on the gel with a calculated molecular weight of 29 kilodaltons.

Example 10

Analysis of Purified *G. Oxydans* 2-Ketoreductase

Protein assay: The Bio-Rad protein assay was used to determine protein concentration. The assay was performed according to the manufacturer's protocol (Bio-Rad). Samples containing 1–10 μl of enzyme fraction were brought to a volume of 0.8 ml with water. Next, 0.2 ml of the Bio-Rad reagent was added to the 0.8 ml sample solution. This was mixed thoroughly. The absorbance of the solution was measured at 595 nm. The protein concentration (mg/ml) was calculated from the standard curve using bovine serum albumin as standard protein.

Enzyme activity units: One unit (U) of enzyme activity was defined as one micromole of S-2-pentanol formed in 1 hr under the conditions described above. Results from the protein analysis of *G. oxydans* 2-ketoreductase are summarized in the table, below.

| Steps | Volume (mL) | Enzyme Activity (Units) | Protein (mg) | Sp. Activity (Units/mg) | S-2-Pentanol (e e) | Purification Fold |
|---|---|---|---|---|---|---|
| Cell extract | 300 | 390.00 | 729.00 | 0.50 | | 1.00 |
| DEAE Cellulose | 180 | 235.80 | 185.40 | 1.27 | | 25.40 |
| Phenylsepharose | 150 | 186.00 | 72.00 | 2.58 | | 51.60 |
| Amicon concentration | 10 | | | | | |
| Sephacryl S200 Gel filtratio | 22 | 27.28 | 4.40 | 6.20 | >99 | 124.00 |
| Mono Q column | 5.6 | 35.39 | 3.64 | 9.72 | | 194.40 |
| Centricon concentration | 0.25 | | | | | |
| Sephadex-75 Gel filtration | 0.75 | 13.28 | 0.90 | 14.76 | >99 | 295.20 |

2-Pentanone reduction assays were carried out using both resting cells and the cell extract (soluble enzyme) of *Gluconobacter oxydans*.

Whole cell assays: Three grams of wet cell paste were suspended in 15 ml buffer containing 0.1 M Tris-HCl, pH 8, and 5 mM EDTA. The cell suspension was treated with 0.36 ml toluene. The treated cell suspension was shaken gently for 30 min in a 50 ml Erlenmeyer flask. The cells were then collected by centrifuging at 18,000×g for 20 minutes. Toluene treated cells (0.25 g) were suspended in 10 ml of 0.2 M Tris-HCl buffer pH 7.5, containing 10 mM $CaCl_2$ and 10 mM $MgCl_2$ in a 25 ml Teflon® flask. The following components were added to the reaction mixture: 7 mg $NAD^+$, 0.136 g sodium formate, 1.5 U formate dehydrogenase, and 0.025 ml 2-pentanone (Sigma, St. Louis, Mo.). The reaction mixture in the flask was incubated in a shaker at 28° C. with agitation at 200 rpm. At various time points (2–18 hr), samples containing 0.5 ml of reaction mixture were removed, and 2 ml of ethyl acetate was added to each sample to stop the reaction. The organic layer was separated by centrifugation and was used to analyze both the substrate and product.

Soluble enzyme assays: Samples of the enzyme were incubated in a reaction mixture (5 ml) containing 0.35 mg $NAD^+$, 68 mg sodium formate, 0.75 U formate dehydrogenase, and 5 mg 2-pentanone. Reactions were carried out in a Teflon® flask at 28° C. on a shaker at 200 rpm. After 18 hr, the reactions were quenched with 10 ml of ethyl acetate and analyzed by gas chromatography.

Analysis of enantiomeric alcohols by gas chromatography: Samples were extracted in ethyl acetate and dried over anhydrous magnesium sulfate. Samples were then applied onto a Astec Chiraldex G-TA, gamma cyclodextrin column (20m×0.25 mm×0.125 μm thickness; Astec, Whippany, N.J.) equipped with a guard column (Hewlett-Packard Ultra II, 5% phenyl methyl silicone, 5 m×0.32 mm×0.17 μm thickness; Agilent Technologies, Palo Alto, Calif.). The temperature of the injector was set at 150° C. and the detector of the chromatograph (Hewlett-Packard 5890) was set at 200° C. Detection was carried out with a flame ionization detector (Agilent Technologies). The separation was carried out by a gradient under the following conditions: 28° C. for 15 minutes, 5° C./min to 50° C. and hold 5 minutes. The helium flow rate was maintained at 22 cm/min. Under these conditions, the retention times for S-2-pentanol, R-2-pentanol, and 2-pentanone were 10.85, 11.67 and 17.84 minutes respectively.

Peptide Sequencing of the purified 2-ketoreductase: The purified protein was sent for N-terminal and internal peptide sequences to Argo BioAnalytica, Inc., Morris Plains, N.J. The following are the sequences obtained for the 2-ketoreductase.

N-Terminal Sequence
$NH_2$-Ser-Leu-Ser-Gly-Lys-Ile-Ala-Ala-Val-Thr-Gly-Ala-Ala-Gln-Gly-COOH (SEQ ID NO:16).
Internal Peptides
Peptide 1: $NH_2$-Lys-Arg-Met-Ala-Glu-Ile-Thr-Gly-Thr-Glu-Ile-COOH (SEQ ID NO:17); and Peptide 2: $NH_2$-Lys-Val-Glu-Ala-Leu-Gly-Arg-Arg-Ala-Val-COOH (SEQ ID NO:18).

Example 11

Identification of the *G. Oxydans* 2-Ketoreductase Gene

*Gluconobacter oxydans* (BMS Collection No. SC13851; ATCC No. 621) was grown in 50 ml LB medium (1% tryptone, 0.5% yeast extract, 0.5% NaCl) at 37° C. for 16 hr at 200 rpm in a shaker. The cells were harvested by centrifugation and the chromosomal DNA was prepared (see Ausubel et al. (Eds.), 1981, *Current Protocols in Molecular Biology*, vol.2, section 13.11.2, John Wiley and Sons, New York). Degenerate PCR primers based on internal peptides (oligo GO1: 5'-AAR GTI GAR GCI YTI GGI MGI MGI GCI GT-3'; SEQ ID NO:19; oligo GO 4: 5'-ATY TCI GTI CCI GTI ATY TCI GCC AT-3'; SEQ ID NO:20, where "Y"=C+T; "R"=A+G; "I"=deoxyinosine; and "M"=A+C), were used to amplify the gene using genomic DNA as template. The amplification conditions included incubation at 94° C. for 1 min, followed by 30 cycles at 94° C. for 0.5 min; 50° C. for 0.5 min; and 72° C. for 0.5 min using a Hybaid PCR Express thermocycler (ThermoHybaid US, Franklin, Mass.). The PCR fragments were electrophoresed at 60 V for 2 hr through a 0.8% agarose gel in TAE buffer (0.04 M Trizma base, 0.02 M acetic acid, and 0.001 M EDTA, pH 8.3) containing 0.5 μg/ml ethidium bromide. The 400 bp PCR Fragment was identified by comparison to a 1 kb Plus DNA ladder (Invitrogen) and excised using a scalpel. The DNA was isolated from the agarose using the QIAquick Gel Extraction Kit (QIAGEN, Chatsworth, Calif.). The resulting 400 base pair (bp) PCR fragment was cloned into pCR2.1™ using the TA Cloning kit (Invitrogen, Carlsbad, Calif.).

To isolate the complete 2-ketoreductase gene, G. oxydans chromosomal DNA was cleaved with restriction endonucleases BamHI, EcoRI, EcoRV, HindIII, NotI, PstI, SacI, SpaI, XbaI and XhoI under conditions recommended by the manufacturer (Promega, Madison, Wis.). Approximately 3 µg of each digested sample was electrophoresed at 20 v for 18 hr through a 0.8% agarose gel in TAE buffer (0.04 M Trizma base, 0.02 M acetic acid, and 0.001 M EDTA, pH 8.3) containing 0.5 µg/ml ethidium bromide. Fragments were transferred to a Hybond N+ nylon filter (Amersham Pharmacia, Piscatatway, N.J.) using a VacuGene blotting apparatus (Amersham Pharmacia). To identify the 2-ketoreductase gene, the 400 bp fragment was obtained by digesting the pCR2.1™ plasmid with EcoRI, labeled using PCR DIG Probe Kit (Roche Biochemicals, Indianapolis, Ind.), and the labeled fragment was used as a probe.

Hybridization to the filter containing G. oxydans chromosomal digests, washing, and detection were performed according to materials and directions supplied with the DIG High Prime DNA Labeling and Detection Starter Kit II (Roche Biochemicals). Stringent wash conditions carried out using 1×SSC (20×SSC is 173.5 g NaCl, 88.2 g NaCl, pH 7.0) and 0.1% sodium dodecyl sulfate at 68° C. A single hybridizing fragment was visible in all the endonuclease digests. A 4 kb BamHI fragment was chosen for further analysis. Approximately 10 µg of G. oxydans chromosomal DNA was digested using 25 U BamHI for 2 hr at 37° C. in a final volume of 0.1 ml with the buffer recommended by the manufacturer (Promega). The digested DNA was electrophoresed on a 0.8% agarose gel in TAE buffer at 20 V for 18 hr. Fragments between 3.8 and 4.5 kb were identified by comparison to a 1 kb Plus DNA ladder (Invitrogen) and excised using a scalpel.

The DNA was isolated from the agarose using the QIAquick Gel Extraction Kit (QIAGEN) and ligated to BamHI-cleaved pZero2 (Invitrogen, Carlsbad, Calif.) vector DNA in a 2:1 molar ratio in a total volume of 10 µL at 22° C. for 2 hr. Two microliters of ligated DNA was used to transform 0.04 ml competent E. coli DH10B cells (Invitrogen) by electroporation. SOC medium was immediately added (0.96 ml; SOC is, per liter, 0.5% yeast extract, 2% tryptone, 10 mM NaCl, 2.5 mM KCl, 10 mM $MgCl_2$, 10 mM $MgSO_4$, and 20 mM glucose). Cells incubated in a shaker for 1 hr at 37° C. and 225 rpm.

Cells were spread onto a 132 mm Hybond N+ membrane placed on top of LB kanamycin agar medium. Kanamycin was purchased from Sigma Chemical Co., and used at final concentration of 50 µg/ml. Cells were grown at 37° C. for 20 hr. Colonies were replicated onto two fresh filters placed on top of LB kanamycin agar medium and incubated at 30° C. for 16 hrs. Colonies were lysed in situ by placing the filters on a piece of Whatman 3MM paper saturated with 0.5 M NaOH for 5 min. The filters were dried for 5 min on Whatman paper, then neutralized on 3MM paper soaked in 1.0 M Tris-HCl, pH 7.5 for 2 min, and dried again for 2 min. Membranes were placed on top of 3MM paper saturated with 1.0 M Tris-HCl, pH 7.0/1.5 M NaCl for 10 min.

DNA was crosslinked to the filters by exposure to ultraviolet light in a Stratagene UV Stratalinker 2400 set to "auto crosslink" mode (Stratagene, LaJolla, Calif.). Cell debris was removed from the membranes by immersing in 3×SSC/ 0.1% SDS, wiping the surface with a wetted Kimwipe®, then incubating in the same solution heated to 65° C. for 3 hr with agitation. Filters were rinsed with $dH_2O$ and used immediately or wrapped in SaranWrap® and stored at 4° C. Hybridization, washing, and detection was performed as described above using the 400 bp G. oxydans 2-ketoreductase gene probe.

Eight putative hybridizing colonies were picked from the master plate, inoculated into SOC medium containing kanamycin, and grown at 37° C. for 24 hr at 250 rpm. These colonies were also tested for the presence of 400 bp fragment with GOI1 and GOI4 primers using the conditions described previously. Six of the eight colonies gave the expected PCR 400 bp fragment confirming the BamHI fragment contained at least a portion of the 2-pentanone reductase gene. Cells from one milliliter of cell culture from two selected colonies were pelleted by centrifugation. Plasmid DNA was isolated using the QIAprep Spin Miniplasmid Isolation Kit (QIAGEN). An aliquot of plasmid DNA was digested with BamHI to confirm the presence of the 4.0 kb fragment.

Example 12

Sequencing and Sequence Analysis of the G. Oxydans 2 Ketoreductase-gene

DNA sequencing of the 4.0 kb insert of 2-ketoreductase gene was performed at the Bristol-Myers Squibb sequencing facility. DNA sequencing of the 4.0 kb insert was carried out using the BigDye terminator kit and DNA Sequencing Unit, Model 377 (Applied Biosystems, Foster City, Calif.). The complete 2-ketoreductase nucleotide sequence and predicted amino acid sequence is shown in FIGS. 1F–1H. The coding region was determined to be 780 bp in length. The nucleotide sequence was determined to encode a 260-amino acid protein (MW=27,220 daltons). The G. oxydans 2-ketoreductase amino acid sequence showed significant homology to other dehydrogenases including acetoin dehydrogenase, L-2,3-butanediol dehydrogenase, sorbitol dehydrogenase, polyketide reductase, and glucose dehydrogenase. In addition, the N-terminus of G. oxydans 2-ketoreductase showed homology to a ribitoldehydrogenase from Klebsiell aerogenes (Loviny et. al., 1985, Biochem. J. 230:579–585).

A conserved domain search (CD-Search; http://www.ncbi.nlm.nih. gov/blast/Blast.cgi) indicated that G. oxydans 2-ketoreductase amino acid sequence included a short chain dehydrogenase domain (gnl|Pfam|pfam00106) extending though amino acid positions 4–255. In addition, BLAST 2.2.1 analysis (S. F. Altschul et al., 1997, Nucleic Acids Res. 25:3389–3402; http://www.ncbi.nlm.nih.gov/BLAST/) indicated that the amino acid sequence of the G. oxydans 2-ketoreductase shared 53% identity with the amino acid sequences of acetoin reductase and meso-2-,3-butanediol dehydrogenase from Klebsiella pneumoniae (GenBank Accession Nos. AAC78679 and BAA13085); 49% identity with the amino acid sequence of L-2,3-butanediol dehydrogenase from Corynebacterium glutamicum (GenBank Accession No. BAA36159); and 51% identity with the amino acid sequence of a putative short chain oxidoreductase from Streptomyces coelicolor (GenBank Accession No. T36396).

BLAST 2.2.1 analysis further indicated that longest stretch of identical contiguous amino acids shared by G. oxydans 2-ketoreductase and K. pneumoniae acetoin reductase was 9 residues in length. The longest stretch of identical contiguous amino acids shared by G. oxydans 2-ketoreductase and K. pneumoniae meso-2-,3-butanediol dehydrogenase was 8 residues in length. The longest stretch of identical contiguous amino acids shared by G. oxydans 2-ketoreductase and C. glutamicum L-2,3-butanediol dehydrogenase was 7 residues in length. The longest stretch of identical contiguous amino acids shared by *G. oxydans* 2-ketoreductase and *Streptomyces coelicolor* oxidoreductase was 11 residues in length.

The *G. oxydans* 2-ketoreductase nucleotide sequence did not show significant homology to previously identified enzymes. BLAST 2.2.1 analysis indicated that he longest stretch of identical contiguous nucleotides shared by *G. oxydans* 2-ketoreductase and other known nucleotide sequences was 20 bases in length.

Example 13
Subcloning and Expression of *G. Oxydans* 2-Ketoreductase in *E. Coli*

To facilitate PCR-based cloning of the 2 ketoreductase gene into expression vector pBMS2000 (disclosed in U.S. Pat. No. 6,068,991, issued May 30, 2000 to S. W. Liu et al.), oligonucleotide primers containing the 5' and 3' end of the gene along with compatible restriction endonuclease cleavage sites were prepared to include the following sequence:

```
5' ggaattccatatgtccctttctggaaaatcgc 3'   (5' end of gene; SEQ ID NO:21)
         NdeI 5' cgggatcctctcagcggaaaacg 3'           (3' end of gene; anti-sense; SEQ ID NO:22)
     BamHI
```

High-fidelity amplification of the 2-ketoreductase gene was carried out in four 25 µl aliquots, each consisting of 1×Z-Taq reaction buffer (PanVera Co., Madison, Wis.), 0.2 µM each deoxynucleotide triphosphate (dATP, dCTP, dGTP, dTTP), 0.4 nM each oligonucleotide, 2.5 U Z-Taq DNA polymerase (PanVera), and 10 pg plasmid DNA containing the cloned 2-ketoreductase gene. The amplification conditions included incubation at 94° C. for 4 min followed by 25 cycles of incubation at 94° C. for 1 min; 50° C. for 1 min; and 72° C. for 1.5 min using a Perkin-Elmer Model 480 thermocycler with autoextension. The PCR samples were electrophoresed on a 1.0% TAE agarose gel for 2 hr at 100 V. The 780 bp fragment containing the 2-ketoreductase gene was excised from the gel and purified using the QIAquick Gel Extraction Kit (QIAGEN).

The concentrations of the isolated DNAs were estimated by electrophoresis with the Low Molecular Weight DNA Mass Ladder (Invitrogen). Purified DNA was digested with 20 U NdeI for 2 hr at 37° C. in a total volume of 20 µl diluted to 40 µl with water. This was followed by digestion with 20 U of BamHI at 30° C. for 2 hr. The expression vector pBMS2000 was digested with these endonucleases in parallel. The digested samples were electrophoresed on a 1.0% TAE agarose gel for 2 hr at 100 V. The 800 bp and 4516 bp fragments containing the ketoreductase gene and plasmid DNA, respectively, were excised from the gel and purified using the QIAquick Gel Extraction Kit (QIAGEN).

The concentrations of the isolated DNAs were estimated by electrophoresis and comparison with Low Molecular Weight DNA Mass Ladder (Invitrogen). Ligation and transformation were carried out as described above. Cells containing plasmid were selected on LB agar containing 20 µg/ml neomycin at 37° C. for 20 hr. Plasmids with the desired insert were screened by colony PCR as described earlier. Neomycin-resistant colonies were picked using a disposable plastic inoculation needle, swirled into LB broth, and then transferred to LB-neomycin agar. PCR samples were electrophoresed on a 0.8% TAE agarose gel for 2 hr at 100 V. Seven samples out of ten showed a strong band at 800 bp. One colony containing this plasmid (named pBMS2000-KR) was chosen for further study. The cloned *G. oxydans* 2-ketoreductase gene was deposited at the American Type Culture Collection (ATCC), 10801 University Boulevard, Manassas, Va. 20110-2209 on Nov. 15, 2001 in *E. coli* cells as SC16469 under ATCC Accession No. PTA-3864 according to the terms of the Budapest Treaty.

The recombinant plasmid was transformed into *E. coli* strain BL21 (DE3) (Invitrogen, Carlsbad, Calif.) by electroporation. Transformed cells were selected on LB-neomycin agar medium, and individual colonies were inoculated into 10 ml MT3 medium (1.0% NZAmine A, 2.0% Yeastamin, 2.0% glycerol, 0.6% $Na_2HPO_4$, 0.3% $KH_2PO_4$, 0.125% $(NH_4)_2SO_4$, and 0.0246% $MgSO_4$) containing 30 µg/ml neomycin. The cultures were incubated at 28° C. at 250 rpm for 20 hr. Cultures were then diluted in fresh medium, grown to an $OD_{600}$ nm of 0.25, and then incubated under the same conditions until the $OD_{600}$ reached 0.8±0.1. IPTG was added to a final concentration of 0.3 mM and the cultures grown at the above conditions for 20 hr. Cells were pelleted by centrifugation (5,000×g) for 7 min.

The culture medium was removed, and cells were washed with an equal volume ice cold 50 mM $KPO_4$ buffer (pH 7.3) with 2 mM dithiothreitol. The cells were again pelleted, and the wet cell weight was recorded.

Example 14
Reduction of 2-Pentanone Using Recombinant 2-Ketoreductase

To demonstrate the utility of the recombinant enzyme, the cloned ketoreductase was used in the reduction of 2-pentanone to 2-pentanol. The reaction contained 0.18 mg NAD+, 30 mg sodium formate, 0.3 units formate dehydrogenase (Sigma, St. Louis, Mo.), 2 mg 2-pentanone, and 0.5 ml of extract from an *E. coli* (BL21(DE3)) culture containing the pBMS2000-KR plasmid and expressing the ketoreductase. Alternatively, *P. pastoris* formate dehydrogenase can be substituted for the commercial formate dehydrogenase. Cell extracts were obtained as follows: 2 g recombinant cells were suspended in 10 ml Buffer A (50 mM Tris-HCl, pH 7.5,1 mM $CaCl_2$, and 1 mM $MgCl_2$). The resuspended cells were sonicated for 2 min (20 sec pulse "on" and 30 sec pulse "off") using Model 550 Sonic Dismembrator (Misonix Inc., Farmingdale, N.Y.). The resulting mixture was centrifuged for 15 min at 8000 rpm at 4° C. The supernatant was removed and used for reduction reactions., The reactions were carried out in a culture tube at 28° C. with shaking at 200 rpm. After 16 hr, samples were quenched with 2 ml of ethyl acetate and analyzed by gas chromatography (described earlier). There was complete reduction of the substrate using recombinant enzyme, while no reaction took place in the absence of recombinant enzyme.

Example 15
Reduction of Other Alkylketones Using Recombinant 2-Ketoreductase

To demonstrate the utility of the recombinant enzyme in the reduction of other substrates, the cloned ketoreductase was used in the reduction of 2-heptanone, 2-octanone, and 2-decanone. The reactions contained 0.18 mg NAD+, 30 mg sodium formate, 0.3 units formate dehydrogenase (purchased from Sigma), 2 mg 2-ketones, and 0.5 ml of extract from the *E coli* culture containing the pBMS2000-KR plasmid and expressing the ketoreductase (described above). The reactions were carried out in a culture tube at 28° C. on a shaker at 200 rpm. The end of 16 hr, samples were quenched with 2 ml of ethyl acetate and analyzed by gas chromatography (described earlier). There was complete reduction of the substrates using recombinant enzyme as shown in the following table.

| Substrate | Product | % Conversion |
|---|---|---|
| 2-Heptanone | 2-Heptanol | >98 |
| 2-Octanone | 2-Octanol | >98 |
| 2-Decanone | 2-Decanol | >98 |

No reaction took place in the absence recombinant enzyme.

The experiments described in Examples 9–15 are also described in V. Nanduri et al.: U.S. Provisional Patent Application Ser. No. 60/341,933 filed Dec. 19, 2001 and U.S. patent application Ser. No. 10/320,104 filed concurrently herewith the contents of which are hereby incorporated by reference in their entirety.

As various changes can be made in the above compositions and methods without departing from the scope and spirit of the invention, it is intended that all subject matter contained in the above description, shown in the accompanying drawings, or defined in the appended claims be interpreted as illustrative, and not in a limiting sense.

The contents of all patents, patent applications, published articles, books, reference manuals, texts and abstracts cited herein are hereby incorporated by reference in their entirety to more fully describe the state of the art to which the present invention pertains.

What is claimed is:

1. An isolated polynucleotide comprising a nucleotide sequence encoding amino acid sequence SEQ ID NO:5.

2. An isolated polynucleotide comprising a nucleotide sequence encoding the NAD-binding domain of amino acid sequence SEQ ID NO:5, wherein said polynucleotide encodes a polypeotide having formate dehydrogenase activity, and wherein the NAD-binding domain of amino acid sequence SEQ ID NO:5 is amino acids 117–309 of SEQ ID NO:5.

3. An isolated polynucleotide comprising a nucleotide sequence encoding the catalytic domain of amino acid sequence SEQ ID NO:5, wherein said polynucleotide encodes a polypeptide having formate dehydrogenase activity, and wherein the catalytic domain of amino acid sequence SEQ ID NO:5 is amino acids 16–115 of SEQ ID NO:5.

4. An isolated nucleic acid of claim 1 comprising: (a) the nucleotide sequence SEQ ID NO:1; (b) the nucleotide sequence SEQ ID NO:3; or (c) a nucleotide sequence that differs from (a) or (b) due to degeneracy of the genetic code.

5. An isolated polynucleotide comprising a nucleotide sequence which is complementary to a nucleotide sequence of claim 1.

6. An isolated polynucleotide which hybridizes under high stringency conditions to any one of: (a) the nucleotide sequence SEQ ID NO:1; (b) the nucleotide sequence SEQ ID NO:3; (c) the complement of (a); (d) the complement of (b); or (e) a nucleotide sequence that differs from (a), (b), (c) or (d) due to degeneracy of the genetic code; wherein said polynucleotide encodes a polypeptide having formate dehydrogenase activity; and wherein said high stringency conditions are hybridization in 50% formamide, 5× Denhardt's solution. 5×SSPE, and 0.2% SDS at 42° C., followed by washing in 0.1×SSPE and 0.1% SDS at 65° C.

7. A vector comprising the isolated polynucleotide of claim 1.

8. A host cell transformed or transfected with the vector of claim 7, wherein the host cell is selected from the group consisting of bacterial, fungal, insect, mammalian, and plant cells.

9. An isolated polynucleotide comprising the nucleotide sequence encoding a formate dehydrogenase contained in the plasmid in the ATCC deposit designated PTA-3691.

10. A method for producing a recombinant polypeptide comprising the amino acid sequence SEQ ID NO:5 comprising:

a) culturing a host cell of claim 8 under conditions suitable for the production of a recombinant polypeptide; and b) recovering the recombinant polypeptide comprising the amino acid sequence SEQ ID NO:5 from the host cell or host cell culture, thereby producing the recombinant polypeptide.

11. A method of producing nicotinamide adenine dinucleotide (NAD+) in a reduced form (NADH) comprising: incubating the host cell of claim 8 with formate and NAD+ under conditions to allow oxidation of the formate and reduction of the NAD+, thereby producing NADH.

12. An isolated nucleic acid of claim 2, wherein said isolated polynucleotide further comprises a nucleotide sequence encoding the catalytic domain of amino acid sequence SEQ ID NO:5, and wherein the catalytic domain of amino acid sequence SEQ ID NO:5 is amino acids 16–115 of SEQ ID NO:5.

13. The isolated polynucleotide of claim 12, wherein said polypeptide shares at least 95% sequence identity with the amino acid sequence SEQ ID NO:5.

14. An isolated polynucleotide comprising a nucleotide sequence encoding a polypeptide that shares at least 95% sequence identity with amino acid sequence SEQ ID NO:5, wherein said polynucleotide encodes a polypeptide having formate dehydrogenase activity.

15. A vector comprising the isolated nucleic acid of claim 6, 13, or 14.

* * * * *

UNITED STATES PATENT AND TRADEMARK OFFICE
CERTIFICATE OF CORRECTION

PATENT NO. : 7,087,418 B2  Page 1 of 1
APPLICATION NO. : 10/320300
DATED : August 8, 2006
INVENTOR(S) : Steven L. Goldberg et al.

It is certified that error appears in the above-identified patent and that said Letters Patent is hereby corrected as shown below:

Title page,
Item [75], Inventors, "Venkata B. Nanduri and Robert M. Johnston" should be deleted in their entirety.

Claims - Column 71

Claim 2 - Line 4 - substitute "polypeotide" with --polypeptide--

Claim 4 - Line 1 - substitute "nucleic acid" with --polynucleotide--

Claims - Column 72

Claim 12 - Line 1 - substitute "nucleic acid" with --polynucleotide--

Claim 15 - Line 1 - substitute "nucleic acid" with --polynucleotide--

Signed and Sealed this

Fourth Day of September, 2007

JON W. DUDAS
*Director of the United States Patent and Trademark Office*

SEQUENCE LISTING

<160> NUMBER OF SEQ ID NOS: 25

<210> SEQ ID NO 1
<211> LENGTH: 1099
<212> TYPE: DNA
<213> ORGANISM: Pichia pastoris

<400> SEQUENCE: 1

```
atgaaaatcg ttctcgtttt gtactccgct ggtaagcacg ccgccgatga accaaagttg      60
tatggttgta tcgaaaatga attgggtatt agacaatggc ttgagaaggg cggccatgaa     120
ttggttacta catcagacaa agagggtgaa aactctgagt tagaaaagca cattcctgac     180
gctgatgtga ttatttccac tccattccat ccagcctaca tcacgaagga gagaatccaa     240
aaagccaaga agctgaagtt gttggtcgtt gctggtgtcg gttccgacca cattgacttg     300
gactacattg aacaaaatgg cctagatatt tcggtcctag aggttactgg ttccaacgtt     360
gtttcagtgg ctgagcatgt cgttatgact atattgaact tggtgagaaa ctttgttcca     420
gctcacgagc aaattgttaa ccccggctgg gacgttgctg ccatcgccaa ggacgcctac     480
gatattgaag gtaagaccat cgcaacaatt ggtgctggaa gaattggtta cagagtctta     540
gagagacttg tggctttcaa ccctaaggaa ttgttgtact acgactacca aggtcttcca     600
aaagaggccg aggaaaaagt tggtgccaga agagtcgaca ctgtcgagga gctggttgct     660
caagccgatg ttgttaccgt caatgcccca ctgcacgcag gtactaaggg tttagttaac     720
aaggagcttc tgtccaagtt caagaagggt gcttggttgg ttaacacagc cagaggtgcc     780
atctgcaatg ctcaagatgt cgctgatgcc gttgcatctg gtcaattgag aggttacggt     840
ggtgacgtct ggttccctca gccagctcca aaggaccatc catggagaga tatgagaaac     900
aagtacggat acggaaacgc catgactcct cattactcag gtaccacttt ggacgcccag     960
gtcagatatg ccgaaggtac caagaacatc ttgaactcat tccttaccaa gaagtttgac    1020
tacagacctc aagatgtcat tcttttgaac ggtaagtaca agaccaaggc ttatggtaat    1080
gacaaaaagg tcgcataaa                                                 1099
```

<210> SEQ ID NO 2
<211> LENGTH: 1099
<212> TYPE: DNA
<213> ORGANISM: Pichia pastoris

<400> SEQUENCE: 2

| | | | | | |
|---|---|---|---|---|---|
| tactttagc | aagagcaaaa | catgaggcga | ccattcgtgc | ggcggctact | tggtttcaac | 60 |
| ataccaacat | agcttttact | taacccataa | tctgttaccg | aactcttccc | gccggtactt | 120 |
| aaccaatgat | gtagtctgtt | tctcccactt | ttgagactca | atcttttcgt | gtaaggactg | 180 |
| cgactacact | aataaaggtg | aggtaaggta | ggtcggatgt | agtgcttcct | ctcttaggtt | 240 |
| tttcggttct | tcgacttcaa | caaccagcaa | cgaccacagc | caaggctggt | gtaactgaac | 300 |
| ctgatgtaac | ttgttttacc | ggatctataa | agccaggatc | tccaatgacc | aaggttgcaa | 360 |
| caaagtcacc | gactcgtaca | gcaatactga | tataacttga | accactcttt | gaaacaaggt | 420 |
| cgagtgctcg | tttaacaatt | ggggccgacc | ctgcaacgac | ggtagcggtt | cctgcggatg | 480 |
| ctataacttc | cattctggta | gcgttgttaa | ccacgacctt | cttaaccaat | gtctcagaat | 540 |
| ctctctgaac | accgaaagtt | gggattcctt | aacaacatga | tgctgatggt | tccagaaggt | 600 |
| tttctccggc | tcctttttca | accacggtct | tctcagctgt | gacagctcct | cgaccaacga | 660 |
| gttcggctac | aacaatggca | gttacggggt | gacgtgcgtc | catgattccc | aaatcaattg | 720 |
| ttcctcgaag | acaggttcaa | gttcttccca | cgaaccaacc | aattgtgtcg | gtctccacgg | 780 |
| tagacgttac | gagttctaca | gcgactacg | caacgtagac | cagttaactc | tccaatgcca | 840 |
| ccactgcaga | ccaagggagt | cggtcgaggt | ttcctggtag | gtacctctct | atactctttg | 900 |
| ttcatgccta | tgcctttgcg | gtactgagga | gtaatgagtc | catggtgaaa | cctgcgggtc | 960 |
| cagtctatac | ggcttccatg | gttcttgtag | aacttgagta | aggaatggtt | cttcaaactg | 1020 |
| atgtctggag | ttctacagta | agaaaacttg | ccattcatgt | tctggttccg | aataccatta | 1080 |
| ctgttttttcc | agcgtattt | | | | 1099 |

<210> SEQ ID NO 3
<211> LENGTH: 1690
<212> TYPE: DNA
<213> ORGANISM: Pichia pastoris

<400> SEQUENCE: 3

| | | | | | |
|---|---|---|---|---|---|
| ctaattctat | tcagtgtgct | gacctacacg | taatgatgtc | gtaacccagt | taaatggccg | 60 |
| aaaaactatt | taagtaagtt | tatttctcct | ccagatgaga | ctctccttct | tttctccgct | 120 |
| agttatcaaa | ctataaacct | attttacctc | aaatacctcc | aacatcaccc | acttaaacaa | 180 |
| tgaaaatcgt | tctcgttttg | tactccgctg | gtaagcacgc | cgccgatgaa | ccaaagttgt | 240 |
| atggttgtat | cgaaaatgaa | ttgggtatta | gacaatggct | tgagaagggc | ggccatgaat | 300 |
| tggttactac | atcagacaaa | gagggtgaaa | actctgagtt | agaaaagcac | attcctgacg | 360 |
| ctgatgtgat | tatttccact | ccattccatc | cagcctacat | cacgaaggag | agaatccaaa | 420 |
| aagccaagaa | gctgaagttg | ttggtcgttg | ctggtgtcgg | ttccgaccac | attgacttgg | 480 |
| actacattga | acaaaatggc | ctagatattt | cggtcctaga | ggttactggt | tccaacgttg | 540 |
| tttcagtggc | tgagcatgtc | gttatgacta | tattgaactt | ggtgagaaac | tttgttccag | 600 |
| ctcacgagca | aattgttaac | cccggctggg | acgttgctgc | catcgccaag | gacgcctacg | 660 |
| atattgaagg | taagaccatc | gcaacaattg | gtgctggaag | aattggttac | agagtcttag | 720 |
| agagacttgt | ggctttcaac | cctaaggaat | tgttgtacta | cgactaccaa | ggtcttccaa | 780 |

```
aagaggccga ggaaaaagtt ggtgccagaa gagtcgacac tgtcgaggag ctggttgctc    840
aagccgatgt tgttaccgtc aatgccccac tgcacgcagg tactaagggt ttagttaaca    900
aggagcttct gtccaagttc aagaagggtg cttggttggt taacacagcc agaggtgcca    960
tctgcaatgc tcaagatgtc gctgatgccg ttgcatctgg tcaattgaga ggttacggtg   1020
gtgacgtctg gttccctcag ccagctccaa aggaccatcc atggagagat atgagaaaca   1080
agtacggata cggaaacgcc atgactcctc attactcagg taccactttg gacgcccagg   1140
tcagatatgc cgaaggtacc aagaacatct tgaactcatt ccttaccaag aagtttgact   1200
acagacctca agatgtcatt cttttgaacg gtaagtacaa gaccaaggct tatggtaatg   1260
acaaaaaggt cgcataattg aaatgtattt aatttgatat taagtaaatg aatgattatg   1320
actttatgaa ttcacgtggc ccagccggcc gtctcggatc ggtacctcga gccgcggcgg   1380
ccgccagctt gggcccgaac aaaaactcat ctcagaagag gatctgaata gcgccgtcga   1440
ccatcatcat catcatcatt gagttttagc cttagacatg actgttcctc agttcaagtt   1500
gggcacttac gagaagaccg gtcttgctag attctaatca agaggatgtc agaatgccat   1560
ttgcctgaga gatgcaggct tcattttttga tactttttta tttgtaccct atatagtata   1620
ggattttttt tgtcattttg tttcttctcg tacgagcttg ctcctgatca gcctatctcc   1680
cagctgatga                                                          1690

<210> SEQ ID NO 4
<211> LENGTH: 1690
<212> TYPE: DNA
<213> ORGANISM: Pichia pastoris

<400> SEQUENCE: 4
gattaagata agtcacacga ctggatgtgc attactacag cattgggtca atttaccggc     60 ttttttgataa attcattcaa ataaagagga ggtctactct gagaggaaga aaagaggcga    120
tcaatagttt gatatttgga taaaatggag tttatggagg ttgtagtggg tgaatttgtt    180
acttttagca agagcaaaac atgaggcgac cattcgtgcg gcggctactt ggtttcaaca    240
taccaacata gcttttactt aacccataat ctgttaccga actcttcccg ccggtactta    300
accaatgatg tagtctgttt ctcccacttt tgagactcaa tcttttcgtg taaggactgc    360
gactacacta ataaggtgga ggtaaggtag gtcggatgta gtgcttcctc tcttaggttt    420
ttcggttctt cgacttcaac aaccagcaac gaccacagcc aaggctggtg taactgaacc    480
tgatgtaact tgttttaccg gatctataaa gccaggatct ccaatgacca aggttgcaac    540
aaagtcaccg actcgtacag caatactgat ataacttgaa ccactctttg aaacaaggtc    600
gagtgctcgt ttaacaattg gggccgaccc tgcaacgacg gtagcggttc ctgcggatgc    660
tataacttcc attctggtag cgttgttaac cacgaccttc ttaaccaatg tctcagaatc    720
tctctgaaca ccgaaagttg ggattcctta acaacatgat gctgatggtt ccagaaggtt    780
ttctccggct ccttttttcaa ccacggtctt ctcagctgtg acagctcctc gaccaacgag    840
ttcggctaca acaatggcag ttacggggtg acgtgcgtcc atgattccca atcaattgt     900 tcctcgaaga caggttcaag ttcttcccac gaaccaacca attgtgtcgg tctccacggt    960
agacgttacg agttctacag cgactacggc aactagacc agttaactct ccaatgccac   1020
cactgcagac caagggagtc ggtcgaggtt cctggtaggg tacctctcta tactctttgt   1080
tcatgcctat gcctttgcgg tactgaggag taatgagtcc atggtgaaac ctgcgggtcc   1140
agtctatacg gcttccatgg ttcttgtaga acttgagtaa ggaatggttc ttcaaactga   1200
```

```
tgtctggagt ctacagtaa gaaaacttgc cattcatgtt ctggttccga ataccattac    1260
tgtttttcca gcgtattaac tttacataaa ttaaactata attcatttac ttactaatac    1320
tgaaatactt aagtgcaccg ggtcggccgg cagagcctag ccatggagct cggcgccgcc    1380
ggcggtcgaa cccgggcttg tttttgagta gagtcttctc ctagacttat cgcggcagct    1440
ggtagtagta gtagtagtaa ctcaaaatcg gaatctgtac tgacaaggag tcaagttcaa    1500
cccgtgaatg ctcttctggc cagaacgatc taagattagt tctcctacag tcttacggta    1560
aacggactct ctacgtccga agtaaaaact atgaaaaaat aaacatggga tatatcatat    1620
cctaaaaaaa acagtaaaac aaagaagagc atgctcgaac gaggactagt cggatagagg    1680
gtcgactact                                                            1690
```

<210> SEQ ID NO 5
<211> LENGTH: 365
<212> TYPE: PRT
<213> ORGANISM: Pichia pastoris

<400> SEQUENCE: 5

```
Met Lys Ile Val Leu Val Leu Tyr Ser Ala Gly Lys His Ala Ala Asp
1               5                   10                  15

Glu Pro Lys Leu Tyr Gly Cys Ile Glu Asn Glu Leu Gly Ile Arg Gln
            20                  25                  30

Trp Leu Glu Lys Gly Gly His Glu Leu Val Thr Thr Ser Asp Lys Glu
        35                  40                  45

Gly Glu Asn Ser Glu Leu Glu Lys His Ile Pro Asp Ala Asp Val Ile
    50                  55                  60

Ile Ser Thr Pro Phe His Pro Ala Tyr Ile Thr Lys Glu Arg Ile Gln
65                  70                  75                  80

Lys Ala Lys Lys Leu Lys Leu Val Val Ala Gly Val Gly Ser Asp
                85                  90                  95

His Ile Asp Leu Asp Tyr Ile Glu Gln Asn Gly Leu Asp Ile Ser Val
                100                 105                 110

Leu Glu Val Thr Gly Ser Asn Val Val Ser Val Ala Glu His Val Val
            115                 120                 125

Met Thr Ile Leu Asn Leu Val Arg Asn Phe Val Pro Ala His Glu Gln
130                 135                 140

Ile Val Asn Pro Gly Trp Asp Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Val Ala Phe Asn Pro Lys Glu Leu Leu
            180                 185                 190

Tyr Tyr Asp Tyr Gln Gly Leu Pro Lys Glu Ala Glu Lys Val Gly
        195                 200                 205

Ala Arg Arg Val Asp Thr Val Glu Glu Leu Val Ala Gln Ala Asp Val
    210                 215                 220

Val Thr Val Asn Ala Pro Leu His Ala Gly Thr Lys Gly Leu Val Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Asn Ala Gln Asp Val Ala Asp Ala Val Ala
            260                 265                 270

Ser Gly Gln Leu Arg Gly Tyr Gly Gly Asp Val Trp Phe Pro Gln Pro
        275                 280                 285
```

Ala Pro Lys Asp His Pro Trp Arg Asp Met Arg Asn Lys Tyr Gly Tyr
    290                 295                 300

Gly Asn Ala Met Thr Pro His Tyr Ser Gly Thr Thr Leu Asp Ala Gln
305                 310                 315                 320

Val Arg Tyr Ala Glu Gly Thr Lys Asn Ile Leu Asn Ser Phe Leu Thr
                325                 330                 335

Lys Lys Phe Asp Tyr Arg Pro Gln Asp Val Ile Leu Leu Asn Gly Lys
                340                 345                 350

Tyr Lys Thr Lys Ala Tyr Gly Asn Asp Lys Lys Val Ala
                355                 360                 365

<210> SEQ ID NO 6
<211> LENGTH: 21
<212> TYPE: DNA
<213> ORGANISM: Candida boidinii

<400> SEQUENCE: 6
atgaagatcg ttttagtctt a                                         21

<210> SEQ ID NO 7
<211> LENGTH: 21
<212> TYPE: DNA
<213> ORGANISM: Candida boidinii

<400> SEQUENCE: 7
tttcttatcg tgtttaccgt a                                         21

<210> SEQ ID NO 8
<211> LENGTH: 20
<212> TYPE: DNA
<213> ORGANISM: Pichia pastoris

<400> SEQUENCE: 8
ttttctaact cagagttttc                                           20

<210> SEQ ID NO 9
<211> LENGTH: 19
<212> TYPE: DNA
<213> ORGANISM: Pichia pastoris

<400> SEQUENCE: 9
aaccaattct tccagcacc                                            19

<210> SEQ ID NO 10
<211> LENGTH: 20
<212> TYPE: DNA
<213> ORGANISM: Pichia pastoris

<400> SEQUENCE: 10
tacctgagta atgaggagtc                                           20

<210> SEQ ID NO 11
<211> LENGTH: 20
<212> TYPE: DNA
<213> ORGANISM: Pichia pastoris

<400> SEQUENCE: 11
aaacccaatc gggaaacttt                                           20

-continued

<210> SEQ ID NO 12
<211> LENGTH: 15
<212> TYPE: DNA
<213> ORGANISM: Pichia pastoris

<400> SEQUENCE: 12
gtaccaaaat ggcaa                                                    15

<210> SEQ ID NO 13
<211> LENGTH: 20
<212> TYPE: DNA
<213> ORGANISM: Pichia pastoris

<400> SEQUENCE: 13
caaaggctac agaaatccca                                               20

<210> SEQ ID NO 14
<211> LENGTH: 26
<212> TYPE: DNA
<213> ORGANISM: Pichia pastoris

<400> SEQUENCE: 14
tcgtcatgaa aatcgttctc gttttg                                        26

<210> SEQ ID NO 15
<211> LENGTH: 28
<212> TYPE: DNA
<213> ORGANISM: Pichia pastoris

<400> SEQUENCE: 15
tactgttttt ccagcgtatt cctaggct                                      28

<210> SEQ ID NO 16
<211> LENGTH: 15
<212> TYPE: PRT
<213> ORGANISM: Gluconobacter oxydans

<400> SEQUENCE: 16

Ser Leu Ser Gly Lys Ile Ala Ala Val Thr Gly Ala Ala Gln Gly
1               5                   10                  15

<210> SEQ ID NO 17
<211> LENGTH: 11
<212> TYPE: PRT
<213> ORGANISM: Gluconobacter oxydans

<400> SEQUENCE: 17

Lys Arg Met Ala Glu Ile Thr Gly Thr Glu Ile
1               5                   10

<210> SEQ ID NO 18
<211> LENGTH: 10
<212> TYPE: PRT
<213> ORGANISM: Gluconobacter oxydans

<400> SEQUENCE: 18

Lys Val Glu Ala Leu Gly Arg Arg Ala Val
1               5                   10

<210> SEQ ID NO 19
<211> LENGTH: 29
<212> TYPE: DNA
<213> ORGANISM: Gluconobacter oxydans

```
<220> FEATURE:
<221> NAME/KEY: misc_feature
<222> LOCATION: (6)..(27)
<223> OTHER INFORMATION: wherein n = deoxyinosine (i)
<220> FEATURE:
<221> NAME/KEY: misc_feature
<222> LOCATION: (17)..(20)
<223> OTHER INFORMATION: wherein m = a or c
<220> FEATURE:
<221> NAME/KEY: misc_feature
<222> LOCATION: (3)..(9)
<223> OTHER INFORMATION: wherein r = a or g
<220> FEATURE:
<221> NAME/KEY: misc_feature
<222> LOCATION: (13)..(13)
<223> OTHER INFORMATION: wherein y = c or t

<400> SEQUENCE: 19
aargtngarg cnytnggnmg nmgngcngt                               29

<210> SEQ ID NO 20
<211> LENGTH: 26
<212> TYPE: DNA
<213> ORGANISM: Gluconobacter oxydans
<220> FEATURE:
<221> NAME/KEY: misc_feature
<222> LOCATION: (6)..(22)
<223> OTHER INFORMATION: wherein n = deoxyinosine (i)
<220> FEATURE:
<221> NAME/KEY: misc_feature
<222> LOCATION: (3)..(18)
<223> OTHER INFORMATION: wherein y = c or t

<400> SEQUENCE: 20
atytcngtnc cngtnatytc ngccat                                  26

<210> SEQ ID NO 21
<211> LENGTH: 32
<212> TYPE: DNA
<213> ORGANISM: Gluconobacter oxydans

<400> SEQUENCE: 21
ggaattccat atgtcccttt ctggaaaatc gc                           32

<210> SEQ ID NO 22
<211> LENGTH: 23
<212> TYPE: DNA
<213> ORGANISM: Gluconobacter oxydans

<400> SEQUENCE: 22
cgggatcctc tcagcggaaa acg                                     23

<210> SEQ ID NO 23
<211> LENGTH: 1575
<212> TYPE: DNA
<213> ORGANISM: Gluconobacter oxydans
<220> FEATURE:
<221> NAME/KEY: misc_feature
<222> LOCATION: (7)..(126)
<223> OTHER INFORMATION: wherein d = a or t or g
<220> FEATURE:
<221> NAME/KEY: misc_feature
<222> LOCATION: (40)..(1557)
<223> OTHER INFORMATION: wherein k = t or g
<220> FEATURE:
<221> NAME/KEY: misc_feature
<222> LOCATION: (10)..(1294)
<223> OTHER INFORMATION: wherein s = c or g
```

```
<220> FEATURE:
<221> NAME/KEY: misc_feature
<222> LOCATION: (6)..(1456)
<223> OTHER INFORMATION: wherein n = a or t or c or g
<220> FEATURE:
<221> NAME/KEY: misc_feature
<222> LOCATION: (20)..(21)
<223> OTHER INFORMATION: wherein v = a or c or g
<220> FEATURE:
<221> NAME/KEY: misc_feature
<222> LOCATION: (45)..(109)
<223> OTHER INFORMATION: wherein y = c or t
<220> FEATURE:
<221> NAME/KEY: misc_feature
<222> LOCATION: (1381)..(1382)
<223> OTHER INFORMATION: wherein m = a or c
<220> FEATURE:
<221> NAME/KEY: misc_feature
<222> LOCATION: (51)..(186)
<223> OTHER INFORMATION: wherein r = a or g
<220> FEATURE:
<221> NAME/KEY: misc_feature
<222> LOCATION: (65)..(1347)
<223> OTHER INFORMATION: wherein b = c or t or g

<400> SEQUENCE: 23
cggggnddds ggnsggcggv vataggcgnd gdaccscctk ddttyccogg raagaagaca      60 tsssbcycat ggatggaaat ttccccatga tgcccatgga tttcccssyt gaagatcatc    120
cggsgdaaac gaaggcatcg tnacgccctg gatttcggga atatggacgg acgacaccag    180
gacctraagc cattccctca tcgctgatgc caccaaaggt ctcaaaaacg gcactaatgc    240
tgtccgtgtg gttcatcaag tcctgccgag gctcttcgta acgtttattt aacgcatcct    300
cgcaggcccg gaaacagatg accagagtag gtttatgaaa attatcctta cccaggacag    360
gccccgtccc ctttgacaca atcctgtgtc aggcctgccg aacaggcgtt tttttgtgga    420
atacggaaag caagggttg atggttcccg ccgtcatggc agtcacatgc cgatgacgga    480
caatcgaagg atcttttttc aatgtcccctt tctggaaaaa tcgccgcagt cacgggtgca    540
gcccagtgta tcggcaaggc cattgcgctt cgtctggcca aggatggcgc ggatgtcatc    600
ctgctcgacg tcaagcagga cacgcttgcc gaaaccgcaa aggaagttga agctctcggc    660
cggcgcgctg tggccctgac ggccgatatc agcaaccgcg accagttccg cagcacgctg    720
gccgatgcag caaagacgct cggcggcctg gacatcatgg tcaacaatgc ggggatctgt    780
caggtcaagc cgatcctgga catcgagcct gcggaaatcg agaagatctt cagcatcaac    840
gttcagggcg tgctctgggg catgcaggcg gctgcgaccc tcttcaagga aagggcacc    900 aagggcaaga tcatcaatgc ctgctcgatc gccggccatg aaggctatcc ccttctgggc    960
gcctattccg cgaccaaatt cgccgtccgc gccctgacgc agtcggccgc caaggaactc   1020
gcgtcctcgg gcattaccgt caattcctac tgccccggca ttgtcggaac cgacatgtgg   1080
gtcacgatcg acaagcgcat ggccgaaatc accggtacga aaatcggcgc gacctacaag   1140
aaatacgttg aaggaatcgc tcttggccgc gtggagacgg cggacgatgt ggcgggcttc   1200
gtcgcctatt tgtccagcag tgacgccgat tacatgacgg gtcagtccgt cctgatcaac   1260
ggtggtcccg ttttccgctg agatcataaa aaasagggcc ggtttcccgc gccccttttt   1320
ttgtcagcgg ccgatcagac ggccgbgctg ccaggcttcg gcggcccctt ccgggtcctg   1380
mmcttcaacg gaaatgacat agtccagggc gctcatgacc ctgttgccaa gcatcatttc   1440
cgaaagctcg tcgagnagat cgctgtccgc ctgacgggcc acatcttcac gcatgatcat   1500
```

```
ccgggccgac atttctccgc ccagcaggtg ggccggatcc gagctcggta ccaagcktga    1560
tgcatagctt gagta                                                    1575
```

<210> SEQ ID NO 24
<211> LENGTH: 259
<212> TYPE: PRT
<213> ORGANISM: Gluconobacter oxydans

<400> SEQUENCE: 24

```
Met Ser Leu Ser Gly Lys Ile Ala Ala Val Thr Gly Ala Ala Gln Cys
1               5                   10                  15
Ile Gly Lys Ala Ile Ala Leu Arg Leu Ala Lys Asp Gly Ala Asp Val
                20                  25                  30
Ile Leu Leu Asp Val Lys Gln Asp Thr Leu Ala Glu Thr Ala Lys Glu
            35                  40                  45
Val Glu Ala Leu Gly Arg Arg Ala Val Ala Leu Thr Ala Asp Ile Ser
    50                  55                  60
Asn Arg Asp Gln Phe Arg Ser Thr Leu Ala Asp Ala Ala Lys Thr Leu
65                  70                  75                  80
Gly Gly Leu Asp Ile Met Val Asn Asn Ala Gly Ile Cys Gln Val Lys
                85                  90                  95
Pro Ile Leu Asp Ile Glu Pro Ala Glu Ile Glu Lys Ile Phe Ser Ile
                100                 105                 110
Asn Val Gln Gly Val Leu Trp Gly Met Gln Ala Ala Thr Leu Phe
            115                 120                 125
Lys Glu Lys Gly Thr Lys Gly Lys Ile Ile Asn Ala Cys Ser Ile Ala
    130                 135                 140
Gly His Glu Gly Tyr Pro Leu Leu Gly Ala Tyr Ser Ala Thr Lys Phe
145                 150                 155                 160
Ala Val Arg Ala Leu Thr Gln Ser Ala Ala Lys Glu Leu Ala Ser Ser
                165                 170                 175
Gly Ile Thr Val Asn Ser Tyr Cys Pro Gly Ile Val Gly Thr Asp Met
                180                 185                 190
Trp Val Thr Ile Asp Lys Arg Met Ala Glu Ile Thr Gly Thr Glu Ile
            195                 200                 205
Gly Ala Thr Tyr Lys Lys Tyr Val Glu Gly Ile Ala Leu Gly Arg Val
    210                 215                 220
Glu Thr Ala Asp Asp Val Ala Gly Phe Val Ala Tyr Leu Ser Ser Ser
225                 230                 235                 240
Asp Ala Asp Tyr Met Thr Gly Gln Ser Val Leu Ile Asn Gly Gly Pro
                245                 250                 255
Val Phe Arg
```

<210> SEQ ID NO 25
<211> LENGTH: 1095
<212> TYPE: DNA
<213> ORGANISM: Candida boidinii

<400> SEQUENCE: 25

```
atgaagatcg ttttagtctt atatgatgct ggtaagcacg ctgctgatga agaaaaatta    60
tatggttgta ctgaaaataa attaggtatt gctaattggt taaagatca aggtcatgaa    120 ctaattacta cttctgataa agaaggtgaa acaagtgaat tggataaaca tatcccagat    180
gctgatatta tcatcaccac tccttttccat cctgcttata tcactaagga aagacttgac    240
aaggctaaga acttaaaatc agtcgttgtc gctggtgttg gttctgatca cattgattta    300
```

-continued

```
gattatatta atcaaacagg taagaaaatc tcagtcctgg aagttacagg ttctaatgtt    360
gtctctgttg ctgaacacgt tgtcatgacc atgcttgtct tggttagaaa tttcgttcca    420
gcacatgaac aaattattaa ccacgattgg gaggttgctg ctatcgctaa ggatgcttac    480
gatatcgaag gtaaaactat cgctaccatt ggtgctggta gaattggtta cagagtcttg    540
gaaagattac tcccatttaa tccaaaagaa ttattatact acgattatca agctttacca    600
aaagaagctg aagaaaaagt tggtgctaga agagttgaaa atattgaaga attagttgct    660
caagctgata tcgttacagt taatgctcca ttacacgcag gtacaaaagg tttaattaat    720
aaggaattat tatctaaatt taaaaaaggt gcttggttag tcaataccgc aagaggtgct    780
atttgtgttg ctgaagatgt tgcagcagct ttagaatctg gtcaattaag aggttacggt    840
ggtgatgttt ggttcccaca accagctcca aaggatcacc catggagaga tatgagaaat    900
aaatatggtg ctggtaatgc catgactcct cactactctg gtactacttt agacgctcaa    960
acaagatacg ctgaaggtac taaaaatatt ttggaatcat tctttaccgg taaatttgat   1020
tacagaccac aagatattat cttattaaat ggtgaatacg ttactaaagc ttacggtaaa   1080
cacgataaga aataa                                                    1095
```